(12) United States Patent
Li et al.

(10) Patent No.: US 7,638,604 B2
(45) Date of Patent: Dec. 29, 2009

(54) MONOCLONAL ANTIBODIES AGAINST INTERLEUKIN-22

(75) Inventors: Jing Li, Lexington, MA (US); Xiang-Yang Tan, Reading, MA (US); Kathleen N. Tomkinson, Cambridge, MA (US); Debra D. Pittman, Windham, NH (US); Geertruida M. Veldman, Sudbury, MA (US); Lynette Fouser, Acton, MA (US)

(73) Assignee: Genetics Institute, LLC, Cambridge, MA (US)

( * ) Notice: Subject to any disclaimer, the term of this patent is extended or adjusted under 35 U.S.C. 154(b) by 407 days.

(21) Appl. No.: 10/873,972

(22) Filed: Jun. 22, 2004

(65) Prior Publication Data

US 2005/0042220 A1 Feb. 24, 2005

Related U.S. Application Data

(63) Continuation-in-part of application No. 10/084,298, filed on Feb. 25, 2002, now Pat. No. 6,939,545.

(60) Provisional application No. 60/480,652, filed on Jun. 23, 2003, provisional application No. 60/270,823, filed on Feb. 23, 2001, provisional application No. 60/281,353, filed on Apr. 3, 2001.

(51) Int. Cl.
*C12P 21/08* (2006.01)
*A61K 39/395* (2006.01)

(52) U.S. Cl. ............... 530/388.1; 424/145.1; 435/70.21

(58) Field of Classification Search ....................... None
See application file for complete search history.

(56) References Cited

U.S. PATENT DOCUMENTS

| | | | |
|---|---|---|---|
| 5,350,836 | A | 9/1994 | Kopchick et al. |
| 5,536,637 | A | 7/1996 | Jacobs |
| 5,674,487 | A | 10/1997 | Smith et al. |
| 5,837,232 | A | 11/1998 | DeWaal Malefyt et al. |
| 5,863,796 | A | 1/1999 | Moore et al. |
| 6,225,117 | B1 | 5/2001 | Gately et al. |
| 6,274,710 | B1 | 8/2001 | Dumoutier et al. |
| 6,331,613 | B1 | 12/2001 | Dumoutier et al. |
| 6,359,117 | B1 | 3/2002 | Dumoutier et al. |
| 6,551,799 | B2 | 4/2003 | Gurney et al. |
| 2001/0006637 | A1 | 7/2001 | Akahoshi et al. |
| 2001/0024652 | A1 | 9/2001 | Dumoutier et al. |
| 2002/0012669 | A1 | 1/2002 | Presnell et al. |
| 2002/0102723 | A1 | 8/2002 | Gurney et al. |
| 2002/0187523 | A1 | 12/2002 | Tang et al. |
| 2003/0012788 | A1 | 1/2003 | Renauld et al. |
| 2003/0099649 | A1 | 5/2003 | Fouser et al. |
| 2003/0157106 | A1* | 8/2003 | Jacobs et al. ............. 424/145.1 |
| 2003/0170823 | A1 | 9/2003 | Presnell et al. |
| 2004/0023341 | A1 | 2/2004 | Xu et al. |
| 2004/0110189 | A1 | 6/2004 | Dumoutier et al. |
| 2004/0152125 | A1 | 8/2004 | Presnell et al. |
| 2004/0180399 | A1 | 9/2004 | Renauld et al. |

FOREIGN PATENT DOCUMENTS

| | | |
|---|---|---|
| WO | WO 94/01548 | 1/1994 |
| WO | WO 99/61617 | 12/1999 |
| WO | WO 00/24758 | 5/2000 |
| WO | WO 00/70049 | 11/2000 |
| WO | WO 00/73457 | 12/2000 |
| WO | WO 00/77037 | 12/2000 |
| WO | WO 01/46422 | 6/2001 |
| WO | WO 02/10393 | 2/2002 |
| WO | WO 02/16611 | 2/2002 |
| WO | WO 02/068476 | 9/2002 |

OTHER PUBLICATIONS

Compact Oxford English Dictionary entry for "composition". http://www.askoxford.com/concise_oed/composition?view=uk. Accessed Sep. 15, 2007.*
R&D Systems, Catalog NR, AF582, XP002307633, "Anti-Mouse IL-22 Antibody", Aug. 22, 2002.
Kotenko, Sergei, "The Family of IL-10-Related Cytokines and Their Receptors: Related, But To What Extent?", Cytokine and Growth Factor Reviews, vol. 13, No. 3, Jun. 2002, pp. 223-240.
Dumoutier, L., et al, "Human Interleukin-10-Related T Cell-Derived Inducible Factor: Molecular Cloning and Functional Characterization as an Hepatocyte-Stimulating Factor", PNAS, vol. 97, No. 18, Aug. 29, 2000, pp. 10144-10149.
Radaeva, Svetlana, et al, "Interleukin 22 (IL-22) Plays a Protective Role in T Cell-Mediated Murine Hepatitis: IL-22 is a Survival Factor for Hepatocytes via STAT3 Activation", Hepatology, vol. 39, No. 5, May 2004, pp. 1332-1342.
Resmini, Christine, et al, "An Anti-Murine IL-22 Monoclonal Antibody Decreases Disease Severity in a Murine Model of Collagen Induced Arthritis", European Cytokine Network, vol. 14, No. Supplement 3, Sep., 2003, p. 129 and Annual Meeting of the International Cytokine Society; Dublin, Ireland, Sep. 20-24, 2003, ISSN: 1148-5493.
Li, J., et al, "Temporal Associations Between Interleukin 22 and the Extracellular Domains of IL-22R and IL-10R2", International Immunopharmacology, Elsevier, Amsterdam, NL, vol. 4, No. 5, May 2004, pp. 693-708.
International Search Report for International Application No. PCT/US04/020833.

(Continued)

*Primary Examiner*—Lorraine Spector
*Assistant Examiner*—Elly-Gerald Stoica
(74) *Attorney, Agent, or Firm*—Latimer and Mayberry IP Law, LLP

(57) ABSTRACT

Antibodies and antigen-binding fragments thereof that bind interleukin-22 (IL-22), in particular, human IL-22, and their uses in regulating IL-22-associated immune responses are disclosed. The antibodies disclosed herein are useful in diagnosing, preventing, or treating IL-22-associated immune disorders, e.g., autoimmune disorders (e.g., arthritis).

1 Claim, 15 Drawing Sheets

OTHER PUBLICATIONS

Bork, P., Genome Research 10:398-400, 2000.
Doerks, et al, Trends in Genetics 14:248-250, 1998.
Smith, et al, Nature Biotechnology 15:1222-1223, 1997.
Brenner, S.E., Trends in Genetics 15:132-133, 1999.
Mahairas, et al., PNAS, USA, 96(17) 9739-9744 (1999).
Simon L.S., et al (Jun., 2000), New and future drug therapies for rheumatoid arthritis, Rheumatology 39:36-42.
Liorente L., et al. (2000), Clinical and Biological Effects of Anti-Interleukin-10 Monoclonal Antibody Administration in Systemic Lupus Erythematosus, Arthritis & Rheumatism 43(8): 1790-1800.
van den Berg, W. (1998), Joint Inflammation and Cartilage Destruction May Occur Uncoupled, Springer Semin. Immunopathol. 20:149-164.
International Search Report for International Application No. PCT/US02/05684.
International Search Report for International Application No. PCT/US00/11479.
European Search Report issued in EP Application No. 00928535.4-Jul. 14, 2004.
Dumoutier, L., et al: "Cloning and Characterization of IL-10-Related T Cell-Derived Inducible Factor (IL-TIF), A novel cytokine structurally related to IL-10 and Inducible by IL-9" Journal of Immunology, Blackwell Scientific Publications, GB, vol. 164, 2000, pp. 1814-1819.
Xie, M-H et al: "Interleukin (IL)-22, a Novel Human Cytokine that Signals Through the Interferon Receptor-Related Proteins CRF2-4 and IL-22R" Journal of Biological Chemistry, vol. 275, No. 40, Oct. 6, 2000, pp. 31335-31339.
Kotenko, Sergei V. et al: "Identification of the Functional Interleukin-22 (IL-22) receptor complex. The IL-10R2 Chain (IL-10Rbeta) is a Common Chain of Both the IL-10 and IL-22 (IL-10-related T cell-derived inducible factor, IL-TIF) Receptor Complexes" Journal of Biological Chemistry, vol. 276, No. 4, Jan. 26, 2001, pp. 2725-2732.
Dumoutier, L., et al: "IL-TIF induces acute phase reactant production by hepatocytes through IL-10Rbeta" Immunology Letters, vol. 73, No. 2-3 Sep. 2000, p. 261.
Lambert, A., et al: "Novel cytokine IL-22 administered by adenovirus vector or as recombinant purified protein induces acute-phase responses and renal tubular basophilia in female C57BL/6 mice." Toxicologic Pathology, vol. 29, No. 6, Nov. 2001, p. 712.
Mahairas G., et al Database EST. Accession No. AQ104025 Aug. 28, 1998.
Waterston R., et al Database GenEmbl. Accession No. AC006734 Feb. 25, 1999.
Wilson R., et al J. Mol. Biol. 261:155-172, 1996.
Bork, et al, Trends in Genetics 12:425-427, 1996.
Vukicevic, et al, PNAS USA 93:9021-9026, 1996.
Massague J. Cell 49:437-38, 1987.
Philbeam, et al Bone 14:717-720, 1993.
Skolnick, et al Trends in Biotech 18:34-39, 2000.
Syrbe, et al (1999) Springer Seminars in Immunopathology, 21:263-85.
Dumoutier, L., et al GenBank Accession No. NM_016971 for mus musculus interleukin 10-related T cell-derived inducible factor (Iltif). Jun. 8, 2000.
Aoki, I., et al. "Comparison of the amino acid and nucleotide sequences between human and two guinea pit major basic proteins," FEBS Lett. 282(1):56-60, 1991.
Dumoutier, L., et al., "IL-TIF/IL-22: genomic organization and mapping of the human and mouse genes," Genes Immun. 1:488-494, 2000.
Ozaki, T., et al GenBank Accession No. D13973 for Dictyostelium Discoideum DNA for Dp87 protein, 1993. Feb. 1, 2000.
Aoki, I., et al GenBank Accession No. P35709 for Eosinophil Granule Major Basic Protein 2 Percursor (mbp-2). May 30, 2000.
Xie, M., et al GenBank Accession No. AF279437 for Homo Sapiens Interleukin 22 (IL22). Oct. 9, 2000.
Dumoutier, L., et al GenBank Accession No. AJ294727 for Mus musculus ILTIFa gene for IL TIE alpha protein (IL-21), exons 1a 5. Dec. 21, 2000.
Dumoutier, L., et al GenBank Accession No. NP_065386 for Interleukin 22; interleukin 21; IL-10-related T-cell-derived inducible factor (homo sapiens). Nov. 2, 2000.
Ozaki, T., et al, "Developmental regulation of transcription of a novel prespore-specific gene (Dp87) in Dictyostelium discoideum," Development. 117(4): 1299-308, 1993.
Sambrook, J., et al Molecular Cloning. A Laboratory Manual, 2d ed. Cold Spring Harbor Laboratory Press, 1989, Ch. 17.

* cited by examiner

SEQUENCE LISTING

<160> NUMBER OF SEQ ID NOS: 10

<210> SEQ ID NO 1
<211> LENGTH: 1191
<212> TYPE: DNA
<213> ORGANISM: Homo sapiens

<400> SEQUENCE: 1

```
gaattcggcc aaagaggcct acaggttctc cttcccagt caccagttgc tcgagttaga      60
attgtctgca atggccgccc tgcagaaatc tgtgagctct ttccttatgg ggaccctggc     120
caccagctgc ctccttctct tggccctctt ggtacaggga ggagcagctg cgcccatcag    180
ctcccactgc aggcttgaca agtccaactt ccagcagccc tatatcacca accgcacctt    240
catgctggct aaggaggcta gcttggctga taacaacaca gacgttcgtc tcattgggga    300
gaaactgttc cacggagtca gtatgagtga gcgctgctat ctgatgaagc aggtgctgaa    360
cttcaccctt gaagaagtgc tgttccctca atctgatagg ttccagcctt atatgcagga    420
ggtggtgccc ttcctggcca ggctcagcaa caggctaagc acatgtcata ttgaaggtga    480
tgacctgcat atccagagga atgtgcaaaa gctgaaggac acagtgaaaa agcttggaga    540
gagtggagag atcaaagcaa ttggagaact ggatttgctg tttatgtctc tgagaaatgc    600
ctgcatttga ccagagcaaa gctgaaaaat gaataactaa cccccttccc ctgctagaaa    660
taacaattag atgccccaaa gcgattttt ttaaccaaaa ggaagatggg aagccaaact    720
ccatcatgat gggtggattc caaatgaacc cctgcgttag ttacaaagga accaatgcc    780
acttttgttt ataagaccag aaggtagact ttctaagcat agatatttat tgataacatt    840
tcattgtaac tggtgttcta tacacagaaa acaatttatt ttttaaataa ttgtcttttt    900
ccataaaaaa gattactttc cattccttta ggggaaaaaa cccctaaata gcttcatgtt    960
tccataatca gtactttata tttataaatg tatttattat tattataaga ctgcatttta   1020
tttatatcat tttattaata tggatttatt tatagaaaca tcattcgata ttgctacttg   1080
agtgtaaggc taatattgat atttatgaca ataattatag agctataaca tgtttatttg   1140
```

-continued acctcaataa acacttggat atcctaaaaa aaaaaaaaaa aaagcggccg c                          1191

<210> SEQ ID NO 2
<211> LENGTH: 179
<212> TYPE: PRT
<213> ORGANISM: Homo sapiens

<400> SEQUENCE: 2

Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 3
<211> LENGTH: 1166
<212> TYPE: DNA
<213> ORGANISM: Mus musculus

<400> SEQUENCE: 3
gaattcggcc aaagaggcct acctaaacag gctctcctct cagttatcaa ctgttgacac      60
ttgtgcgatc tctgatggct gtcctgcaga atctatgag ttttttccctt atggggactt    120 tggccgccag ctgcctgctt ctcattgccc tgtgggccca ggaggcaaat gcgctgcccg    180
tcaacacccg gtgcaagctt gaggtgtcca cttccagca gccatacatc gtcaaccgca    240
cctttatgct ggccaaggag gccagccttg cagataacaa cacagatgtc cggctcatcg    300
gggagaaact gttccgagga gtcagtgcta aggatcagtg ctacctgatg aagcaggtgc    360
tcaacttcac cctggaagac gttctgctcc cccagtcaga caggttccag ccctacatgc    420
aggaggtggt gcctttcctg accaaactca gcaatcagct cagctcctgt cacatcagcg    480
gtgacgacca gaacatccag aagaatgtca aaggctgaa ggagacagtg aaaaagcttg    540
gagagagtgg agagatcaag gcgattgggg aactggacct gctgtttatg tctctgagaa    600
atgcttgcgt ctgagcgaga agaagctaga aaacgaagaa ctgctccttc ctgccttcta    660
aaaagaacaa taagatccct gaatggactt ttttactaaa ggaaagtgag aagctaacgt    720
ccatcattat tagaagattt cacatgaaac ctggctcagt tgaaaaagaa aatagtgtca    780

-continued

```
agttgtccat gagaccagag gtagacttga taaccacaaa gattcattga caatatttta    840
ttgtcactga tgatacaaca gaaaataat gtactttaaa aaattgtttg aaaggaggtt    900
acctctcatt cctttagaaa aaaagcttat gtaacttcat ttccataacc aatattttat    960
atatgtaagt ttatttatta taagtataca ttttatttat gtcagtttat taatatggat   1020
ttatttatag aaacattatc tgctattgat atttagtata aggcaaataa tatttatgac   1080
aataactatg gaaacaagat atcttaggct ttaataaaca catggatatc ataaaaaaaa   1140
aaaaaaaaaa aaaaaaagc ggccgc                                        1166
```

<210> SEQ ID NO 4
<211> LENGTH: 180
<212> TYPE: PRT
<213> ORGANISM: Mus musculus
<220> FEATURE:
<221> NAME/KEY: MISC_FEATURE
<222> LOCATION: (180)..(180)
<223> OTHER INFORMATION: Wherein Xaa is any amino acid

<400> SEQUENCE: 4

```
Met Ala Val Leu Gln Lys Ser Met Ser Phe Ser Leu Met Gly Thr Leu
1               5                   10                  15

Ala Ala Ser Cys Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Xaa
            180
```

<210> SEQ ID NO 5
<211> LENGTH: 27
<212> TYPE: DNA
<213> ORGANISM: Artificial
<220> FEATURE:
<223> OTHER INFORMATION: Description of Artificial Sequence:
      Oligonucleotide for generation of sense probe

<400> SEQUENCE: 5

```
aggatggaga catctgactg ccctacg                                        27
```

<210> SEQ ID NO 6
<211> LENGTH: 56
<212> TYPE: DNA
<213> ORGANISM: Artificial

```
<220> FEATURE:
<223> OTHER INFORMATION: Description of Artificial Sequence:
      Oligonucleotide for the generation of sense probe

<400> SEQUENCE: 6
gactgataat acgactcact atagggcgaa caattttgac tccgatattg tccaag        56

<210> SEQ ID NO 7
<211> LENGTH: 27
<212> TYPE: DNA
<213> ORGANISM: Artificial
<220> FEATURE:
<223> OTHER INFORMATION: Description of Artificial Sequence:
      Oligonucleotide for generation of anti-sense probe

<400> SEQUENCE: 7
acaattttga ctccgatatt gtccaag                                         27

<210> SEQ ID NO 8
<211> LENGTH: 56
<212> TYPE: DNA
<213> ORGANISM: Artificial
<220> FEATURE:
<223> OTHER INFORMATION: Description of Artificial Sequence:
      Oligonucleotide for generation of anti-sense probe

<400> SEQUENCE: 8
gactgataat acgactcact atagggcgaa ggatggagac atctgactgc cctacg         56

<210> SEQ ID NO 9
<211> LENGTH: 191
<212> TYPE: DNA
<213> ORGANISM: Artificial
<220> FEATURE:
<223> OTHER INFORMATION: Description of Artificial Sequence: Probe
      for IL-22 sequences

<400> SEQUENCE: 9
cagccataca tcgtcaaccg caccttatg ctggccaagg aggccagcct tgcagataac     60
aacacagatg tccggctcat cggggagaaa ctgttccgag gagtcagtgc taaggatcag   120
tgctacctga tgaagcaggt gctcaacttc accctggaag acgttctgct ccccagtca    180 gacaggttcc a                                                        191

<210> SEQ ID NO 10
<211> LENGTH: 49
<212> TYPE: PRT
<213> ORGANISM: Artificial
<220> FEATURE:
<223> OTHER INFORMATION: Description of Artificial Sequence:
      Amino acid tag

<400> SEQUENCE: 10

Met Lys Phe Leu Val Asn Val Ala Leu Val Phe Met Val Val Tyr Ile
1               5                   10                  15

Ser Tyr Ile Tyr Ala Gly Ser Gly His His His His His Gly Ser
            20                  25                  30

Gly Asp Tyr Lys Asp Asp Asp Lys Ala Pro Ile Ser Ser His Cys
        35                  40                  45

Arg
```

MONOCLONAL ANTIBODIES AGAINST INTERLEUKIN-22

CROSS-REFERENCE TO RELATED APPLICATIONS

This application is a continuation-in-part of application Ser. No. 10/084,298, filed Feb. 25, 2002 (now U.S. Pat. No. 6,939,545), which claims priority to U.S. provisional application No. 60/270,823, filed on Feb. 23, 2001, and U.S. provisional application No. 60/281,353, filed on Apr. 3, 2001. This application also claims the benefit of co-pending provisional application No. 60/480,652, filed on Jun. 23, 2003. The contents of all of these applications are hereby incorporated by reference in their entirety.

FIELD OF THE INVENTION

This invention relates to antibodies and antigen-binding fragments thereof that bind interleukin-22 (IL-22), in particular, human IL-22, and their uses in regulating IL-22-associated activities. The antibodies disclosed herein are useful in diagnosing, preventing, and/or treating IL-22-associated disorders, e.g., autoimmune disorders (e.g., arthritis).

BACKGROUND OF THE INVENTION

Interleukin-22 (IL-22) is a class II cytokine that shows sequence homology to IL-10. Its expression is up-regulated in T cells by IL-9 or ConA (Dumoutier L. et al. (2000) *Proc Natl Acad Sci* USA 97(18):10144-9). Further studies have shown that expression of IL-22 mRNA is induced in vivo in response to LPS administration, and that IL-22 modulates parameters indicative of an acute phase response (Dumoutier L. et al. (2000) supra; Pittman D. et al. (2001) *Genes and Immunity* 2:172). Taken together, these observations suggest that IL-22 plays a role in inflammation (Kotenko S. V. (2002) *Cytokine & Growth Factor Reviews* 13(3):223-40).

IL-22 is believed to bind to a receptor complex consisting of IL-22R and IL-10R2, two members of the type II cytokine receptor family (CRF2) (Xie M. H. et al. (2000) *J Biol Chem* 275(40):31335-9; Kotenko S. V. et al. (2001) *J Biol Chem* 276(4):2725-32). Both chains of the IL-22 receptor are expressed constitutively in a number of organs. Epithelial cell lines derived form these organs are responsive to IL-22 in vitro (Kotenko S. V. (2002) *Cytokine & Growth Factor Reviews* 13(3):22340). IL-22 induces activation of the JAK/STAT3 and ERK pathways, as well as intermediates of other MAPK pathways (Dumoutier L. et al. (2000) supra; Xie M. H. et al. (2000) supra; Dumoutier L. et al. (2000) *J Immunol* 164(4):1814-9; Kotenko S. V. et al. (2001) *J Biol Chem* 276 (4):2725-32; Lejeune, D. et al. (2002) *J Biol Chem* 277(37): 33676-82).

CRF2 members are receptors for IFNα/β, IFNγ, coagulation factor VIIa, IL-10 and the IL-0 related proteins IL-19, IL-20, IL-22, IL-24, as well as the recently identified IFN-like cytokines, IL-28 and IL-29 (Kotenko S. V. (2002) *Cytokine & Growth Factor Reviews* 13(3):223-40; Kotenko, S. V. et al. (2000) *Oncogene* 19(21):2557-65; Sheppard, P. et al. (2003) *Nature Immunology* 4(1):63-8; Kotenko, S. V. et al. (2003) *Nature Immunology* 4(1):69-77). In addition to these membrane receptors, the CRF2 family also includes a soluble protein, IL-22 binding protein (IL-22BP), which is specific for IL-22 and blocks its activity (Dumoutier, L. et al. (2001) *J Immunol* 166(12):7090-5; Kotenko, S. V. et al. (2001) *J Immunol* 166(12):7096-103; Xu, W. et al. (2001) *Proc Natl Acad Sci USA* 98(17):9511-6; Gruenberg, B. H. et al. (2001) *Genes & Immunity* 2(6):329-34; Wei C-C et al. (2003) *Genes & Immunity* 4:204-211). While the IL-22 receptor complex is unique for IL-22, however, each chain (i.e., IL-22R and IL-10R2) is shared with other CRF2 members to define functional receptors for IL-20, IL-24 (IL-22R/IL-20), IL28, IL29 (IFN-λR1/IL-10R2) and IL-10 (IL-1/IL-10R2) (Dumoutier, L. et al. (2001) *J. Immunol.* 167(7):3545-9; Wang, M. et al. (2002) *J Biol Chem* 277(9):7341-7; Parrish-Novak, J. et al. (2002) *J Biol Chem* 277(49):47517-23; Kotenko, S. V. et al. (1997) *EMBO J.* 16(19):5894-903; Spencer, S. D. et al. (1998) *J Exp Med* 187(4):571-8).

Both chains of the CRF2-composed receptor are necessary for signal transduction. One chain of the composed receptor has been historically defined as a ligand binding chain (e.g., IFNγR1) based on its high affinity for the cytokine. The other chain (e.g., IFNγR2) has been characterized as a helper or accessory chain, and shows minimal affinity for the cytokine alone (Kotenko, S. V. et al. (2000) *Oncogene* 19(21):2557-65). More recent results suggest that both receptor chains may contribute to the binding affinity, at least for IL-10 and IL-22 (Xie M. H. et al. (2000) *J Biol Chem* 275(40):31335-9; Kotenko S. V. et al. (2001) *J Biol Chem* 276(4):2725-32; Logsdon, N. J. et al. (2002) *J Interferon Cytokine Res* 22(11): 1099-112).

SUMMARY OF THE INVENTION

The present application provides, at least in part, IL22 binding agents such as antibodies and antigen-binding fragments thereof that bind to interleukin-22 ("IL-22"), in particular, human IL-22, with high affinity and specificity. The antibodies and antigen-binding fragments thereof of the present invention are also referred to herein as "anti-IL22 antibodies" and "fragments thereof," respectively. In one embodiment, the anti-IL22 antibody or fragment thereof is an IL-22 antagonist, and thus reduces, neutralizes, and/or antagonizes at least one IL-22-associated activity. For example, the anti-IL22 antibody or fragment thereof can bind to IL-22, e.g., an epitope of IL-22, and interfere with an interaction, e.g., binding, between IL-22 and an IL-22 receptor complex, e.g., a complex comprising IL-22 receptor ("IL-22R") and interleukin-10 receptor 2 ("IL-10R2"), or a subunit thereof (e.g., IL-22R or IL-10R2, individually). Thus, the antibodies and fragments thereof of the invention can be used to interfere with (e.g., inhibit, block or otherwise reduce) an interaction, e.g., binding, between IL-22 and an IL-22 receptor complex, or a subunit thereof.

In addition, Applicants have shown that administration of IL-22 in vivo induces parameters of an acute phase response, and that a reduction of IL-22 activity by using a neutralizing anti-IL-22 antibody ameliorates inflammatory symptoms in a mouse collagen-induced arthritis (CIA) model. Expression of IL-22 mRNA is upregulated in inflamed areas. Thus, IL-22 antagonists, e.g., neutralizing anti-IL-22 antibodies and fragments thereof, can be used to induce immune suppression in vivo. Accordingly, the anti-IL22 antibodies or fragments thereof of the invention are useful in diagnosing, treating and/or preventing IL-22-associated disorders, e.g., autoimmune disorders (e.g., multiple sclerosis, arthritic disorders such as rheumatoid arthritis); respiratory disorders (e.g., asthma, chronic obstructive pulmonary disease (COPD)); inflammatory conditions of, e.g., the skin (e.g., psoriasis), cardiovascular system (e.g., atherosclerosis), nervous system (e.g., Alzheimer's disease), kidneys (e.g., nephritis), liver (e.g., hepatitis) and pancreas (e.g., pancreatitis).

Accordingly, in one aspect, the invention features an isolated antibody or an antigen-binding fragment thereof, that interacts with, e.g., binds to, IL-22, in particular, mammalian IL-22, e.g., human or murine IL-22. In one embodiment, the antibody or fragment thereof is a neutralizing antibody, e.g., it reduces or inhibits one or more IL-22-associated activities, e.g., chemokine secretion (e.g., GRO1 secretion); an acute phase response, phosphorylation of a kinase, e.g., STAT protein (e.g., STAT-3 protein), cell proliferation (e.g., HEPG2 proliferation and/or phosphorylation), among others. Anti-IL-22 antibodies or fragments thereof can bind to IL-22 with high affinity, e.g., with an affinity constant (Kd) of less than $10E^{-7}$ M, preferably $10E^{-8}$, $10E^{-9}$, $10E^{-10}$, more preferably, $10E^{-11}$ M or higher affinity. In other embodiments, the anti-IL-22 antibodies or fragments thereof can neutralize one or more IL-22-associated activities with an $ED_{50}$ of at least about 60 nM, typically about 5 nM to 200 pM or stronger. In other embodiments, the anti-IL22 antibodies or fragments thereof associate with IL22 with kinetics in the range of $10E^3$ to $10E^7$ 1/Ms, typically $10E^4$ to $10E^6$ 1/Ms. In yet another embodiment, the anti-IL22 antibodies or fragments thereof have dissociation kinetics in the range of $10E^{-2}$ to $10E^{-6}$ 1/s, typically $10E^{-3}$ to $10E^{-6}$ 1/s. In one embodiment, the anti-IL22 antibodies or fragments thereof bind to IL-22, e.g., human IL-22, with an affinity and/or kinetics similar to monoclonal antibody Ab-04 produced by a hybridoma cell line having ATCC accession number PTA-5255; or Ab-02 produced by a hybridoma cell line having ATCC accession number PTA-5254. The affinity of the anti-IL-22 antibody or fragment thereof can be tested using, e.g., biosensor technology (Biacore) (see Examples 5 and 22 below). The inhibitory activities of the anti-IL22 antibodies ($ED_{50}$) can be tested using, e.g., a STAT phosphorylation assay of HEPG2 cells or BaF3 proliferation assay as described herein (see e.g., Examples 20-21).

In one embodiment, the anti-IL22 antibody or fragment thereof (e.g., an Fab, F(ab')$_2$, Fv or a single chain Fv fragment) is a monoclonal or single specificity antibody. The antibody or fragment thereof can also be a human, humanized, CDR-grafted, chimeric, or in vitro generated antibody. In yet other embodiments, the antibody has a heavy chain constant region chosen from, e.g., IgG1, IgG2, IgG3, IgG4, IgM, IgA1, IgA2, IgD, and IgE; more particularly, chosen from, e.g., IgG1, IgG2, IgG3, and IgG4. In another embodiment, the antibody has a light chain chosen from, e.g., kappa or lambda.

In another embodiment, the anti-IL22 antibody or fragment thereof, specifically binds to IL-22, in particular, mammalian, e.g., human IL-22 (e.g., human IL-22 having an amino acid sequence of SEQ ID NO:2, or mature human IL-22 sequence from about amino acids 34-179 of SEQ ID NO:2, or a sequence that is at least 85%, 90%, 95%, 99% or more identical thereto). In other embodiments, the antibody or fragment thereof specifically binds to a fragment of IL-22, e.g., a fragment of at least 10, 20, 50, 75, 100, 150, or 170 amino acids contiguous to the amino acid sequence set forth in SEQ ID NO:2, or a sequence that is at least 85%, 90%, 95%, 99% or more identical thereto. In one embodiment, the anti-IL22 antibody or fragment thereof specifically binds to human IL-22 and does not cross-react with IL-22 from non-human species, e.g., murine (e.g., mouse or rat) IL-22. In other embodiments, the anti-IL22 antibody or fragment thereof binds to two or more forms mammalian IL-22, e.g., human and murine (e.g., mouse or rat) IL-22.

In one embodiment, the anti-IL22 antibody or fragment thereof, specifically binds to an epitope, e.g., a linear or a conformational epitope, of IL-22, e.g., in particular, mammalian, e.g., human or murine IL-22. In another embodiment, the anti-IL22 antibody or fragment thereof, binds to a complex chosen from, e.g., IL-22 and IL-22R ("IL-22/IL-22R"), IL-22 and IL-10R2 ("IL-22/IL-10R2"), and IL-22, IL-22R, and IL-10R2 ("IL-22/IL-22R/IL-10R2"). In one embodiment, the anti-IL22 antibody or fragment thereof binds to a complex of IL-22 and an IL-22R, thereby forming a complex of the anti-IL22 antibody or fragment thereof, IL-22 and IL-22R. Binding of the anti-IL22 antibody or fragment thereof can increase the stability of the complex, and thus interfere with an interaction of the complex with IL-10R2.

In other embodiments, the antibody or fragment thereof, binds to IL-22, and interferes with (e.g., inhibits, blocks or otherwise reduces) an interaction, e.g., binding, between IL-22 and an IL-22 receptor complex, e.g., a complex comprising IL-22R and IL-10R2. In other embodiments, the anti-IL22 antibody or fragment thereof, binds to IL-22, and interferes with (e.g., inhibits, blocks or otherwise reduces) an interaction, e.g., binding, between IL-22 and a subunit of the IL-22 receptor complex, e.g., IL-22R or IL-10R2, individually. In yet another embodiment, the anti-IL22 antibody or fragment thereof, binds to IL-22, and interferes with (e.g., inhibits, blocks or otherwise reduces) an interaction, e.g., binding, between a complex of IL-22 and IL-22R ("IL-22/IL-22R"), and IL-10R2. In another embodiment, the anti-IL22 antibody or fragment thereof, binds to IL-22, and interferes with (e.g., inhibits, blocks or otherwise reduces) an interaction, e.g., binding, between a complex of IL-22 and IL-10R2 ("IL-22/IL-10R2"), and IL-22R.

In another embodiment, the anti-IL22 antibody or fragment thereof competes with an IL-22 binding protein (IL-22BP), e.g., a mammalian IL-22BP (e.g., a human or murine IL-22BP) for binding to IL-22, e.g., a mammalian IL-22 (e.g., a human or murine IL-22).

A non-limiting example of an anti-IL22 antibody that interferes with IL-22 binding to IL-22R is "Ab-04." Ab-04 (also referred to herein as rat monoclonal antibody "P3/2") binds to human IL-22 and neutralizes at least one IL-22 activity (see Example 5, 16, 17, 20 and 21). A hybridoma cell line producing Ab-04 was deposited with the ATCC on Jun. 5, 2003 and has been assigned ATCC accession number PTA-5255. Another non-limiting example of an anti-IL22 antibody, which interferes with IL-22 binding to IL-10R2 is "Ab-02." Ab-02 (also referred to herein as rat monoclonal antibody "P3/3") binds to mouse and human IL-22 and neutralizes at least one IL-22 activity (see Example 5, 16, 17, 20, and 21). A hybridoma cell line producing Ab-02 was deposited with the ATCC on Jun. 5, 2003 and has been assigned ATCC accession number PTA-5254.

In one embodiment, the antibody or fragment thereof binds specifically to IL-22, e.g., murine or human IL-22, and competitively inhibits the binding of a second antibody to IL-22, e.g., to a target epitope on IL-22 (e.g., human or murine IL-22). The second antibody can be a monoclonal antibody produced by a hybridoma chosen from, e.g., PTA-5254 and PTA-5255. In another embodiment, the antibody or fragment thereof comprises at least one antigen-binding region, e.g., a variable region, from a monoclonal antibody produced by a hybridoma chosen from, e.g., PTA-5254 and PTA-5255. In yet another embodiment, the antibody or fragment thereof comprises at least one, two, three or four variable regions from a monoclonal antibody produced by a hybridoma chosen from, e.g., PTA-5254 and PTA-5255. In another embodiment, the antibody or fragment thereof comprises at least one or two heavy chain variable regions from a monoclonal antibody produced by a hybridoma chosen from, e.g., PTA-5254 and PTA-5255. In another embodiment, the antibody or fragment thereof comprises at least one or two light chain variable regions from a monoclonal antibody produced by a hybridoma chosen from, e.g., PTA-5254 and PTA-5255. In yet another embodiment, the antibody or fragment thereof comprises at least one, two, or three complementarity determining regions (CDR's) from a heavy chain variable region of a monoclonal antibody produced by a hybridoma chosen from, e.g., PTA-5254 and PTA-5255. In yet another embodiment, the antibody or fragment thereof comprises at least one, two, or three CDR's from a light chain variable region of a monoclonal antibody produced by a hybridoma chosen from, e.g., PTA-5254 and PTA-5255. In yet another embodiment, the antibody or fragment thereof comprises at least one, two, three, four, five or six CDR's from a heavy chain and light chain variable regions of a monoclonal antibody produced by a hybridoma chosen from, e.g., PTA-5254 and PTA-5255. In another embodiment, the monoclonal antibody is produced by a hybridoma chosen from, e.g., PTA-5254 and PTA-5255.

The anti-IL22 antibody or fragment thereof described herein, can be derivatized or linked to another functional molecule, e.g., another peptide or protein (e.g., an Fab' fragment). For example, the fusion protein or an antibody, or antigen-binding portion, can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

In yet another embodiment, the IL-22 binding agent, e.g., the IL22 antagonist, (e.g., the anti-IL22 antibody or fragment thereof described herein), or a pharmaceutical composition thereof, is administered alone or in combination therapy, i.e., combined with other agents, e.g., therapeutic agents, which are useful for treating IL-22-associated disorders. Examples of IL-22-associated disorders include, but are not limited to, a disorder chosen from one or more of: autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, vasculitis, multiple sclerosis, autoimmune thyroiditis, dermatitis (including atopic dermatitis and eczematous dermatitis), myasthenia gravis, inflammatory bowel disease (IBD), Crohn's disease, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); septicemia; transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

The combination therapy can include one or more IL22 binding agents, e.g., IL-22 antagonists, (e.g., anti-IL22 antibodies or fragments thereof), co-formulated with, and/or co-administered with, one or more additional therapeutic agents, e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more detail herein.

Examples of preferred additional therapeutic agents that can be co-administered and/or co-formulated with one or more IL22 binding agents, e.g., IL-22 antagonists, (e.g., anti-IL22 antibodies or fragments thereof), include, but are not limited to, one or more of: TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™), p55 kD TNF receptor-IgG fusion protein; TNF enzyme antagonists, e.g., TNFα converting enzyme (TACE) inhibitors); antagonists of IL-12, IL-15, IL-17, IL-18, IL-21/IL-21R; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Examples of preferred additional therapeutic agents that can be co-administered and/or co-formulated with one or more anti-IL-22 antibodies or fragments thereof include one or more of: a soluble fragment of a TNF receptor, e.g., p55 or p75 human TNF receptor or derivatives thereof, e.g., 75 kdT-NFR-IgG (75 kD TNF receptor-IgG fusion protein, Enbrel™); methotrexate, leflunomide, or a sirolimus (rapamycin) or an analog thereof, e.g., CCI-779.

Without being bound by theory, Applicants believe that IL-22 exerts its inflammatory effects locally, e.g., by acting as an amplifier or a regulator of tissue inflammation as opposed to systemic inflammation. Accordingly, inhibition of IL-22 activity using, e.g., an anti-IL22 antibody or fragment thereof described herein, may provide a more effective tissue-specific, anti-inflammatory activity than systemic anti-inflammatory modalities. Furthermore, inhibition of local IL-22 activity using, e.g., an anti-IL22 antibody or fragment thereof described herein, may provide a useful candidate for combination with systemic anti-inflammatory modalities.

In another aspect, the invention provides compositions, e.g., pharmaceutical compositions, which include a pharmaceutically acceptable carrier and at least one IL-22 binding agent, e.g., an IL22 antagonist, (e.g., anti-IL22 antibody or fragment thereof described herein). In one embodiment, the compositions, e.g., pharmaceutical compositions, comprise a combination of two or more one of the aforesaid IL-22 binding agents, e.g., anti-IL22 antibodies or fragments thereof. Combinations of the IL-22 antagonist, e.g., the anti-IL22 antibody or fragment thereof, and a drug, e.g., a therapeutic agent (e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more herein) are also within the scope of the invention.

The epitope of IL-22, e.g., human IL-22, recognized by Ab-02 or Ab-04 is also within the scope of the present invention.

In another aspect, the invention features a method of decreasing, inhibiting or reducing an acute phase response in a subject. The method includes administering to the subject an IL22 binding agent, e.g., an IL-22 antagonist, (e.g., an anti-IL-22 antibody or fragment thereof as described herein), in an amount sufficient to decrease, inhibit or reduce the acute phase response in the subject. In one embodiment, the subject is a mammal, e.g., a human suffering from an IL-22-associated disorder, including, e.g., respiratory disorders, inflammatory disorders and autoimmune disorders. In one embodiment, the IL-22 binding agent is administered locally, e.g., topically, subcutaneously, or other administrations that are not in the general circulation.

In another aspect, the invention features a method of modulating, e.g., interfering with (e.g., inhibiting, blocking or otherwise reducing), an interaction, e.g., binding, between IL-22 and an IL-22 receptor complex, or a subunit thereof, e.g., IL-22R or IL-10R2, individually. The method comprises, optionally, providing IL-22 and an IL-22 receptor complex or a subunit thereof (e.g., a soluble IL-22 receptor complex or subunit thereof, or a membrane-associated IL-22 receptor complex or subunit thereof, e.g., a cell expressing an IL-22 receptor complex or a subunit thereof); contacting IL-22 with the IL22 receptor complex or subunit thereof, under conditions that allow an interaction between IL-22 and the IL-22 receptor complex or subunit thereof to occur to thereby form an IL-22/IL-22 receptor mixture; and contacting the IL-22/IL-22 receptor mixture with at least one IL-22 binding agent, e.g., at least one anti-IL-22 antibody or fragment thereof, e.g., at least one anti-IL-22 antibody or fragment thereof as described herein, thereby modulating, e.g., interfering with (e.g., inhibiting, blocking or otherwise reducing), the interaction.

The subject method can be used on cells in vitro (e.g., in a cell-free system), in culture, e.g. in vitro or ex vivo. For example, IL-22 receptor-expressing cells can be cultured in vitro in culture medium and the contacting step can be effected by adding one or more anti-IL-22 antibodies or fragments thereof, e.g., anti-IL-22 antibodies or fragments thereof as described herein, to the culture medium. Alternatively, the method can be performed on cells present in a subject, e.g., as part of an in vivo (e.g., therapeutic or prophylactic) protocol.

In another aspect, the invention features a method of treating (e.g., curing, suppressing, ameliorating, delaying or preventing the onset of, or preventing recurrence or relapse of) or preventing an IL22-associated disorder, in a subject. The method includes: administering to the subject an IL22 binding agent, e.g., an IL-22 antagonist, (e.g., an anti-IL22 antibody or fragment thereof as described herein), in an amount sufficient to treat or prevent the IL22-associated disorder. In one embodiment, the IL-22 binding agent is administered locally, e.g., topically, subcutaneously, or other administrations that are not in the general circulation.

The IL-22 binding agent, e.g., IL-22 antagonist, (e.g., the anti-IL22 antibody or fragment thereof), can be administered to the subject, alone or in combination, with other therapeutic modalities as described herein. In one embodiment, the subject is a mammal, e.g., a human suffering from an IL-22-associated disorder, including, e.g., respiratory disorders, inflammatory disorders and autoimmune disorders.

Examples of IL-22-associated disorders include, but are not limited to, a disorder chosen from one or more of: autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, vasculitis, multiple sclerosis, autoimmune thyroiditis, dermatitis (including atopic dermatitis and eczematous dermatitis), myasthenia gravis, inflammatory bowel disease (IBD), Crohn's disease, diabetes mellitus (type I); cardiovascular disorders, e.g., cholesterol metabolic disorders, oxygen free radical injury, ischemia, atherosclerosis; disorders associated with wound healing; respiratory disorders, e.g., asthma and COPD (e.g., cystic fibrosis); inflammatory disorders of the skin, e.g., psoriasis, liver (e.g., hepatitis), kidney (e.g., nephritis) and pancreas (e.g., pancreatitis); septicemia; transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis (preferably, rheumatoid arthritis); a respiratory disorder (e.g., asthma, chronic obstructive pulmonary disease (COPD); and an inflammatory condition of, e.g., skin (e.g., psoriasis), liver (e.g., hepatitis), kidney (e.g., nephritis) and pancreas (e.g., pancreatitis).

In other embodiments, the invention provides a method of treating (e.g., reducing, ameliorating) or preventing one or more symptoms associated with arthritis (e.g., rheumatoid arthritis) in a subject. The method comprises administering to the subject an IL-22 binding agent, e.g., an IL22 antagonist, (e.g., an IL-22 antibody or a fragment thereof), in an amount sufficient to treat (e.g., reduce, ameliorate) or prevent one or more arthritic symptoms. The IL-22 antibody can be administered therapeutically or prophylactically, or both. The IL-22 binding agent, e.g., IL22 antagonist, e.g., the anti-IL22 antibody or fragment thereof, can be administered to the subject, alone or in combination, with other therapeutic modalities as described herein. Preferably, the subject is a mammal, e.g., a human suffering from an IL-22-associated disorder as described herein.

In another aspect, the invention provides a method for detecting the presence of IL-22 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-IL22 antibody or fragment thereof as described herein; and (ii) detecting formation of a complex between the anti-IL22 antibody or fragment thereof, and the sample or the control sample, wherein a statistically significant change in the formation of the complex in the sample relative to the control sample is indicative of the presence of the IL-22 in the sample.

In yet another aspect, the invention provides a method for detecting the presence of IL-22 in vivo (e.g., in vivo imaging in a subject). The subject method can be used to diagnose a disorder, e.g., an IL-22-associated disorder. The method includes: (i) administering the anti-IL22 antibody or fragment thereof as described herein to a subject or a control subject under conditions that allow binding of the antibody or fragment to IL-22; and (ii) detecting formation of a complex between the antibody or fragment and IL-22, wherein a statistically significant change in the formation of the complex in the subject relative to the control subject is indicative of the presence of IL-22.

Preferably, the antibody or fragment thereof is directly or indirectly labeled with a detectable substance to facilitate detection of the bound or unbound antibody. Suitable detectable substances include various enzymes, prosthetic groups, fluorescent materials, luminescent materials and radioactive materials.

Methods for delivering or targeting an agent, e.g., a therapeutic or a cytotoxic agent, to an IL-22-expressing cell in vivo are also disclosed.

Kits comprising the IL22 binding agents, e.g., IL22 antagonists, (e.g., the anti-IL22 antibodies or fragment thereof), of the invention for therapeutic and diagnostic uses are also within the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 6A is a linear graph showing that bio-IL-22 binds to the immobilized IL-22R-Fc, and not detectably to IL-10R2-Fc. The results from the reverse binding experiment are graphically depicted in FIG. 6B. Soluble IL-22R-Fc, and not IL-10R2-Fc, binds to immobilized bio-IL-22. These results indicate that there is a relatively strong interaction between IL-22 and IL-22R, while IL-10R2-Fc has only a slight avidity for IL-22.

FIG. 7A is a panel of Western blots depicting conditioned media from CHO cells expressing either IL-22R-Fc, IL-10R2-Fc or both receptor Fc were separated on SDS-PAGE gels under both reduced (+□ME) and non-reduced (-□ME) conditions. The SDS-PAGE gels were blotted to a membrane, which was then probed with polyclonal antibodies directed against either human IgG Fc, IL-22R or IL-10R2. Under reducing conditions (+βME, FIG. 7A), IL-22R and IL10R2-Fc CHO lines secrete a human Fc fusion protein with molecular weights of ~60 kD species is IL-22R-Fc while the ~85 kD species is IL-10R2-Fc. FIG. 7B is a linear graph depicting the results from an ELISA using conditioned media from CHO cells expressing either IL-22R-Fc (■), IL-10R2-Fc (○) or both (▲). The ELISA plates were coated with rabbit anti-human IL-22R antibody. A 1:1 mixture of the two homodimers was also added as a control (Δ). The bound receptors were detected using a biotinylated goat anti-human IL-10R2 antibody, followed by streptavidin-HRP. The results shown in FIGS. 7A-7B indicate that the receptor Fc fusions are secreted from CHO cells as homodimers and heterodimers. The IL-22R/IL-10R2-Fc co-expressing CHO cells secrete mostly heterodimer and IL-10R2-Fc homodimer.

In FIG. 8A, 50 ng/ml of total Fc from CHO CM expressing either IL-22R-Fc (■), IL-10R2-Fc (○) or both IL-22R-Fc and IL-10R2-Fc (▲) was captured onto anti-human IgG coated wells. Bio-IL-22 was then added to the wells at various concentrations. Bound bio-IL-22 was subsequently detected using streptavidin-HRP. In FIG. 8B, various concentrations of the following total Fc were captured onto anti-human IgG coated wells from a 1:1 mixture of either IL-22R-Fc CM and irrelevant Fc protein (■), IL-22R-Fc CM and IL-10R2-Fc CM (Δ) or IL-22R-Fc/IL-10R2-Fc CM from co-expressed cells and control Fc protein (▲). Bio-IL-22 (30 ng/ml) was then added to the wells. Bound bio-IL-22 was subsequently detected using streptavidin-HRP. The results shown in FIGS. 8A-8B indicate that the ECD of IL-22R is required for the detection of IL-10R2's role in IL-22 binding. Enhanced binding of IL-22 is detected when both ECD are present.

FIG. 9A is a linear graph depicting the results from an ELISA using IL-22R-Fc from CM captured onto anti-human IgG coated wells. Bio-IL-22 was then and subsequently detected using streptavidin-HRP (broken line). Various concentrations of IL-10R2-Fc and biotinylated IL-22 were also added together and then bound bio-IL-22 detected (♦). Various concentrations of IL-10R2-Fc from CM were also added first, and then bio-IL-22 subsequently added to the wells and bound bio-IL-22 detected (◇). In FIG. 9B, fifty ng/ml of IL-22R-Fc from CM was captured onto anti-human IgG coated wells. Bio-IL-22 was then added to the wells. Bound bio-IL-22 was then detected immediately after, using streptavidin-HRP (solid line). Bound bio-IL-22 was also detected after an additional 1 hour incubation with either PBS-1% BSA (broken line) or various concentrations of IL-10R2-Fc (•). The results shown herein indicate that binding to IL-10R2 requires an interaction between IL-22 and IL-22R prior to its roles in enhancing IL-22 binding.

In FIG. 10A, serially diluted antibody was pre-incubated with a fixed concentration of IL-22 in cell media. This media, including IL-22 complexed with antibody, was then applied to HEPG2 cells. Cell lysates were subsequently prepared, protein separated by gel electrophoresis, blotted and then probed with an antibody specific for P-STAT3. Cells incubated with IL-22 alone (+) or without IL-22 (-) were included as positive and negative control, respectively. Both of these antibodies are able to block IL-22's activity on cells: with increasing concentration of antibody, the detection of P-STAT3 decreases. In FIG. 10B, fifty ng/ml of IL-22R-Fc from CM was captured onto anti-human IgG coated wells. Biotinylated IL-22 (30 ng/ml) was pre-incubated alone (broken line) or with various concentrations of Ab-02 (•), Ab-04 (▲), anti-IL-10R2 (+) or control antibody (-) for 30 minutes and then added to wells with the immobilized IL-22R-Fc. Bound biotinylated IL-22 was subsequently detected using streptavidin-HRP. (C) Fifty ng/ml of total Fc in CM from CHO cells expressing both IL-22R-Fc and IL-10R2-Fc was incubated in anti-human IgG coated wells. Biotinylated IL-22 (5 ng/ml) was pre-incubated alone (broken line) or with various concentrations of Ab-02 (•), Ab-04 (▲), anti-IL-10R2 (+) or control antibody (-) for 30 minutes and then added to wells with the immobilized IL-22R-Fc/IL-10R2-Fc. Bound biotinylated IL-22 was subsequently detected using streptavidin-HRP. These results show that both Ab-02 and Ab-04 neutralize IL-22 activity. Ab-04 blocks an interaction between IL-22 and IL-22R, and Ab-02 blocks an interaction between IL-22 and IL-10R2.

In FIG. 11A, fifty ng/ml of IL-22R-Fc from CM was captured onto anti-human IgG coated wells. Biotinylated IL-22 (30 ng/ml) was pre-incubated alone (broken line) or with various concentrations of IL-22BP-Fc ( ) for 30 minutes and then added to wells with the immobilized IL-22R-Fc. Bound biotinylated IL-22 was subsequently detected using streptavidin-HRP. Background is represented by dashed line. In FIG. 11B, fifty ng/ml of total Fc in CM from CHO cells expressing both IL-22R-Fc and IL-10R2-Fc was incubated in anti-human IgG coated wells. Biotinylated IL-22 (5 ng/ml) was pre-incubated alone (broken line) or with various concentrations of IL-22BP-Fc ( ) for 30 minutes and then added to wells with the immobilized IL-22R-Fc/IL-10R2-Fc. Bound biotinylated IL-22 was subsequently detected using streptavidin-HRP. In FIG. 11C, fifty ng/ml of IL-22BP-Fc in CM was incubated in anti-human IgG coated wells. Biotinylated IL-22 (1 ng/ml) was pre-incubated alone (broken line) or with various concentrations of Ab-02 (•) or Ab-04 (▲) or a control rat antibody (−) for 30 minutes and then added to wells with the immobilized IL-22BP-Fc. Bound biotinylated IL-22 was subsequently detected using streptavidin-HRP. FIGS. 11A-11C shows that IL-22BP inhibits IL-22 activity in a similar fashion as Ab-04, while Ab-02 is distinct.

DETAILED DESCRIPTION OF THE INVENTION

Figure 1:
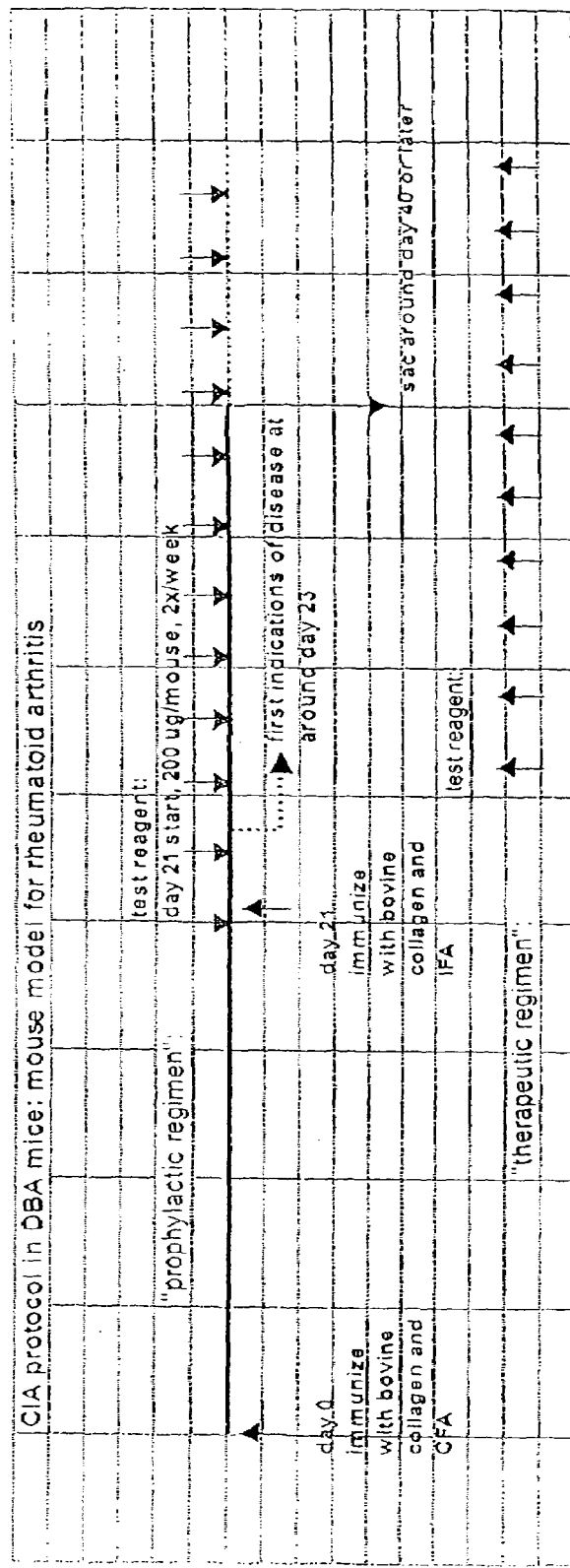
FIG. 1 is a schematic drawing showing an experimental protocol used to analyze the effect of an IL-22 antibody on an in vivo murine arthritis model.

Interleukin 22 ("IL-22") is a cytokine induced during innate and adaptive immune responses. When administered to a subject, it induces an acute phase response, implicating a role for IL-22 in mechanisms of inflammation. The receptor chains that together with IL-22 form a signaling complex are IL-22 receptor ("IL-22R") and IL-10 receptor 2 ("IL-10R2"), two members of the type II cytokine receptor family. In one embodiment, Applicants have characterized an interaction between these proteins in an ELISA based format using biotinylated cytokine and receptor extracellular domain (ECD) Fc fusion dimers. Applicants have shown that IL-22 has measurable affinity for the ECD of IL-22R and no detectable affinity for IL-10R2 alone (Example 12). IL-22 has a substantially greater affinity for IL-22R/IL-10R2 ECD presented as Fc heterodimers (Example 13). Further analyses involving temporal additions suggest that IL-10R2 binds to a surface created by the association between IL-22 and IL-22R. Applicants believe that IL-10R2 ECD further stabilizes the association of IL-22 within its cytokine receptor complex (Examples 14 and 15). In other embodiments, neutralizing anti-IL-22 antibodies have been generated and characterized in terms of their binding specificity, affinity and IL-22 neutralizing activity (Examples 5, 16, 17, 20, 21 and 22). In one embodiment, a neutralizing rat IL-22 antibody and IL-22BP (a secreted IL-22-binding protein and natural antagonist of the same), both define an IL-22 epitope that may be directly required for IL-22R ECD recognition. In yet another embodiment, a rat monoclonal antibody defines a separate IL-22 region important for the role of the IL-10R2 ECD. In addition, Applicants have shown that administration of IL-22 in vivo induces parameters of an acute phase response, and that a reduction of IL-22 activity by using a neutralizing anti-IL-22 antibody ameliorates inflammatory symptoms in a mouse collagen-induced arthritis (CIA) model (Example 9). Expression of IL-22 mRNA is upregulated in inflamed areas. Thus, IL-22 antagonists, e.g., neutralizing anti-IL-22 antibodies and fragments thereof, can be used to induce immune suppression in vivo.

Accordingly, the present application provides, at least in part, antibodies and antigen-binding fragments thereof that bind to IL-22, in particular, human IL-22, with high affinity and specificity. In one embodiment, the anti-IL22 antibody or fragment thereof reduces, inhibits or antagonizes at least one IL-22-associated activity. For example, the anti-IL22 antibody or fragment thereof can bind to IL-22, e.g., an epitope of IL-22, and interfere with an interaction, e.g., binding, between IL-22 and an IL-22 receptor complex, e.g., a complex comprising IL-22 receptor ("IL-22R") and interleukin-10 receptor 2 ("IL-10R2"), or a subunit thereof (e.g., IL-22R or IL-10R2, individually). Thus, the antibodies and fragments thereof of the invention can be used to interfere with (e.g., inhibit, block or otherwise reduce) an interaction, e.g., binding, between IL-22 and an IL-22 receptor complex, or a subunit thereof. Thus, the anti-IL22 antibodies or fragments thereof of the invention can be used to diagnose, treat or prevent IL-22-associated disorders, e.g., autoimmune disorders, e.g., arthritic disorders (e.g., rheumatoid arthritis); respiratory disorders (e.g., asthma, chronic obstructive pulmonary disease (COPD); and inflammatory conditions of, e.g., skin (e.g., psoriasis), liver (e.g., hepatitis), kidney (e.g., nephritis) and pancreas (e.g., pancreatitis).

In order that the present invention may be more readily understood, certain terms are first defined. Additional definitions are set forth throughout the detailed description.

The term "interleukin-22" or "IL-22," as used herein, refers to class 2 cytokine that shows homology to IL-10, and is up-regulated in T cells by IL-9 or ConA (Dumoutier L. et al. (2000) *Proc Natl Acad Sci USA* 97(18): 10144-9). IL-22 is a cytokine whose expression is stimulated by LPS, but not significantly by IFN-γ. IL-22 is produced predominantly by activated human and mouse Th1, but not Th2, CD4+ cells. IL-22 modulates parameters indicative of an acute phase response (Dumoutier L. et al. (2000) supra; Pittman D. et al. (2001) *Genes and Immunity* 2:172; WO 00/65027; Gabay, C. (1999) *New England Journal of Medicine* 340(6):448454)

and inflammation (Kotenko S. V. (2002) *Cytokine & Growth Factor Reviews* 13(3):22340; WO 00/65027). IL-22 is believed to bind to a receptor complex consisting of IL-22 receptor (also referred to herein as "IL-22R") and IL-10 receptor 2 (also referred to herein as "IL-10R2"), two members of the type II cytokine receptor family (CRF2). The nucleotide and amino acid sequences for these two receptors are described in Xie M. H. et al. (2000) *J Biol Chem* 275(40): 31335-9 (human IL-22R); Kotenko S. V. et al. (2001) *J Biol Chem* 276(4):2725-32 (human IL-10R2). Both chains of the IL-22 receptor are expressed constitutively in a number of organs. Epithelial cell lines derived form these organs are responsive to IL-22 in vitro (Kotenko S. V. (2002) *Cytokine & Growth Factor Reviews* 13(3):223-40). IL-22 induces activation of the JAK/STAT3 and ERK pathways, as well as intermediates of other MAPK pathways ((Dumoutier L. et al. (2000) supra; Xie M. H. et al. (2000) supra; Dumoutier L. et al. (2000) *J Immunol* 164(4): 1814-9); Kotenko S. V. et al. (2001) *J Biol Chem* 276(4):2725-32; Lejeune, D. et al. (2002) *J Biol Chem* 277(37):33676-82). The contents of these references are hereby expressly incorporated by reference in their entirety.

Accordingly, the term "IL-22" refers to a cytokine (preferably of mammalian, e.g., murine or human origin) which is capable of interacting with, e.g., binding to, an IL-22 receptor, e.g., IL-22R or IL-10R2, or a complex thereof (preferably of mammalian, e.g., murine or human, origin) and having one of the following features: (i) an amino acid sequence of a naturally occurring mammalian IL-22 polypeptide or a fragment thereof, e.g., an amino acid sequence shown as SEQ ID NO:2 (human) or SEQ ID NO:4 (murine) or a fragment thereof; (ii) an amino acid sequence substantially homologous to, e.g., at least 85%, 90%, 95%, 98%, 99% homologous to, an amino acid sequence shown as SEQ ID NO:2 (human) or SEQ ID NO:4 (murine) or a fragment thereof; (iii) an amino acid sequence which is encoded by a naturally occurring mammalian IL-22 nucleotide sequence or a fragment thereof (e.g., SEQ ID NO:1 (human) or SEQ ID NO:3 (murine) or a fragment thereof); (iv) an amino acid sequence encoded by a nucleotide sequence which is substantially homologous to, e.g., at least 85%, 90%, 95%, 98%, 99% homologous to, a nucleotide sequence shown as SEQ ID NO:1 (human) or SEQ ID NO:3 (murine) or a fragment thereof; (v) an amino acid sequence encoded by a nucleotide sequence degenerate to a naturally occurring IL-22 nucleotide sequence or a fragment thereof, e.g., SEQ ID NO:1 (human) or SEQ ID NO:3 (murine) or a fragment thereof; or (vi) a nucleotide sequence that hybridizes to one of the foregoing nucleotide sequence sequences under stringent conditions, e.g., highly stringent conditions. Preferably, the IL-22 polypeptide has one or more IL-22 associated activities, e.g., an activity as described herein.

The human IL-22 cDNA was deposited with the American Type Culture Collection (10801 University Boulevard, Manassas, Va., U.S.A. 20110-2209) on Apr. 28, 1999 as an original deposit under the Budapest Treaty and were given the accession number ATCC 207231. All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

The phrase "an IL-22 associated activity" refers to one or more of the biological activities of an IL-22 polypeptide, e.g., a mature IL-22 polypeptide (e.g., a mammalian, e.g., human or murine IL-22 having an amino acid sequence as shown in SEQ ID NO:2 and 4, respectively), including, but not limited to, (1) interacting with, e.g., binding to, an IL-22 receptor (e.g., an IL-22R or IL-10R2 or a complex thereof, preferably of mammalian, e.g., murine or human origin); (2) associating with one or more signal transduction molecules; (3) stimulating phosphorylation and/or activation of a protein kinase, e.g., JAK/STAT3, ERK, and MAPK; (4) modulating, e.g., stimulating or decreasing, proliferation, differentiation, effector cell function, cytolytic activity, cytokine or chemokine secretion, and/or survival of an IL-22 responsive cell, e.g., an epithelial cell from, e.g., kidney, liver, colon, small intestine, thyroid gland, pancreas, skin); (5) modulating at least one parameter of an acute phase response, e.g., a metabolic, hepatic, hematopoietic (e.g., anemia, platelet increase) or neuroendocrine change, or a change (e.g., increase or decrease in an acute phase protein, e.g., an increase in fibrinogen and/or serum amyloid A, or a decrease in albumin); and/or (6) modulating at least one parameter of an inflammatory state, e.g., modulating cytokine-mediated proinflammatory actions (e.g., fever, and/or prostaglandin synthesis, for example $PGE_2$ synthesis), modulating cellular immune responses, modulating cytokine, chemokine (e.g., GRO1) or lymphokine production and/or secretion (e.g., production and/or secretion of a proinflammatory cytokine).

The term "acute phase response" is recognized in the art, see e.g., Gabay, C. (1999) *New England Journal of Medicine* 340(6):448454).

As used herein, a "therapeutically effective amount" of an IL-22 antagonist, e.g., antibody, refers to an amount of an agent which is effective, upon single or multiple dose administration to a subject, e.g., a human patient, at curing, reducing the severity of, ameliorating one or more symptoms of a disorder, or in prolonging the survival of the subject beyond that expected in the absence of such treatment.

As used herein, "a prophylactically effective amount" of an IL-22 antagonist, e.g., antibody, refers to an amount of an agent which is effective, upon single- or multiple-dose administration to a subject, e.g., a human patient, in preventing or delaying the occurrence of the onset or recurrence of a disorder, e.g., a disorder as described herein.

The term "induce", "reduce," "inhibit," "potentiate," "elevate," "increase," "decrease" or the like, e.g., which denote quantitative differences between two states, refer to at least statistically significant differences between the two states.

As used herein, an "IL-22 antagonist" refers to an agent which reduces, inhibits or otherwise diminishes one or biological activities of an IL-22 polypeptide, e.g., a human IL-22 polypeptide, or fragment thereof. Preferably, the antagonist interacts with, e.g., binds to, an IL-22 polypeptide. Antagonism using an IL-22 antagonist does not necessarily indicate a total elimination of the IL-22-associated biological activity. IL-22 antagonists include without limitation antibodies directed to human IL-22 proteins; soluble forms of the receptor or other target to which human IL-22 is directed; antibodies directed to the receptor or other target to which human IL-22 is directed; and peptide and small molecule compounds that inhibit or interfere with the interaction of human IL-22 with its receptor or other target. In one embodiment, the IL-22 antagonist has similar binding characteristics as Ab-02 (e.g., it binds to the same or similar epitope). In another embodiment, the IL-22 antagonist has similar binding characteristics as Ab-04 (e.g., it binds to the same or similar epitope).

As used herein, an "IL-22 agonist" refers to an agent which potentiates, induces or otherwise enhances one or biological activities of an IL-22 polypeptide.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to one or more fragments of a full-length antibody that retain the ability to specifically bind to an antigen (e.g., CD3). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

Sequences similar or homologous (e.g., at least about 85% sequence identity) to the sequences disclosed herein are also part of this application. In some embodiment, the sequence identity can be about 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and non-aqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6×SSC at about 45° C., followed by one or more washes in 0.2×SSC, 0.1% SDS at 55° C. A further example of stringent hybridization conditions are hybridization in 6×SSC at about 45° C., followed by one or more washes in 0.2×SSC, 0.1% SDS at 60° C. Preferably, stringent hybridization conditions are hybridization in 6×SSC at about 45° C., followed by one or more washes in 0.2×SSC, 0.1% SDS at 65° C. Particularly preferred highly stringent conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C.

It is understood that the IL-22 polypeptides and antagonists, e.g., antibodies, thereof of the present invention may have additional conservative or non-essential amino acid substitutions, which do not have a substantial effect on their functions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

IL-22 Proteins, Fragments and Polynucleotides Encoding the Same

IL-22 nucleotide and amino acid sequences are known in the art and are provided below. The nucleotide sequence of each clone can also be determined by sequencing of the deposited clone in accordance with known methods. The predicted amino acid sequence (both full-length and mature forms) can then be determined from such nucleotide sequence. The amino acid sequence of the protein encoded by a particular clone can also be determined by expression of the clone in a suitable host cell, collecting the protein and determining its sequence.

As used herein, a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum.

The nucleotide sequence of human IL-22 is reproduced below (SEQ ID NO:1), and includes a poly(A) tail. The disclosed nucleotide sequence includes an open reading frame and the amino acid sequence of full-length IL-22 protein corresponding to the foregoing nucleotide sequence is reported in SEQ ID NO:2. The amino acid sequence of mature IL-22 corresponds to about amino acids 34-179 of SEQ ID NO:2.

```
GAATTCGGCC AAAGAGGCCT ACAGGTTCTC CTTCCCCAGT CACCAGTTGC  (SEQ ID NO:1)

TCGAGTTAGA ATTGTCTGCA ATGGCCGCCC TGCAGAAATC TGTGAGCTCT

TTCCTTATGG GGACCCTGGC CACCAGCTGC CTCCTTCTCT TGGCCCTCTT

GGTACAGGGA GGAGCAGCTG CGCCCATCAG CTCCCACTGC AGGCTTGACA

AGTCCAACTT CCAGCAGCCC TATATCACCA ACCGCACCTT CATGCTGGCT

AAGGAGGCTA GCTTGGCTGA TAACAACACA GACGTTCGTC TCATTGGGGA

GAAACTGTTC CACGGAGTCA GTATGAGTGA GCGCTGCTAT CTGATGAAGC

AGGTGCTGAA CTTCACCCTT GAAGAAGTGC TGTTCCCTCA ATCTGATAGG

TTCCAGCCTT ATATGCAGGA GGTGGTGCCC TTCCTGGCCA GGCTCAGCAA

CAGGCTAAGC ACATGTCATA TTGAAGGTGA TGACCTGCAT ATCCAGAGGA

ATGTGCAAAA GCTGAAGGAC ACAGTGAAAA GCTTGGAGA GAGTGGAGAG

ATCAAAGCAA TTGGAGAACT GGATTTGCTG TTTATGTCTC TGAGAAATGC

CTGCATTTGA CCAGAGCAAA GCTGAAAAAT GAATAACTAA CCCCCTTTCC

CTGCTAGAAA TAACAATTAG ATGCCCCAAA GCGATTTTTT TTAACCAAAA

GGAAGATGGG AAGCCAAACT CCATCATGAT GGGTGGATTC CAAATGAACC
```

```
CCTGCGTTAG TTACAAAGGA AACCAATGCC ACTTTTGTTT ATAAGACCAG
AAGGTAGACT TTCTAAGCAT AGATATTTAT TGATAACATT TCATTGTAAC
TGGTGTTCTA TACACAGAAA ACAATTTATT TTTTAAATAA TTGTCTTTTT
CCATAAAAAA GATTACTTTC CATTCCTTTA GGGGAAAAAA CCCCTAAATA
GCTTCATGTT TCCATAATCA GTACTTTATA TTTATAAATG TATTTATTAT
TATTATAAGA CTGCATTTTA TTTATATCAT TTTATTAATA TGGATTTATT
TATAGAAACA TCATTCGATA TTGCTACTTG AGTGTAAGGC TAATATTGAT
ATTTATGACA ATAATTATAG AGCTATAACA TGTTTATTTG ACCTCAATAA
ACACTTGGAT ATCCTAAAAA AAAAAAAAAA AAAGCGGCCG C
```

The polypeptide sequence of the encoded polypeptide is shown below.

```
MAALQKSVSS FLMGTLATSC LLLLALLVQG GAAAPISSHC RLDKSNFQQP  (SEQ ID NO:2)
YITNRTFMLA KEASLADNNT DVRLIGEKLF HGVSMSERCY LMKQVLNFTL
EEVLFPQSDR FQPYMQEVVP FLARLSNRLS TCHIEGDDLH IQRNVQKLKD
TVKKLGESGE IKAIGELDLL FMSLRNACI
```

Nucleotide sequences encoding murine IL-22, and the sequence of the encoded polypeptide, are provided below:

```
GAATTCGGCC AAAGAGGCCT ACCTAAACAG GCTCTCCTCT CAGTTATCAA  (SEQ ID NO:3)
CTGTTGACAC TTGTGCGATC TCTGATGGCT GTCCTGCAGA AATCTATGAG
TTTTTCCCTT ATGGGACTT TGGCCGCCAG CTGCCTGCTT CTCATTGCCC
TGTGGGCCCA GGAGGCAAAT GCGCTGCCCG TCAACACCCG GTGCAAGCTT
GAGGTGTCCA ACTTCCAGCA GCCATACATC GTCAACCGCA CCTTTATGCT
GGCCAAGGAG GCCAGCCTTG CAGATAACAA CACAGATGTC CGGCTCATCG
GGGAGAAACT GTTCCGAGGA GTCAGTGCTA AGGATCAGTG CTACCTGATG
AAGCAGGTGC TCAACTTCAC CCTGGAAGAC GTTCTGCTCC CCCAGTCAGA
CAGGTTCCAG CCCTACATGC AGGAGGTGGT GCCTTTCCTG ACCAAACTCA
GCAATCAGCT CAGCTCCTGT CACATCAGCG GTGACGACCA GAACATCCAG
AAGAATGTCA GAAGGCTGAA GGAGACAGTG AAAAAGCTTG GAGAGAGTGG
AGAGATCAAG GCGATTGGGG AACTGGACCT GCTGTTTATG TCTCTGAGAA
ATGCTTGCGT CTGAGCGAGA AGAAGCTAGA AAACGAAGAA CTGCTCCTTC
CTGCCTTCTA AAAGAACAA TAAGATCCCT GAATGGACTT TTTTACTAAA
GGAAAGTGAG AAGCTAACGT CCATCATTAT TAGAAGATTT CACATGAAAC
CTGGCTCAGT TGAAAAAGAA AATAGTGTCA AGTTGTCCAT GAGACCAGAG
GTAGACTTGA TAACCACAAA GATTCATTGA CAATATTTTA TTGTCACTGA
TGATACAACA GAAAAATAAT GTACTTTAAA AAATTGTTTG AAAGGAGGTT
ACCTCTCATT CCTTTAGAAA AAAGCTTAT GTAACTTCAT TTCCATAACC
AATATTTTAT ATATGTAAGT TTATTTATTA TAAGTATACA TTTTATTTAT
GTCAGTTTAT TAATATGGAT TTATTTATAG AAACATTATC TGCTATTGAT
```

-continued

```
ATTTAGTATA AGGCAAATAA TATTTATGAC AATAACTATG GAAACAAGAT

ATCTTAGGCT TTAATAAACA CATGGATATC ATAAAAAAAA AAAAAAAAAA

AAAAAAAGC GGCCGC
```

The amino acid sequence of the polypeptide encoded by the above-referenced polynucleotide sequence is provide below:

```
  1 MAVLQKSMSF SLMGTLAASC LLLIALWAQE ANALPVNTRC KLEVSNFQQP  (SEQ ID NO:4)

51 YIVNRTFMLA KEASLADNNT DVRLIGEKLF RGVSAKDQCY LMKQVLNFTL

101 EDVLLPQSDR FQPYMQEVVP FLTKLSNQLS SCHISGDDQN IQKNVRRLKE

151 TVKKLGESGE IKAIGELDLL FMSLRNACV*
```

Any form of IL-22 proteins of less than full length can be used in the methods and compositions of the present invention, provided that it retains the ability to bind to an IL-22 receptor. IL-22 fragments, e.g., IL-22 proteins of less than full length, can be produced by expressing a corresponding fragment of the polynucleotide encoding the full-length IL-22 protein in a host cell. These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

Fragments of the protein can be in linear form, or they can be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments can be fused to carrier molecules such as immunoglobulins for many purposes, including increasing the valency of protein binding sites. For example, fragments of the protein can be fused through "linker" sequences to the Fc portion of an immunoglobulin. For a bivalent form of the protein, such a fusion can be to the Fc portion of an IgG molecule. Other immunoglobulin isotypes may also be used to generate such fusions. For example, a protein-IgM fusion generates a decavalent form of the protein of the invention.

IL-22 proteins and fragments thereof include proteins with amino acid sequence lengths that are at least 25%(more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

In another embodiment, proteins, protein fragments, and recombinant proteins of the present invention include those that can be identified based on the presence of at least one "IL-22 receptor-binding motif." As used herein, the term "IL22 receptor-binding motif" includes amino acid sequences or residues that are important for binding of IL-22 to its requisite receptor. In a preferred embodiment, a IL-22 protein contains a IL-22 receptor-binding motif including about amino acids 50-60 of SEQ ID NO:2. In another embodiment, an IL-22 protein contains a IL-22 receptor-binding motif including about amino acids 63-81 of SEQ ID NO:2. In yet another embodiment, an IL-22 protein contains a IL-22 receptor-binding motif including about amino acids 168-177 of SEQ ID NO:2. In a preferred embodiment, an IL-22 protein contains a IL-22 receptor-binding motif including at least one of amino acids 50-60, amino acids 63-81, and/or about amino acids 168-177 of SEQ ID NO:2.

In yet another embodiment, a IL-22 receptor binding motif has an amino acid sequence at least 95%, 96%, 97%, 98%, 99%, or more identical to an amino acid sequence selected from the group consisting of amino acids 50-60 of SEQ ID NO:2, amino acids 63-81 of SEQ ID NO:2, and amino acids 168-177 of SEQ ID NO:2.

In another embodiment, proteins, protein fragments, and recombinant proteins of the present invention include those which can be identified based on the presence of at least one, two, three, four or more sites for N-linked glycosylation, length can be determined by aligning the sequences of the polynucleotides and identifying the region or regions of optimal sequence complementarity.

Vectors and Host Cells

The IL-22 polynucleotides can be operably linked to an expression control sequence such as the pMT2 or pED expression vectors disclosed in Kaufman et al., Nucleic Acids Res. 19, 4485-4490 (1991), in order to produce the protein recombinantly. Many suitable expression control sequences are known in the art. General methods of expressing recombinant proteins are also known and are exemplified in R. Kaufman (1990) Methods in Enzymology 185, 537-566. As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated.

Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention includes such other forms of expression vectors, such as viral vectors (e.g., replication defective retroviruses, adenoviruses and adeno-associated viruses), which serve equivalent functions.

The term "regulatory sequence" is intended to includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from FF-1a promoter and BGH polyA, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

The recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

A number of types of cells may act as suitable host cells for expression of the IL-22 protein or fusion protein thereof. Any cell type capable of expressing functional IL-22 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC 12, M1x or C2C12 cells.

The IL-22 protein or fusion protein thereof may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MaxBac® kit), and such methods are well known in the art, as described in Summers and Smith, Texas Agricultural Experiment Station Bulletin No. 1555 (1987), incorporated herein by reference. Soluble forms of the IL-22 protein may also be produced in insect cells using appropriate isolated polynucleotides as described above.

Alternatively, the IL-22 protein or fusion protein thereof may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, Meth. Enzym., 185:187-195 (1990). EP 0433225 and copending application U.S. Ser. No. 08/163,877 describe other appropriate methods.

The IL-22 protein or fusion protein thereof may also be expressed as a product of transgenic animals, e.g., as a component of the milk of transgenic cows, goats, pigs, or sheep which are characterized by somatic or germ cells containing a polynucleotide sequence encoding the IL-22 protein or fusion protein thereof.

The IL-22 protein or fusion protein thereof may be prepared by growing a culture transformed host cells under culture conditions necessary to express the desired protein. The resulting expressed protein may then be purified from the culture medium or cell extracts. Soluble forms of the IL-22 protein or fusion protein thereof can be purified from conditioned media. Membrane-bound forms of IL-22 protein of the invention can be purified by preparing a total membrane fraction from the expressing cell and extracting the membranes with a non-ionic detergent such as Triton X-100.

The IL-22 protein can be purified using methods known to those skilled in the art. For example, the IL-22 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the IL-22 protein or fusion protein from culture supernatant may also include one or more column steps over such affinity resins as concanavalin A-agarose, Heparin-Toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the IL-22 protein. Affinity columns including antibodies to the IL-22 protein can also be used in purification in accordance with known methods. Some or all of the foregoing purification steps, in various combinations or with other known methods, can also be employed to provide a substantially purified isolated recombinant protein. Preferably, the isolated IL-22 protein is purified so that it is substantially free of other mammalian proteins.

IL-22 proteins or fusion proteins of the invention may also be used to screen for agents (e.g., IL-22 antagonists, e.g., anti-IL-22 antibodies) that are capable of binding to IL-22. Binding assays using a desired binding protein, immobilized or not, are well known in the art and may be used for this purpose using the IL-22 protein of the invention. Purified cell based or protein based (cell free) screening assays may be used to identify such agents. For example, IL-22 protein may be immobilized in purified form on a carrier and binding or potential ligands to purified IL-22 protein may be measured.

IL-22 polypeptides may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they can be employed as biologically active or immunological substitutes for natural, purified proteins in screening of therapeutic compounds and in immunological processes for the development of antibodies.

Anti-IL-22 Antibodies and Antigen-Binding Fragments Thereof

In other embodiments, the IL-22 antagonists are antibodies, or antigen-binding fragments thereof, that bind to IL-22, preferably, mammalian (e.g., human or murine) IL-22. In one embodiment, the anti-IL22 antibody or fragment thereof (e.g., an Fab, F(ab')$_2$, Fv or a single chain Fv fragment) is a monoclonal or single specificity antibody. The antibody or fragment thereof can also be a human, humanized, chimeric, or in vitro generated antibody against human IL-22.

IL-22 polypeptides may also be used to immunize animals to obtain polyclonal and monoclonal antibodies that specifically react with the IL-22 polypeptides. Such antibodies may be obtained using the entire IL-22 as an immunogen, or by using fragments of IL-22. Smaller fragments of the IL-22 may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, *J. Amer. Chem. Soc.* 85: 2149-2154 (1963); J. L. Krstenansky, et al., FEBS Lett. 211, 10 (1987). Neutralizing or non-neutralizing antibodies (preferably monoclonal antibodies) binding to IL-22 protein may also be useful in the treatment of the IL-22 associated disorders described herein. These neutralizing monoclonal antibodies may be capable of blocking IL-22 binding to an IL-22 receptor, e.g., IL-22R or IL-10R2 or a combination thereof.

Example 5 below describes the production of anti-IL-22 antibodies in more detail. Non-limiting example of an anti-IL22 antibody that interferes with IL-22 binding to IL-22R is "Ab-04." Ab-04 (also referred to herein as rat monoclonal antibody "P3/2") binds to human IL-22 and neutralizes human IL-22 activity (see Example 5, 16 and 17). A hybridoma cell line producing Ab-04 has been deposited with the ATCC on Jun. 5, 2003 and has been assigned ATCC accession number PTA-5255. Another non-limiting example of an anti-IL22 antibody that interferes with IL-22 binding to IL-10R2 is "Ab-02." Ab-02 (also referred to herein as rat monoclonal antibody "P3/3") binds to mouse and human IL-22 and neutralizes the activity of mouse and human IL-22 (see Example 5, 16 and 17). A hybridoma cell line producing Ab-02 has been deposited on Jun. 5, 2003 with the ATCC and has been assigned ATCC accession number PTA-5254.

Human monoclonal antibodies (mAbs) directed against IL-22 can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11: 152-156). A similar strategy can also been used to amplify human heavy and light chain variable regions from human antibodies (Larrick et al., 1991, *Methods: Companion to Methods in Enzymology* 2:106-110).

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

An antibody or an immunoglobulin chain can be humanized by methods known in the art. Humanized antibodies, including humanized immunoglobulin chains, can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target. The recombinant DNA encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDR's of a particular human antibody may be replaced with at least a portion of a non-human CDR or only some of the CDR's may be replaced with non-human CDR's. It is only necessary to replace the number of CDR's required for binding of the humanized antibody to a predetermined antigen.

Monoclonal, chimeric and humanized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

Pharmaceutical Compositions

IL-22 binding agents, e.g., IL22 antagonists, (e.g., anti-IL-22 antibodies and antigen-binding fragments thereof) can be used as a pharmaceutical composition when combined with a pharmaceutically acceptable carrier. Such a composition may contain, in addition to the IL-22-agonists or antagonists and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may be in the form of a liposome in which IL-22-antagonists is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

In practicing the method of treatment or use of the present invention, a therapeutically effective amount of an IL-22 antagonist is administered to a subject, e.g., mammal (e.g., a human). An IL-22 antagonist may be administered in accordance with the method of the invention either alone or in combination with other therapies, e.g., anti-inflammatory agents described in more detail below. When co-administered with one or more agents, an IL-22 antagonist may be administered either simultaneously with the second agent, or sequentially. If administered sequentially, the attending physician will decide on the appropriate sequence of administering an IL-22 antagonist in combination with other agents.

Administration of an IL-22 antagonist used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of an IL-22 antagonist is administered orally, the binding agent will be in the form of a tablet, capsule, powder, solution or elixir. When administered in tablet form, the pharmaceutical composition of the invention may additionally contain a solid carrier such as a gelatin. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

When a therapeutically effective amount of an IL-22 antagonist is administered by intravenous, cutaneous or subcutaneous injection, binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of an IL-22 binding agent in the pharmaceutical composition of the present invention will depend upon the nature and severity of the condition being treated, and on the nature of prior treatments that the patient has undergone. Ultimately, the attending physician will decide the amount of binding agent with which to treat each individual patient. Initially, the attending physician will administer low doses of binding agent and observe the patient's response. Larger doses of binding agent may be administered until the optimal therapeutic effect is obtained for the patient, and at that point the dosage is not generally increased further. It is contemplated that the various pharmaceutical compositions used to practice the method of the present invention should contain about 0.1 μg to about 100 mg IL-22 binding agent per kg body weight.

The duration of intravenous therapy using the pharmaceutical composition of the present invention will vary, depending on the severity of the disease being treated and the condition and potential idiosyncratic response of each individual patient. It is contemplated that the duration of each application of the IL-22 binding agent will be in the range of 12 to 24 hours of continuous intravenous administration. Ultimately the attending physician will decide on the appropriate duration of intravenous therapy using the pharmaceutical composition of the present invention.

Uses of IL-22 Agonists and IL-22 Antagonists

IL-22 is a cytokine involved in pro-inflammatory actions, e.g., inducing an acute phase response. As described in detail in the Examples below, IL-22 induces changes associated with those caused by inflammatory cytokines (such as IL-1 and TNFα), and inhibitors of IL-22 ameliorate symptoms of rheumatoid arthritis. Therefore, IL-22, and/or agents that increase levels of IL-22 or mimic the actions of IL-22 (and other molecules of the present invention) are useful as agonists in certain clinical indications, and antagonists of this molecule are useful in other clinical situations, particularly in those in which modulation of an inflammatory state is desired. Whether the agonist or antagonist is the preferred depends on the particular aspects of the disease pathology, such as the cell types involved, the nature of the stimulus and the cellular microenvironment.

Human IL-22 agonists include without limitation human IL-22 proteins and fragments, deletion mutants and addition mutants thereof; and peptide and small molecule compounds that interact with the receptor or other target to which human IL-22 is directed. Human IL-22 antagonists include without limitation antibodies directed to human IL-22 proteins; soluble forms of the receptor or other target to which human IL-22 is directed; antibodies directed to the receptor or other target to which human IL-22 is directed; and peptide and small molecule compounds that inhibit or interfere with the interaction of human IL-22 with its receptor or other target.

In one aspect, the invention features a method of inhibiting at least one IL-22-associated activity, by contacting a cell, e.g., an epithelial cell, with an IL-22 antagonist (e.g., an anti-IL-22 antibody or an antigen-binding fragment thereof), in an amount sufficient to inhibit the activity. Antagonists of IL-22 (e.g., a neutralizing antibody, as described herein) can also be administered to subjects for which inhibition of an immune IL-22-associated activity is desired. These conditions include, e.g., autoimmune disorders (e.g., arthritic disorders), respiratory disorders or inflammatory conditions. Applicants have shown that a reduction of IL-22 activity by using a neutralizing anti-IL-22 antibody ameliorates inflammatory symptoms in mouse collagen-induced arthritis (CIA) animal models (Example 9). Expression of IL-22 mRNA is upregulated in the paws of CIA mice (Example 10). Accordingly, IL-22 antagonists can be used to induce immune suppression in vivo, e.g., for treating or preventing IL-22-associated disorders, in a subject. As used herein, the term "subject" is intended to include human and non-human animals. Preferred human animals include a human patient having a disorder characterized by abnormal IL-22 activity. The term "non-human animals" of the invention includes all vertebrates, e.g., mammals and non-mammals, such as non-human primates, rodents, sheep, dog, cow, chickens, amphibians, reptiles, etc.

Non-limiting examples of IL-22-associated disorders that can be treated or prevented include, but are not limited to, transplant rejection, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), Sjögren's Syndrome, Crohn's disease, aphthous ulcer, iritis, conjunctivitis, keratoconjunctivitis, ulcerative colitis, spondyoarthropathy, ankylosing spondylitis, intrinsic asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis); respiratory disorders, e.g., asthma or COPD; inflammatory conditions of the skin (e.g., psoriasis), liver (e.g., hepatitis), kidney (e.g., nephritis) and pancreas (e.g., pancreatitis); graft-versus-host disease, and allergy such as, atopic allergy. Preferred disorders that can be treated using the binding agents of the invention include arthritic disorders (e.g., rheumatoid arthritis, juvenile rheumatoid arthritis, osteoarthritis, psoriatic arthritis, and ankylosing spondylitis (preferably, rheumatoid arthritis)), multiple sclerosis, type I diabetes, lupus (SLE), IBD, Crohn's disease, COPD, asthma, vasculitis, allergy, scleroderma, and inflammatory conditions of the skin (e.g., psoriasis), liver (e.g., hepatitis), kidney (e.g., nephritis) and pancreas (e.g., pancreatitis).

In another embodiment, IL-22 antagonists, alone or in combination with, other therapeutic agents as described herein (e.g., TNF antagonists) can be used to treat multiple myeloma and related B lymphocytic malignancies (Brenne, A. et al. (2002) *Blood Vol.* 99(10):3756-3762).

In one embodiment, the IL-22 antagonists, e.g., pharmaceutical compositions thereof, are administered in combination therapy, i.e., combined with other agents, e.g., therapeutic agents that are useful for treating pathological conditions or disorders, such as immune and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more IL-22 antagonists, e.g., an antibody or an antigen-binding fragment thereof as described herein (e.g., a chimeric, humanized, human, or in vitro generated antibody or antigen-binding fragment thereof) against IL-22) co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more IL-22 antagonists described herein may be used in combination with two or more of the therapeutic agents described herein.

Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-22 receptor pathway, and thus are expected to enhance and/or synergize with the effects of the IL-22 antagonists. Without being bound by theory, Applicants believe that IL-22 may exert its inflammatory effects locally, e.g., by acting as an amplifier or a regulator of tissue inflammation as opposed to systemic inflammation. Applicants' belief is based, at least in part, on the finding that expression of IL-22R appears to be localized to tissue sites rather than in circulating immune cells.

Accordingly, inhibition of IL-22 activity using, e.g., an anti-IL22 antibody or fragment thereof described herein, may provide a more effective tissue-specific, anti-inflammatory activity than systemic anti-inflammatory modalities as described herein. Furthermore, inhibition of local IL-22 activity using, e.g., an anti-IL22 antibody or fragment thereof described herein, may provide a useful candidate for combination with systemic anti-inflammatory modalities described herein.

In one embodiment, one or more IL-22 antagonist described herein may be co-formulated with, and/or co-administered with, one or more additional agents such as other cytokine or growth factor antagonists (e.g., soluble receptors, peptide inhibitors, small molecules, ligand fusions); or antibodies or antigen-binding fragments thereof that bind to other targets (e.g., antibodies that bind to other cytokines or growth factors, their receptors, or other cell surface molecules); and anti-inflammatory cytokines or agonists thereof. Non-limiting examples of the agents that can be used in combination with the IL-22 antagonists described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, and IL-21/IL-21R; antagonists of cytokines or growth factors or their receptors, such as tumor necrosis factor (TNF), LT, EMAP-II, GM-CSF, FGF and PDGF. IL-22 antagonists can also be combined with inhibitors of, e.g., antibodies to, cell surface molecules such as CD2, CD3, CD4, CD8, CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4/VCAM-1 (Yusuf-Makagiansar H. et al. (2002) *Med Res Rev* 22(2): 146-67). Preferred antagonists that can be used in combination with IL-22 antagonists described herein include antagonists of IL-1, IL-12, TNFα, IL-15, IL-17, IL-18, and IL-21/IL-21R.

Examples of those agents include IL-12 antagonists, such as chimeric, humanized, human or in vitro generated antibodies (or antigen-binding fragments thereof) that bind to IL-12 (preferably human IL-12), e.g., the antibody disclosed in WO 00/56772, Genetics Institute/BASF); IL-12 receptor inhibitors, e.g., antibodies to human IL-12 receptor; and soluble fragments of the IL-12 receptor, e.g., human IL-12 receptor. Examples of IL-15 antagonists include antibodies (or antigen-binding fragments thereof) against IL-15 or its receptor, e.g., chimeric, humanized, human or in vitro generated antibodies to human IL-15 or its receptor, soluble fragments of the IL-15 receptor, and IL-15-binding proteins. Examples of IL-18 antagonists include antibodies, e.g., chimeric, humanized, human or in vitro generated antibodies (or antigen-binding fragments thereof), to human IL-18, soluble fragments of the IL-18 receptor, and IL-18 binding proteins (IL-18BP, Mallet et al. (2001) *Circ. Res.* 28). Examples of IL-1 antagonists include Interleukin-1-converting enzyme (ICE) inhibitors, such as Vx740, IL-1 antagonists, e.g., IL-IRA (ANIKIRA, AMGEN), sIL1RII (Immunex), and anti-IL-1 receptor antibodies (or antigen-binding fragments thereof).

Examples of TNF antagonists include chimeric, humanized, human or in vitro generated antibodies (or antigen-binding fragments thereof) to TNF (e.g., human TNF a), such as D2E7, (human TNFα antibody, U.S. Pat. No. 6,258,562; BASF), CDP-571/CDP-870/BAY-10-3356 (humanized anti-TNFα antibody; Celltech/Pharmacia), cA2 (chimeric anti-TNFα antibody; Remicade™, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, Enbrel™; Immunex; see e.g., Arthritis & Rheumatism (1994) Vol. 37, S295; J. Invest. Med. (1996) Vol. 44, 235A), p55 kdTNFR-IgG (55 kD TNF receptor-IgG fusion protein (Lenercept)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see e.g., *Arthritis & Rheumatism* (1996) Vol. 39, No. 9 (supplement), S284; Amer. J. Physiol.—*Heart and Circulatory Physiology* (1995) Vol. 268, pp. 37-42). Preferred TNF antagonists are soluble fragments of the TNF receptors, e.g., p55 or p75 human TNF receptors or derivatives thereof, e.g., 75 kdT-NFR-IgG, and TNFa converting enzyme (TACE) inhibitors.

In other embodiments, the IL-22 antagonists described herein can be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins; Seragen; see e.g., Arthritis & Rheumatism (1993) Vol. 36, 1223), and/or antibodies to IL-2R, e.g., anti-Tac (humanized anti-IL-2R; Protein Design Labs, Cancer Res. 1990 Mar. 1; 50(5): 1495-502). Yet another combination includes IL-21 antagonists in combination with non-depleting anti-CD4 inhibitors (IDEC-CE9.1/SB 210396 (non-depleting primatized anti-CD4 antibody; IDEC/SmithKline). Yet other preferred combinations include antagonists of the co-stimulatory pathway CD80 (B7.1) or CD86 (B7.2) including antibodies, soluble receptors or antagonistic ligands; as well as p-selectin glycoprotein ligand (PSGL), anti-inflammatory cytokines, e.g., IL4 (DNAX/Schering); IL-10 (SCH 52000; recombinant IL-10 DNAX/Schering); IL-13 and TGFβ, and agonists thereof (e.g., agonist antibodies).

In other embodiments, one or more IL-22 antagonists can be co-formulated with, and/or co-administered with, one or more anti-inflammatory drugs, immunosuppressants, or metabolic or enzymatic inhibitors. Non-limiting examples of the drugs or inhibitors that can be used in combination with the IL-22 antagonists described herein, include, but are not limited to, one or more of: non-steroidal anti-inflammatory drug(s) (NSAIDs), e.g., ibuprofen, Tenidap (see e.g., Arthritis & Rheumatism (1996) Vol. 39, No. 9 (supplement), S280)), Naproxen (see e.g., Neuro Report (1996) Vol. 7, pp. 1209-1213), Meloxicam, Piroxicam, Diclofenac, and Indomethacin; Sulfasalazine (see e.g., Arthritis & Rheumatism (1996) Vol. 39, No. 9 (supplement), S281); corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diaminio-6-pteridinyl)methyl]methylamino]benzoyl]-L-glutamic acid); and inhibitors of pyrimidine biosynthesis, e.g., dihydroorotate dehydrogenase (DHODH) inhibitors (e.g., leflunomide (see e.g., *Arthritis & Rheumatism* (1996) Vol. 39, No. 9 (supplement), S131; Inflammation Research (1996) Vol. 45, pp. 103-107). Preferred therapeutic agents for use in combination with IL-22 antagonists include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin) or rapamycin derivatives, e.g., soluble rapamycin derivatives (e.g., ester rapamycin derivatives, e.g., CCI-779 (Elit. L. (2002) *Current Opinion Investig. Drugs* 3(8): 1249-53; Huang, S. et al. (2002) *Current Opinion Investig. Drugs* 3(2):295-304); agents which interfere with signaling by proinflammatory cytokines such as TNFα or IL-1 (e.g. IRAK, NIK, IKK, p38 or MAP kinase inhibitors); COX2 inhibitors, e.g., celecoxib and variants thereof, MK-966, see e.g., Arthritis & Rheumatism (1996) Vol. 39, No. 9 (supplement), S81); phosphodiesterase inhibitors, e.g., R973401 (phosphodiesterase Type IV inhibitor; see e.g., Arthritis & Rheumatism (1996) Vol. 39, No. 9 (supplement), S282)); phospholipase inhibitors, e.g., inhibitors of cytosolic phospholipase 2 (cPLA2) (e.g., trifluoromethyl ketone analogs (U.S. Pat. No. 6,350,892)); inhibitors of vascular endothelial cell growth factor or growth factor receptor, e.g., VEGF inhibitor and/or VEGF-R inhibitor; and inhibitors of angiogenesis. Preferred therapeutic agents for use in combination with IL-22 antagonists immunosuppresants, e.g., cyclosporin, tacrolimus (FK-506); and mTOR inhibitors, e.g., sirolimus (rapamycin) or rapamycin derivatives, e.g., soluble rapamycin derivatives (e.g., ester rapamycin derivatives, e.g., CCI-779; COX2 inhibitors, e.g., celecoxib and variants thereof; and phospholipase inhibitors, e.g., inhibitors of cytosolic phospholipase 2 (cPLA2) (e.g., trifluoromethyl ketone analogs)

Additional examples of therapeutic agents that can be combined with an IL-22 antagonist include one or more of: 6-mercaptopurines (6-MP); azathioprine sulphasalazine; mesalazine; olsalazine chloroquinine/hydroxychloroquine; pencillamine; aurothiornalate (intramuscular and oral); azathioprine; cochicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

The use of the IL-22 antagonists disclosed herein in combination with other therapeutic agents to treat or prevent specific immune disorders is discussed in further detail below.

Non-limiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which an IL-22 antagonists can be combined include one or more of the following: IL-12 antagonists as described herein, NSAIDs; CSAIDs; TNF's, e.g., TNFa, antagonists as described herein; non-depleting anti-CD4 antibodies as described herein; IL-2 antagonists as described herein; anti-inflammatory cytokines, e.g., IL-4, IL-10, IL-13 and TGFa, or agonists thereof; IL-1 or IL-1 receptor antagonists as described herein); phosphodiesterase inhibitors as described herein; COX-2 inhibitors as described herein; Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide; inhibitor of plasminogen activation, e.g., tranexamic acid; see e.g., *Arthritis & Rheumatism* (1996) Vol. 39, No. 9 (supplement), S284); cytokine inhibitor, e.g., T-614; see e.g., *Arthritis & Rheumatism* (1996) Vol. 39, No. 9 (supplement), S282); prostaglandin E1 (see e.g., Arthritis & Rheumatism (1996) Vol. 39, No. 9 (supplement), S282); azathioprine (see e.g., Arthritis & Rheumatism (1996) Vol. 39, No. 9 (supplement), S281); an inhibitor of interleukin-1 converting enzyme (ICE); zap-70 and/or lck inhibitor (inhibitor of the tyrosine kinase zap-70 or lck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; interleukin-11 (see e.g., *Arthritis & Rheumatism* (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclophosphamide; cyclosporine; total lymphoid irradiation; anti-thymocyte globulin; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more IL-21 antagonists in combination with methotrexate or leflunomide, and in moderate or severe rheumatoid arthritis cases, cyclosporine.

Preferred examples of inhibitors to use in combination with IL-22 antagonists to treat arthritic disorders include TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™)(, p55 kD TNF receptor-IgG fusion protein; TNF enzyme antagonists, e.g., TNFa converting enzyme (TACE) inhibitors); antagonists of IL-12, IL-15, IL-17, IL-18, IL-21/IL-21R; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFk$\beta$ antagonists. Most preferred additional therapeutic agents that can be co-administered and/or co-formulated with one or more IL-22 antagonists include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™); methotrexate, leflunomide, or a sirolimus (rapamycin) or an analog thereof, e.g., CCI-779.

Non-limiting examples of agents for treating or preventing multiple sclerosis with which an IL-22 antagonists can be combined include the following: interferons, e.g., interferon-alpha1$\alpha$ (e.g., Avonex™; Biogen) and interferon-1$\beta$ (Betaseron™; Chiron/Berlex); Copolymer 1 (Cop-1; Copaxone™; Teva Pharmaceutical Industries, Inc.); hyperbaric oxygen; intravenous immunoglobulin; clabribine; TNF antagonists as described herein; corticosteroids; prednisolone; methylprednisolone; azathioprine; cyclophosphamide; cyclosporine; methotrexate; 4-aminopyridine; and tizanidine. Additional antagonists that can be used in combination with IL-22 antagonists include antibodies to or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. IL-21 antagonists as described herein can be combined with antibodies to cell surface molecules such as CD2, CD3, CD4, CD8, CD25, CD28, CD30, CD40, CD45, CD69, CD80, CD86, CD90 or their ligands. The IL-22 antagonists may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-I$\beta$ converting enzyme inhibitors (e.g., Vx740), anti-P7s, PSGL, TACE inhibitors, T-cell signaling inhibitors such as kinase inhibitors, metal loproteinase inhibitors, sulfasalazine, azathloprine, 6-mercaptopurines, angiotensin converting enzyme inhibitors, soluble cytokine receptors and derivatives thereof, as described herein, and anti-inflammatory cytokines (e.g. IL-4, IL-10, IL-13 and TGF).

Preferred examples of therapeutic agents for multiple sclerosis with which the IL-22 antagonists can be combined include interferon-$\beta$, for example, IFNb-1$\alpha$ and IFNb-1$\beta$; copaxone, corticosteroids, IL-1 inhibitors, TNF inhibitors, antibodies to CD40 ligand and CD80, IL-12 antagonists.

Non-limiting examples of agents for treating or preventing inflammatory bowel disease or Crohn's disease with which an IL-22 antagonist can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13 and/or TGF$\beta$ cytokines or agonists thereof (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In one embodiment, an IL-22 antagonists can be used in combination with one or more antibodies directed at other targets involved in regulating immune responses, e.g., transplant rejection or graft-v-host disease. Non-limiting examples of agents for treating or preventing immune responses with which an IL-21/IL21R antagonist of the invention can be combined include the following: antibodies against cell surface molecules, including but not limited to CD25 (interleukin-2 receptor-$\alpha$), CD11a (LFA-1), CD54 (ICAM-1), CD4, CD45, CD28/CTLA4, CD80 (B7-1) and/or CD86 (B7-2). In yet another embodiment, an IL-22 antagonist is used in combination with one or more general immunosuppressive agents, such as cyclosporin A or FK506.

Another aspect of the present invention accordingly relates to kits for carrying out the combined administration of the IL-22 antagonists with other therapeutic compounds. In one embodiment, the kit comprises one or more binding agents formulated in a pharmaceutical carrier, and at least one agent, e.g., therapeutic agent, formulated as appropriate, in one or more separate pharmaceutical preparations.

Diagnostic Assays

An exemplary method for detecting the presence or absence of IL-22 protein or nucleic acid in a biological sample involves obtaining a biological sample from a test subject and contacting the biological sample with a compound or an agent capable of detecting IL-22 protein or nucleic acid (e.g., mRNA, genomic DNA) that encodes IL-22 protein such that the presence of IL-22 protein or nucleic acid is detected in the biological sample. A preferred agent for detecting IL-22 mRNA or genomic DNA is a labeled nucleic acid probe capable of hybridizing to IL-22 mRNA or genomic DNA. The nucleic acid probe can be, for example, a full-length IL-22 nucleic acid, such as the nucleic acid of SEQ ID NO: 1, or a fragment or portion of an IL-22 nucleic acid such as an oligonucleotide of at least 15, 30, 50, 100, 250 or 500 nucleotides in length and sufficient to specifically hybridize under stringent conditions to IL-22 mRNA or genomic DNA. Other suitable probes for use in the diagnostic assays of the invention are described herein.

A preferred agent for detecting IL-22 protein is an antibody capable of binding to IL-22 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect IL-22 mRNA, protein, or genomic DNA in a biological sample in vitro as well as in vivo. For example, in vitro techniques for detection of IL-22 mRNA include Northern hybridizations and in situ hybridizations. In vitro techniques for detection of IL-22 protein include enzyme linked immunosorbent assays (ELISAs), Western blots, immunoprecipitations and immunofluorescence. In vitro techniques for detection of IL-22 genomic DNA include Southern hybridizations. Furthermore, in vivo techniques for detection of IL-22 protein include introducing into a subject a labeled anti-IL-22 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting IL-22 protein, mRNA, or genomic DNA, such that the presence of IL-22 protein, mRNA or genomic DNA is detected in the biological sample, and comparing the presence of IL-22 protein, mRNA or genomic DNA in the control sample with the presence of IL-22 protein, mRNA or genomic DNA in the test sample. The invention also encompasses kits for detecting the presence of IL-22 in a biological sample. For example, the kit can comprise a labeled compound or agent (e.g. probe or antibody) capable of detecting IL-22 protein or mRNA in a biological sample; means for determining the amount of IL-22 in the sample; and means for comparing the amount of IL-22 in the sample with a standard. The compound or agent can be packaged in a suitable container. The kit can further comprise instructions for using the kit to detect IL-22 protein or nucleic acid.

Screening Assays

The antagonists described herein can be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. The methods described in the appended examples can be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The activity of IL-22 and antibodies of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowman et al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. *In Current Protocols in Immunology.* J. E. e. a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169: 1255-1264, 1989; Bhardwaj et al., Journal of Clinical Investigation 94:797-807, 1994; and Inaba et al., Journal of Experimental Medicine 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad. Sci. USA 88:7548-7551, 1991.

Modulatory agents identified by the above-described screening assays are tested in an appropriate animal model, for example, to determine the efficacy, toxicity, or side effects of treatment with such an agent. Alternatively, modulatory agents are tested in at least one of the in vitro or in situ assays described herein.

Assaying Effects of IL-22 Agonists or Antagonists

The activity of an IL-22 agonist or antagonist can be measure by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnolli, et al., J. Immunol. 149:3778-3783, 1992; Bowman et al., J. Immunol. 152: 1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. Coligan eds. Vol 1 pp. 3.12.1-3.12.14, John Wiley and Sons, Toronto. 1994; and Measurement of mouse and human Interferon γ, Schreiber, R. D. In *Current Protocols in Immunology*. J. E. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e. a. Coligan eds. Vol 1 pp. 6.3.1-6.3.12, John Wiley and Sons, Toronto. 1991; deVries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6—Nordan, R. In *Current Protocols in Immunology*. J. E. e. a. Coligan eds. Vol 1 pp. 6.6.1-6.6.5, John Wiley and Sons, Toronto. 1991; Smith et al., Proc. Natl. Acad. Sci. U.S.A. 83:1857-1861, 1986; Measurement of human Interleukin 11—Bennett, F., Giannotti, J., Clark, S. C. and Turner, K. J. In *Current Protocols in Immunology*. J. E. e. a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology*. J. E. e. a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

This invention is further illustrated by the non-limiting examples. The contents of all references, patents and published patent applications cited throughout this application, as well as the Sequence Listing, are incorporated herein by reference.

EXAMPLES

Example 1

Identification and Characterization of Clone "IL-22"

A polynucleotide of the present invention has been identified as clone "IL-22". Clone IL-22 was isolated according to the following method. A murine EST was identified from a murine cDNA library made from splenocytes activated with both ConA and bone marrow derived dendritic cells. The EST was identified using methods which are selective for cDNAs encoding secreted proteins (see U.S. Pat. No. 5,536,637). The murine EST sequence was used to isolate a full-length murine clone from the same cDNA library. Analysis of the sequence of the murine clone revealed a significant homology to interleukin-10 (IL-10).

In order to isolate a human homolog of the murine clone, PCR primers were constructed based upon the region of the murine sequence that showed homology to IL-10. Use of such primers for amplification in a cDNA library derived from PHA/PMA-stimulated human PBMCs produced a PCR product of significant size. Analysis of the sequence of the PCR product confirmed that it was a homolog of the murine cDNA. Oligonucleotides were constructed from the sequence of the partial human clone and used to isolate a full-length human clone from the PBMC library.

IL-22 is a full-length human clone, including the entire coding sequence of a secreted protein (also referred to herein as "IL-22" protein). Analysis of its amino acid sequence indicated that it has about 23% homology to hIL-10. Based on the putative receptor-binding motifs in IL-10, three motifs involved with analogous function have been proposed in IL-22 through computer modeling. These are the regions of SEQ ID NO:2 from residue 50 to 60, from residue 63 to 81, and from residue 168 to 177. Analyses of databases revealed that IL-22 also exhibits similar levels of homology with IL-10 of other species.

The nucleotide sequence of IL-22 as presently determined is reported in SEQ ID NO:1, and includes a poly(A) tail. The amino acid sequence of the IL-22 protein corresponding to the foregoing nucleotide sequence is reported in SEQ ID NO:2.

Example 2

Characterization of IL-22 Protein

Cell lines which stably express and secrete full length IL-22 protein were created by transfecting CHO cells with IL-22 cDNA in appropriate expression vectors. Transiently transfected COS cells using appropriate IL-22 expression vectors have been used to make IL-22 protein for analysis. Transfections were accomplished using the commercially available Lipofectamine reagent (Gibco). Interestingly, COS cells which express IL-22 were observed to non-uniformly detach, forming holes in the cell culture monolayer. Media conditioned by transfected COS cells was used to demonstrate cytokine-like activity of IL-22 protein. Western blot analysis of cell lysates showed that Stat-3 becomes phosphorylated (activated) in a kidney mesangial tissue-derived cell line exhibiting macrophage-like qualities (MES-13; see, Dumoutier et al (2000) *J. of Immunology* 164:1814-1819) upon exposure of that cell to media conditioned by IL-22-expressing cells. In addition phosphorylation of Stat-3 is induced in non-transfected COS cells that are treated with IL-22 protein.

Electrophoretic analysis of IL-22 protein (derived from the transfected COS cell lines described herein) indicated that the expressed protein exists in a range of sizes. Treatment of COS-derived IL-22 protein with N-glycanase prior to electrophoresis results in a single band corresponding to the highest mobility (e.g. lowest molecular weight) species seen in untreated IL-22. This is consistent with proposed glycosylation events which may occur at the putative N-linked glycosylation sites identified in the amino acid sequence of IL-22 (amino acid residues 54-56, 68-70, 97-99, and 176-178 of SEQ ID NO:2).

Edman N-terminal sequencing determined that the N-terminus of the mature IL-22 protein begins with the residue at position 34 of SEQ ID NO:2 (alanine). Expression vectors were created which fuse a "6x histidine" affinity tag and a FLAG epitope tag to the N-terminus of the mature IL-22 protein. (The added amino acid tag is given in SEQ ID NO:5 and has the following amino acid sequence:

MKFLVNVALVFMVVYISYIYAGSGHHHHHHGSGDYKDDDDKAPISSHC

R).

These tagged constructs were used to create stably expressing CHO cell lines and transiently expressing COS cell lines. The tags provided a convenient means for detecting IL-22 (e.g., anti-6xhis antibodies; anti-FLAG antibodies), and for purifying the protein from conditioned media (using $Ni^{+2}$ resin). Human IL-22 protein purified by this tag from the IL-22-expressing COS cell lines could used to induce Stat-3 activation in MES-13 cells.

Comparison of IL-22 mRNA transcripts in activated Th1 and Th2 cells (see, for example, Syrbe et al, (1999) *Springer Seminars in Immunopathology*, 21:263-85) indicated a substantially higher level of expression of IL-22 in activated Th1 cells than in activated Th2 cells. Analysis of IL-22 mRNA was accomplished with RNAse protection assays. Therefore, IL-22 is induced during an adaptive immune response, specifically by Th1 CD4+ T cells.

Example 3

Establishment of IL-22 Recombinant Adenovirus Vector and In Vivo Administration

The Adori 1-2 murine IL-22 (mIL-22) vector was derived by digesting pED6dpc-2mIL-22 with EcoRI and NotI, and ligating the 1.1 kb mIL-22 cDNA fragment with EcoRI and NotI digested adenovirus vector Adori 1-2. Adori 1-1 green fluorescent protein (GFP) construct was derived by digesting pEGFP-N, 1 (CLONTECH Laboratories, Inc., Palo Alto, Calif.) with EcoRI and NotI and inserting the EGFP into the EcoRI and NotI site of Adori 1-1. Both constructs were verified by extensive restriction digestion analysis and sequencing of the cDNA inserts within the plasmids. Expression of the mIL-22 cDNA and EGFP are driven from cytomegalovirus (CMV) immediate early promoter and enhancer.

Ad5 E1a deleted (dl327) recombinant adenovirus was generated by homologous recombination in a human kidney embryonic kidney cell line 293. Recombinant adenovirus virus was isolated and subsequently amplified on 293 cells. The virus was released from infected 293 cells by three cycles of freeze thawing. The virus was further purified by two cesium chloride centrifugation gradients and dialyzed against phosphate buffered saline (PBS) pH 7.2 at 4° C. Following dialysis, glycerol was added to a concentration of 10% and the virus was stored at −80° C. until use. The virus was characterized by expression of the transgene, plaque forming units on 293 cells, particles/ml, endotoxin measurements and PCR analysis of the virus and sequence analysis of the IL-22 coding region in the virus.

A single dose of $5 \times 10^{10}$ particles of recombinant adenovirus encoding mIL-22 was injected into the tail vein of female C57B1/6 mice, age 7-8 weeks. Control mice received an adenovirus encoding GFP or PBS/10% glycerol. Mice from each experimental group were sacrificed at various time points post injection. For hematological and serum chemistry analysis blood was collected by cardiac puncture. Blood was collected via retro-orbital sinus and differential counts were performed on blood smears. Tissue was harvested, fixed in formalin, and stained with hematoxylin and eosin for histopathology.

Example 4

Immunological Effects IL-22

The immunological effects of IL-22 were investigated in a metazoan context by viral introduction of the cDNA of murine IL-22 into mice. An adenoviral vector was used to express a cDNA of murine IL-22 in 8-week old C57/B6 female mice by injection of $5 \times 10^{10}$ viral particles either intravenously or subcutaneously. Test mice were sacrificed at 7 and 14 days after injection and compared with control mice injected with buffer only or with adenovirus expressing green fluorescent protein (GFP). At days 7 and 14, it was noted that the absolute and relative thymic weights were significantly decreased in the mice that expressed the viral murine IL-22.

Absolute mean weight of the spleen was decreased on day 14 and liver weights were slightly increased on day 7. A gross generalized atrophy of the thymus as well as lymphoid depletion (observed microscopically) was apparent on days 7 and 14. An increase in kidney weight and enlargement of the liver were also observed.

In addition, there were a number of hematological effects that were apparent on day 7, including decreased erythroid parameters, red blood cell count, hemoglobin, and hematocrit. These effects, taken together, indicated anemia in the animals. Furthermore, there was an increase in platelets, as well as an increase in the white blood cell count due to an increase of neutrophils. In light of these observations there was no evidence of a regenerative response, which indicated that the effects can be at the level of the bone marrow. A possible cause for this is the loss of small molecules through the kidney or gut. Furthermore, there was a slight decrease in Albumin levels at day 7 and day 14, but an increase in serum amyloid A and fibrinogen levels, which are indicative of an acute phase response. Analysis of liver RNA showed increases in SAA's, GRO1, OPN, LCN2, PRTN3 and SOCS3 (see Table 3 below). Other clinical observations included loss in body weight, signs of minimal dehydrations, increase urine specific gravity, a decrease in urine output and the induction of renal proximal tubular basophilia. The basophilia observed is due to increased cell division and increased rRNA present in the epithelial cells of the renal proximal tube. The changes detected after administration of IL-22 are consistent with IL-22's ability to induce an acute phase response (see e.g., Gabay, C. (1999) *New England Journal of Medicine* 340(6): 448-454).

Example 5

Preparation and Characterization of Anti-IL-22 Monoclonal and Polyclonal Antibodies Monoclonal and polyclonal antibodies were prepared using routine methodologies also described in the instant specification. Table 1 below illustrates the binding affinity, CIA efficacy and neutralizing specificity of monoclonal antibodies P3/1, P3/2, P3/3 and P3/5, as well as chicken polyclonal antibody that are directed against IL-22. Antibodies P3/1, P3/2, P3/3 and P3/5 are also referred to herein as Ab-01, Ab-04, Ab-02 and Ab-03, respectively.

TABLE 1

Antibody binding specificity, affinity and neutralizing activity

| IL-22 Antibodies | Rat Monoclonal Abs | | | | Polyclonal Ab Chicken |
|---|---|---|---|---|---|
| | P3/1 (Ab-01) | P3/2 (Ab-04) | P3/3 (Ab-02) | P3/5 (Ab-03) | Polyclonal |
| Binding Specificity | Mouse | Human | Mouse/Human | Mouse | Mouse/Human |
| Neutralizing Specificity | Mouse | Human | Mouse/Human | Mouse | Mouse/Human |
| Affinity ($K_D$) for IL-22 (nM) by Biacore | 0.54 | 1.51 | 68.1 | 0.1 | |
| Effect in ELISA based assay | Enhances in IL22R ELISA; blocks partially in IL22R/IL10R2 | Blocks in both | Enhances in IL22R ELISA; blocks partially in IL22R/IL10R2 | Blocks in both | |
| CIA efficacy | Good | NA | Modest | NA | |
| Epitope | Distinct from Ab-02 | Ab-04 epitope described herein | Ab-02 epitope described herein | Distinct from Ab-04 | |

Binding specificity was determined by ELISA using mouse or human h/f tagged IL-22 microtiter plates. Each antibody showed strong specificity for either mouse or human IL-22 as shown in Table 1. The neutralizing specificity was determined by assessing the ability of the antibody to inhibit STAT3 phosphorylation mediated by 5 ng/ml mouse or human h/f tagged IL-22. Enzyme-linked immunosorbant assays (ELISA) using bound murine IL-22 demonstrate that the mAb P3/1 has ~5 nM $ED_{50}$ based on ~2 nM for IL-22-Fc and ~10 nM for H/F IL-22. Moreover, in addition to recognizing recombinant IL-22, P3/1 mAb also binds native IL-22 secreted from T cells that have been transfected with an IL-22 retroviral vector. The IL-22 antibody P3/1 has been found to have an $ID_{50}$ of ~1 nM, and to work stoichiometricly to block IL-22 activity when the cytokine is present at just saturating conditions (1 nM).

The binding affinity ($K_D$) of rat antibodies Ab-02 and Ab-04 for human IL-22 was determined using Biacore to be 68.1 nM and 1.51 nM, respectively. Under similar conditions, the binding affinity of human IL-22 for human IL-22R-Fc/IL-10R2-Fc complex and IL-22BP-Fc was determined to be 1.48 nM and 3.37 nM, respectively. The experimental conditions used in determining these binding affinities are described in more detail in Example 22 below.

Example 6

Expression of IL-22 mRNA and Receptor

Expression of IL-22 and its receptor was examined semi-quantitative reverse-transcriptase polymerase chain reaction (RT-PCR) in a variety of human and mouse tissues. The experiments reveal that IL-22 messenger RNA (mRNA) is present at very low levels in human testis, lung, prostate and peripheral blood lymphocytes (PBL) as normalized against control actin. Moreover, semi-quantitative RT-PCR shows that IL-22 receptor is detected at highest levels in the human pancreas, and a lower levels in the liver, intestines, skin, thyroid, kidney, heart stomach, testis, salivary glands, adrenal glands and prostate. Alternatively, murine IL-22 receptor shows highest expression in the liver, small intestine, muscle, skin and ovaries, with lower expression in kidney and embryos e8.5 and e19.

Example 7

In Situ Hybridization and Apoptotic Stain for IL-22 Protein

In situ hybridization for IL-22 protein and receptor messenger RNA (mRNA) of mice treated with adenovirus expression IL-22 (AdIL-22) or Lipopolysaccharide (LPS) was performed and the results as follows:

TABLE 2

| A. Detection of IL-22 Cytokine mRNA | | |
|---|---|---|
| Tissue | AdIL-22-treated mice | LPS-treated mice |
| Liver | Day 1: staining in cytoplasm of hepatocytes slightly positive | 6 hrs.: staining in cytoplasm of hepatocytes slightly positive |
| | Days 3 and 14: no specific staining | |
| Spleen | Days 1, 3 and 14: slight staining in periarteriolar region | Negative |
| Heart | N/A | Negative |
| Colon | N/A | Negative |
| Kidneys | Day1: staining in cytoplasm of proximal and distal tubular epithelium, Henle's loop at corticomedullary junction, parietal cells of Bowman space and some epithelial cells was mildly positive | 2 hrs.: staining in cytoplasm of proximal and distal tubular epithelium, Henle's loop at corticomedullary junction was mildly positive |
| | Day 4: staining in cytoplasm of proximal and distal tubular epithelium and Henle's loop at corticomedullary junction | 6 hrs.: staining in cytoplasm of the proximal and distal tubular epithelium and Henle's loop at the corticomedullary junction, glomerular tuft cells, some parietal cells of the Bowman space and few endothelial cells was slightly to moderately positive |
| | Day 14: staining in cytoplasm of proximal tubular epithelium | |
| Pancreas | N/A | 2 and 6 hrs.: staining in cytoplasm of acinar cells slightly positive |
| Lungs | N/A | 2 and 6 hrs.: staining in pneumocytes type II and/or intraaveolar macrophages was slightly to mildly stained |
| Stomach | N/A | 6 hrs.: staining in cytoplasm of basal chief cells was mild |

TABLE 2-continued

| | | |
|---|---|---|
| Duodenum and Jejunum | N/A | 2 and 6 hrs.: staining in cytoplasm of enterocyte brush border was moderate to marked and slightly positive in the intestine nervous plexus cells. |

B. Detection of the IL-22 Receptor mRNA in LPS-treated mice

| Tissue | LPS-treated mice |
|---|---|
| Liver | 2 and 6 hrs.: staining in the cytoplasm of hepatocytes was slight to mild, nuclear staining was observed in heptocytes, bile duct epithelium and endothelial cells. |
| Kidneys | 2 and 6 hrs.: staining was slight to moderate in the cytoplasm and nucleus of proximal and distal tubular epithelium, Henle's loop at the corticomedullary junction, glomerular tuft cells, some parietal cells of Bowman space and a few endothelial cells. |
| Pancreas | 2 and 6 hrs.: staining in cytoplasm of acinar cells slightly positive |
| Heart | 6 hrs.: nuclear staining was moderately positive in cardiomyocytes and endocardial and endothelial cells. |

IL-22 receptor mRNA is additionally detected in small and large intestine, stomach, lymph nodes, spleen, and lung. Expression of IL-22 receptor can additionally be upregulated by a mediator of an innate immune response, such as LPS.

Finally, TUNEL assays of kidney cells taken from c57BL/6 mice receiving mIL-22 protein intravenously showed a few apoptotic epithelial sells in several proximal convoluted tubules. Mice receiving saline intravenously (control group) demonstrated no positive staining.

These data demonstrate that both the cytokine and receptor can be induced during an innate immune response, and that the induction is restricted to tissues that are in an inflammatory state (LPS). During an adaptive immune response, IL-22 can also be induced from Th1 CD4$^+$ T cells. Since circulating leukocytes do not appear to have the receptor, this result suggests that IL-22 functions as an effector within tissue downstream of an adaptive immune response, as is reinforced by the tissue expression of the receptor, constitutively and further upregulated by an innate inducer of inflammation.

Example 8

IL-22 Mediated Changes in Gene Expression

The ability of IL-22 to modulate levels of gene expression in liver cells of mice infected with an AdIL-22 or Ad-GFP construct was examined.

Frozen mouse livers from day 1 and day 3 post-infection were pulverized and RNA was purified using the Promega RNAgents Total RNA Isolation System (Promega, Madison, W). The RNA was further purified using the RNeasy minikit. Total RNA was isolated from human PBMC's using the RNeasy minikit (Qiagen, Hidden, Germany).

Total RNA was prepared for hybridization by denaturing 10 μg of total RNA for 10 minutes at 70° C. with 100 pM T7/T24-tagged oligo-dT primer (synthesized at Genetics Institute, Cambridge, Mass.), and cooled on ice. First strand cDNA synthesis was performed under the following buffer conditions: 1× first strand buffer (Invitrogen Life Technologies, Carlsbad, Calif.), 10 mM DTT (GIBCO/Invitrogen), 500 μM of each dNTP (Invitrogen Life Technologies, Carlsbad, Calif.)), 400 units of Superscript RT II (Invitrogen Life Technologies) and 40 units RNAse inhibitor (Ambion, Austin, Tex.). The reaction proceeded at 47° C. for 1 hour. Second strand cDNA was synthesized with the addition of the following reagents at the final concentrations listed: 1× second strand buffer (Invitrogen Life Technologies), an additional 200 μM of each dNTP (Invitrogen Life Technologies), 40 units of E. coli DNA polymerase I (Invitrogen Life Technologies), 2 units E. coli RNaseH (Invitrogen Life Technologies), and 10 units of E. coli DNA ligase. The reaction proceeded at 15.80 C for 2 hours. During the last five minutes of the reaction 6 units of T4 DNA polymerase (New England Biolabs, Beverly, Mass.) was added.

The resulting double stranded cDNA was purified with the use of BioMag carboxyl terminated particles as follows: 0.2 mg of BioMag particles (Polysciences Inc., Warrington, Pa.) were equilibrated by washing three times with 0.5M EDTA and resuspended at a concentration of 22.2 mg/ml in 0.5M EDTA. The double stranded cDNA reaction was diluted to a final concentration of 10% PEG/1.25M NaCl, and the bead suspension was added to a final bead concentration of 0.614 mg/ml. The reaction was incubated at room temperature for 10 minutes. The cDNA/bead complexes were washed with 300 μl of 70% ethanol, the ethanol was removed and the tubes were allowed to air dry. The cDNA was eluted with the addition of 20 μl of 10 mM Tris-acetate, pH 7.8, incubated for 2-5 minutes and the cDNA containing supernatate was removed.

10 μl of purified double stranded cDNA was added to an in vitro transcription (IVT) solution which contained, 1×IVT buffer (Ambion, Austin, Tex.) 5,000 units T7 RNA polymerase (Epicentre Technologies, Madison, Wis.), 3 mM GTP, 1.5 mM ATP, 1.2 mM CTP and 1.2 mM UTP (Amersham/Pharmacia), 0.4 mM each bio-16 UTP and bio-11 CTP (Enzo Diagnostics, Farmingdale, N.Y.), and 80 units RNase inhibitor (Ambion, Austin, Tex.). The reaction proceeded at 37° C. for 16 hours. Labeled RNA was purified with the use of an RNeasy (Qiagen). The RNA yield was quantified by measuring absorbance at 260 nm.

12 μg of the in vitro transcription product was fragmented in 40 mM Tris-acetate, pH 8.0, 100 mM potassium acetate, and 30 mM magnesium acetate for 35 minutes at 94° C. The fragmented, labeled RNA probes were diluted in hybridization buffer at a final composition of 1×2-N-Morpholinoethanesulfonic acid (MES (buffer (pH 6.5), 50 pM Bio948 (control biotinylated oligo that hybridizes to landmark features on the probe array (Genetics Institute, Cambridge, Mass.), 100 µg/ml herring sperm DNA (Promega, Madison, Wis.), 500 µg/ml acetylated BSA (Invitrogen Life Technologies) and 1 µl/µg standard curve reagent (Proprietary reagent supplied by Gene Logic, Gaithersburg, Md.). This hybridization solution was pre-hybridized with two glass beads (Fisher Scientific, Pittsburgh, Pa.) at 45° C. overnight. The hybridization solution was removed to a clean tube and heated for 1-2 min at 95° C. and microcentrifuged on high for 2 minutes to pellet insoluble debris. Oligonucleotide array cartridges (Murine 74 Kv2, Affymetrix, Santa Clara, Calif.) were pre-wet with non-stringent wash buffer (0.9M NaCl, 60 mM sodium phosphate, 6 mM EDTA and 0.01% Tween20) and incubated at 45° C. with rotation for 5-10 minutes. Buffer was removed from the cartridges, and the arrays were hybridized with 180 ul of the hybridization solution at 45° C. rotating at 45-60 rpm overnight. After overnight incubation the hybridization solutions were removed and the cartridges were filled with non-stringent wash buffer. The array cartridges were washed using a fluidics station according with 10 cycles of 2 mixes/cycle non-stringent wash buffer at 25° C. followed by 4 cycles of 15 mixes/cycle stringent wash buffer (100 mM MES, 0.1M Na+, 0.01% Tween20 and 0.005% antifoam). The probe array was then first stained for 10 minutes at 25° C. in SAPE solution (100 mM MES, 1M Na+, 0.05% Tween20, 0.005% antifoam, 2 mg/ml acetylated BSA (Invitrogen Life Technologies) and 10 ug/ml R phycoerythrin streptavidin (Molecular Probes, Eugene, Oreg.)). After first staining the probe array was washed for 10 cycles of 4 mixes/cycle with non-stringent wash buffer at 25° C. The probe array was then stained for 10 minutes at 25° C. in antibody solution (100 mM MES, 1M Na+, 0.05% Tween 20, 0.005% antifoam, 2 mg/ml acetylated BSA (Invitrogen Life Technologies), 100 µg/ml Goat IgG (SIGMA, St. Louis, Mo.) and 3 µg/ml biotinylated anti-streptavidin antibody (goat) (Vector Laboratories). Following the second stain the probe array was stained again for an additional 10 minutes at 25° C. in SAPE solution. Finally, the probe array was washed for 15 cycles of 4 mixes/cycle with non-stringent wash buffer at 30° C.

Arrays were scanned using an Affymetrix gene chip scanner (Affymetrix, Santa Clara, Calif.). The scanner contained a scanning confocal microscope and used an argon ion laser for the excitation source and emission is detected by a photomultiplier tube at 530 nm bandpass filter (fluorscein0 or 560 longpass filter (phycoerythrin).

mRNA were analyzed on the Murine 74 k (Mu74K) chip set. The data were reduced with the use of GENECHIP 4.0 software. Each experimental sample was compared to a time matched control in a two-file analysis. The data were filtered with the criteria for genes that were called "Present" in one group, and removing all genes that were not called either "Increasing" or "Decreasing".

Data for three mice are presented below (AD-GIL-19 Mouse 49, 51, and 52). Shown are genes whose expression changed relative to Ad-GFP control, with the indicated average-fold change shown for each animal. The changes observed in gene expression of Ad-IL-22 treated animals are consistent with the induction by IL-22 of an acute phase response. The observed changes are also indicative of an inflammatory state in the treated animal.

TABLE 3

| Identifier | Gene Name | Ad-GIL-19 Mouse 49 Avg Fold Change | Ad-GIL-19 Mouse mouse number 51 Avg Fold Change | Ad-GIL-19 Mouse 52 Avg Fold Change |
| --- | --- | --- | --- | --- |
| Day 3 Livers - U74v2 | | | | |
| 1300017C10RIK | RIKEN cDNA 1300017C10 gene | 23.4 | 17.2 | 19.3 |
| SAA-PS | serum amyloid A, pseudogene | 24.6 | 13.9 | 24.3 |
| SAA1 | serum amyloid A 1 | 11.9 | 9.7 | 12.3 |
| SAA2 | serum amyloid A 2 | 10.0 | 8.9 | 10.3 |
| PRTN3 | proteinase 3 | 15.2 | 14.3 | 17.1 |
| SPP1 | secreted phosphoprotein 1 | 10.2 | 7.8 | 10.7 |
| LCN2 | lipocalin 2 | 13.4 | 10.3 | 13.3 |
| SAA3 | serum amyloid A 3 | 10.5 | 5.4 | 8.2 |
| GRO1 | GRO1 oncogene | 8.2 | 5.6 | 7.2 |
| LY6D | lymphocyte antigen 6 complex, locus D | 6.0 | 5.5 | 4.9 |
| GRO1 | GRO1 oncogene | 7.0 | 5.6 | 7.2 |
| RAD51L1 | RAD51 like 1 (S. cerevisiae) | 4.4 | 3.7 | 3.8 |
| GAS6 | growth arrest specific 6 | 4.1 | 3.5 | 4.8 |
| SPI2-2 | serine protease inhibitor 2-2 | 3.7 | 2.8 | 3.8 |
| GADD45G | growth arrest and DNA-damage-inducible 45 gamma | 3.9 | 2.7 | 3.4 |
| CEBPD | CCAAT/enhancer binding protein (C/EBP), delta | 5.3 | 3.2 | 3.9 |

TABLE 3-continued

| Identifier | Gene Name | Ad-GIL-19 Mouse 49 Avg Fold Change | Ad-GIL-19 Mouse 51 Avg Fold Change | Ad-GIL-19 Mouse 52 Avg Fold Change |
|---|---|---|---|---|
| TNFRSF1A | tumor necrosis factor receptor superfamily, member 1a | 3.6 | 2.6 | 3.0 |
| CISH3 | cytokine inducible SH2-containing protein 3 | 4.0 | 3.8 | |
| IL1R1 | interleukin 1 receptor, type I | 5.2 | 2.6 | 5.6 |
| SAP | serum amyloid P-component | 3.1 | 2.5 | 3.3 |
| PEX11A | peroxisomal biogenesis factor 11a | 4.2 | | 3.2 |
| 2310031E04RIK | EST | 2.9 | 2.7 | 3.3 |
| AA880891 | EST | 2.7 | 2.4 | 2.8 |
| CD14 | CD14 antigen | 3.4 | 2.3 | 2.6 |
| MT1 | metallothionein 1 | 2.7 | 2.4 | 2.9 |
| UNK_AW124835 | EST | 2.2 | | 2.0 |
| TM4SF7 | transmembrane 4 superfamily member 7 | 2.6 | 2.8 | 2.4 |
| DNCLC1 | dynein, cytoplasmic, light chain 1 | 2.5 | 2.4 | 2.6 |
| SAA4 | serum amyloid A 4 | 3.2 | | 2.8 |
| 2410006H10RIK | RIKEN cDNA 2410006H10 gene | 2.2 | 2.1 | 2.0 |
| RBM3 | RNA binding motif protein 3 | 2.7 | 2.8 | 2.8 |
| 1300003D03RIK | RIKEN cDNA 1300003D03 gene | 2.2 | | 2.4 |
| CEBPB | CCAAT/enhancer binding protein (C/EBP), beta | 2.0 | | 2.3 |
| MT2 | metallothionein 2 | 2.2 | 2.1 | 2.3 |
| ORM2 | orosomucoid 2 | 1.7 | 1.7 | 2.0 |
| VNN1 | vanin 1 | 2.0 | 2.1 | |
| GTF2A2 | general transcription factor IIa, 2 (12 kD subunit) | 2.2 | | 2.4 |
| ITIH4 | inter alpha-trypsin inhibitor, heavy chain 4 | 1.8 | | 1.9 |
| ITIH3 | inter-alpha trypsin inhibitor, heavy chain 3 | 1.8 | 1.7 | 1.9 |
| NPN3 | neoplastic progression 3 | 2.2 | | 2.5 |
| U62673 | EST | −2.4 | −3.2 | |
| PAPSS2 | 3′-phosphoadenosine 5′-phosphosulfate synthase 2 | −2.0 | −2.3 | |
| TEMT | thioether S-methyltransferase | −2.2 | | −1.7 |
| TTR | transthyretin | −2.0 | −1.8 | |
| CBG | corticosteroid binding globulin | −3.4 | −2.8 | −2.8 |
| HSD11B1 | hydroxysteroid 11-beta dehydrogenase 1 | −2.1 | −1.9 | |
| LIFR | leukemia inhibitory factor receptor | −2.5 | −2.0 | −1.7 |
| LIFR | leukemia inhibitory factor receptor | −2.5 | −2.0 | −1.7 |
| HPGD | hydroxyprostaglandin dehydrogenase 15 (NAD) | −1.9 | −2.5 | |
| CBG | corticosteroid binding globulin | −3.5 | −2.8 | −2.8 |
| HAL | histidine ammonia lyase | −2.2 | −2.0 | −2.1 |

TABLE 3-continued

| Identifier | Gene Name | Ad-GIL-19 Mouse 49 Avg Fold Change | Ad-GIL-19 Mouse 51 Avg Fold Change | Ad-GIL-19 Mouse 52 Avg Fold Change |
|---|---|---|---|---|
| CYP2F2 | cytochrome P450, 2f2 | −2.5 | −2.3 | −1.7 |
| KEG1 | kidney expressed gene 1 | −2.9 | −2.2 | |
| AI266885 | EST | −4.7 | −3.1 | −2.4 |
| Called Present in only one animal | | | | |
| PAP | pancreatitis-associated protein | 9.2 | | |
| 1300007C21RIK | RIKEN cDNA 1300007C21 gene | 4.7 | | |
| REG2 | rat regenerating islet-derived, mouse homolog 2 | 9.8 | | |
| UNK_AE000664 | EST | 9.6 | | |
| SERINE/THREONINE-PROTEIN KI... | SERINE/THREONINE-PROTEIN KI. | 2.1 | | |
| 1300007C21RIK | RIKEN cDNA 1300007C21 gene | 3.8 | | |
| CRAT | carnitine acetyltransferase | 2.6 | | |
| AS2 | arylsulfatase A | 3.2 | | |
| 2310009M24RIK | RIKEN cDNA 2310009M24 gene | 2.0 | | |
| 2310004B05RIK | RIKEN cDNA 2310004B05 gene | 2.8 | | |
| REG1 | rat regenerating islet-derived, mouse homolog 1 | 2.3 | | |
| AW048468 | esterase 31 | 1.8 | | |
| PAP | pancreatitis-associated protein | 7.7 | | |
| SULT-X1 | sulfotransferase-related protein SULT-X1 | −2.6 | | |
| ES31 | esterase 31 | −1.8 | | |
| AW538652 | EST | | −1.9 | |
| GAMT | guanidinoacetate methyltransferase | −2.0 | | |
| SC5D | sterol-C5-desaturase (fungal ERG3, delta-5-desaturase) homolog (*S. cerevisae*) | | −1.9 | |
| GHR | growth hormone receptor | | −3.0 | |
| AI839995 | EST | −1.8 | | |
| 0610025L15RIK | RIKEN cDNA 0610025L15 gene | | −1.9 | |
| AGXT | alanine-glyoxylate aminotransferases | −2.5 | | |
| PAH | phenylalanine hydroxylase | −2.0 | | |
| IGFBP2 | insulin-like growth factor binding protein 2 | −2.5 | | |
| AI647632 | EST | −2.1 | | |
| AI647632 | EST | −2.1 | | |
| G6PC | glucose-6-phosphatase, catalytic | −2.2 | | |
| CYP17 | cytochrome P450, 17 | | −3.0 | |
| GSTA2 | glutathione S-transferase, alpha 2 (Yc2) | −2.3 | | |
| CYP26 | cytochrome P450, 26, retinoic acid | −9.0 | | |
| THRSP | thyroid hormone responsive SPOT14 homolog (*Rattus*) | −2.7 | | |
| FMO3 | flavin containing monooxygenase 3 | −2.6 | | |

Example 9

Effect of an Anti-IL-22 Antibody in an In Vivo Arthritis Model

The ability of the P3/1 monoclonal antibody to ameliorate symptoms in a collagen-induce arthritis (CIA) murine model was examined. Male DBA/1 (Jackson Laboratories, Bar Harbor, Me.) mice were used for all experiments. Antibody was administered prophylactically or therapeutically to DBA mice. In the therapeutic regimen, treatment was initiated if disease was observed for two consecutive days in a mouse.

Arthritis was induced with the use of bovine collagen type II (Chondrex, Redmond, Wash.). Bovine collagen type II (Chondrex, Redmond, Wash.) was dissolved in 0.1 M acetic acid and emulsified in an equal volume of CFA (Sigma) containing 1 mg/ml *Mycobacterium tuberculosis* (strain H37RA). 100 μg of bovine collagen was injected subcutaneously in the base of the tail on day 0. On day 21, mice were injected subcutaneously, in the base of the tail, with a solution containing 200 μg of bovine collagen in 0.1M acetic acid that had been mixed with an equal volume of Incomplete Freund's adjuvant (Sigma). Naïve animals received the same sets of injections, minus collagen. The dosing protocol is shown schematically in FIG. 1.

Mice were monitored at least three times a week for disease progression. Individual limbs were assigned a clinical score based on the index: 0=normal; P=prearthritic, characterized by focal erythema on the tips of digits; 1=visible erythema accompanied by 1-2 swollen digits; 2=pronounced erythema, characterized by paw swelling and/or multi digit swelling; 3=massive swelling extending into ankle or wrist joint; 4=difficulty in use of limb or joint rigidity. Thus, the sum of all limb scores for any given mouse yielded a maximum total body score of 16.

At various stages of disease, animals were euthanized, tissues were harvested and paws were fixed in 10% formalin for histology or 4% paraformaldeyde, pH 7.47, decalcified in 20% EDTA (pH 8.0) and embedded in paraffin for in situ hybridization. Using light microscopy the paws were scored on a 5-grade scoring method (0-4) to characterize the intensity and extent of arthritis. Inflammatory infiltrates were used for scoring in addition to other changes related to the inflammation, such as pannus formation, fibrous of the synovial membrane, articular cartilage erosin and/or subchondral bone destruction. Hisotology grades were determined using readings of individual paws: NAD=0 or nothing abnormal discovered; 1=Slight to moderate; 2: Mild to moderate; 3: Marked and 4: Massive.

Figure 2:
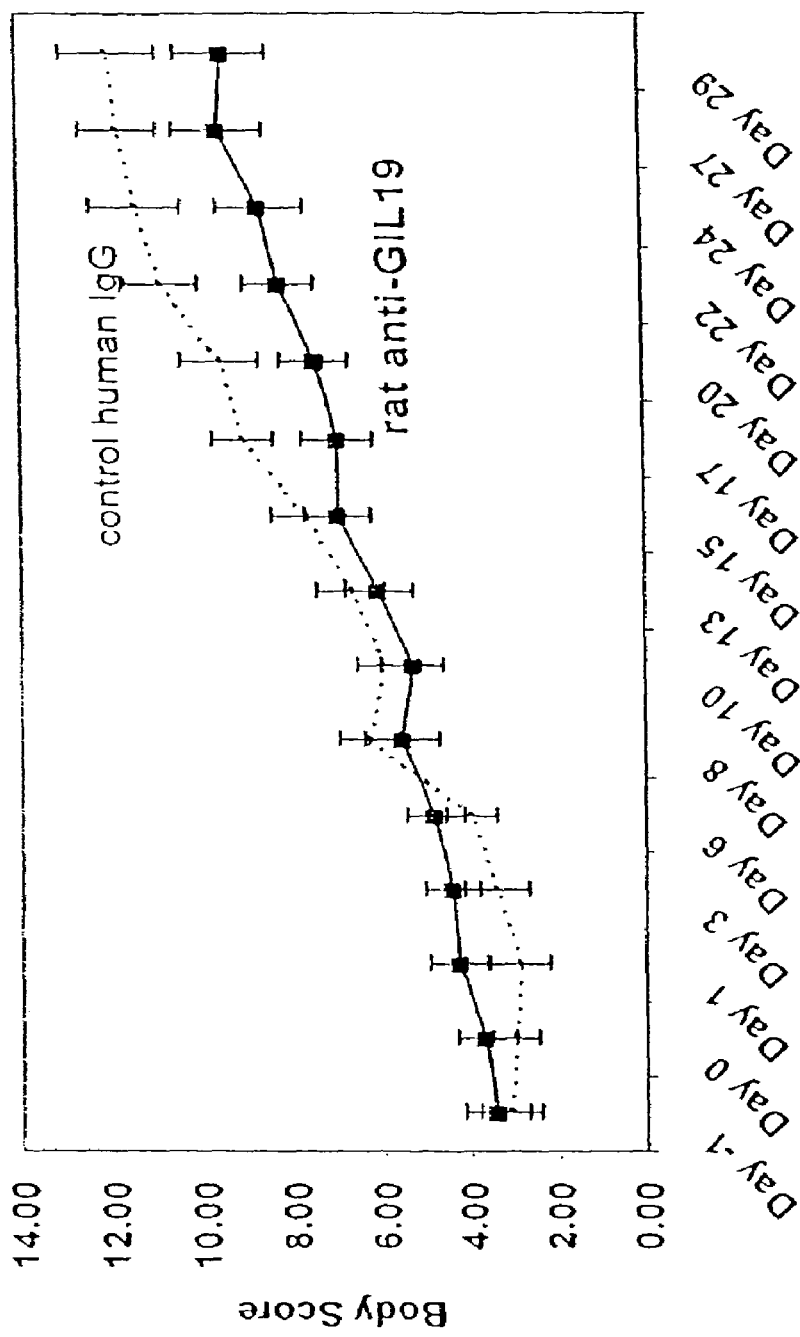
FIG. 2 is a graph showing body score following treatment of arthritic mice with IL-22 antibody or control using a therapeutic treatment regimen.

The effect of the therapeutic administration of IL-22 antibody is shown in FIG. 2. Body score is shown as a function of time. Mice administered anti-IL-22 antibody showed significantly decreased symptoms relative to mice administered control human IgG or PBS (data not shown).

Figure 3:
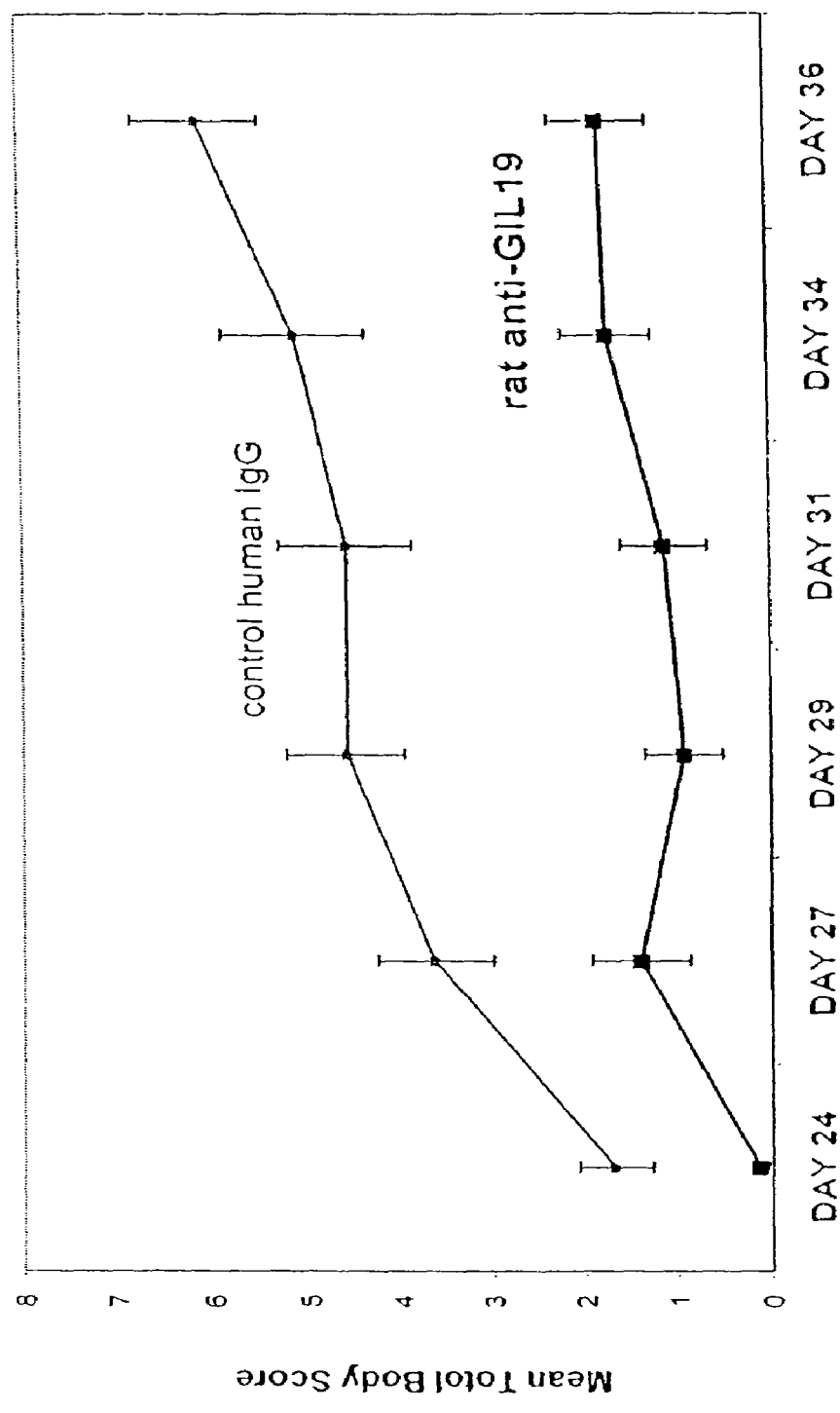
FIG. 3 is a graph showing body score following treatment of arthritic mice with IL-22 antibody or control using a prophylactic treatment regimen.
Figure 4:
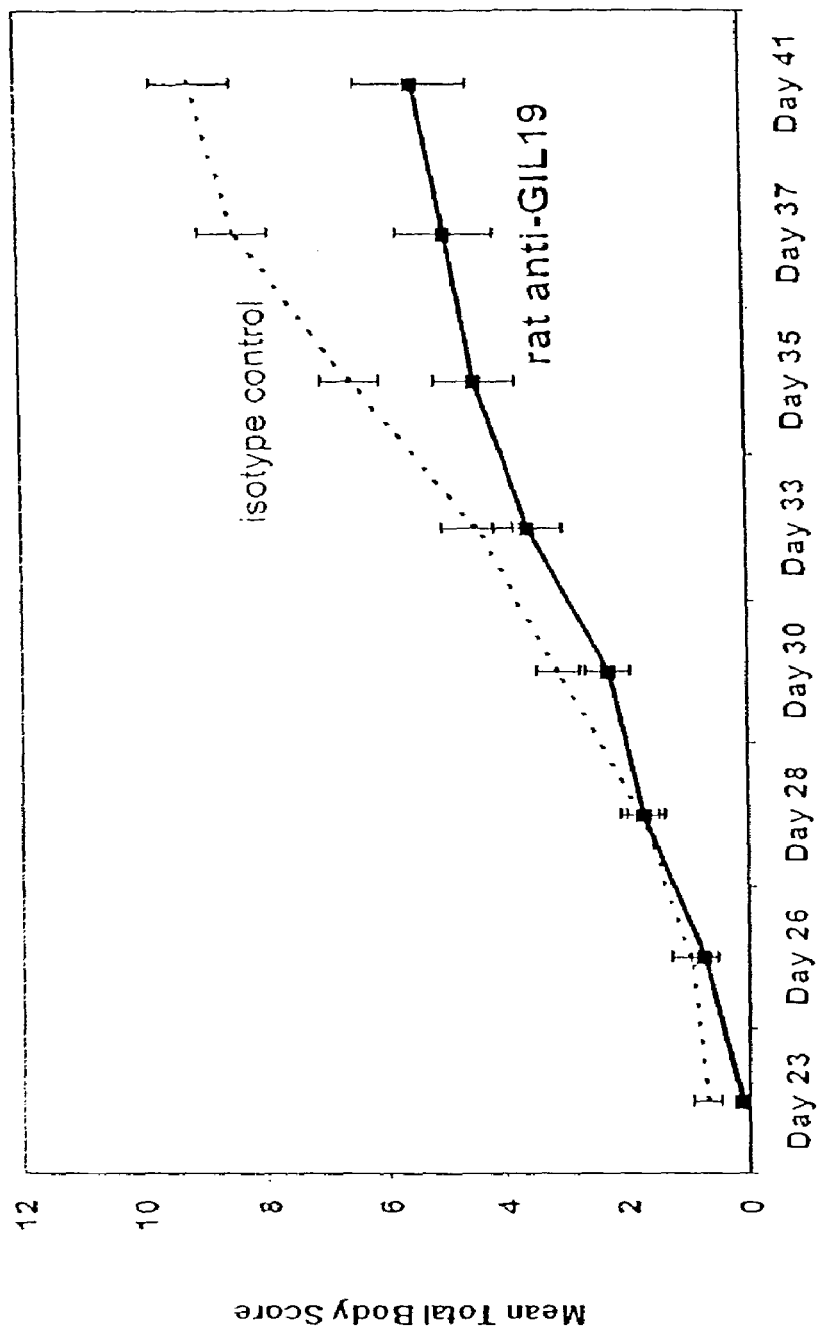
FIG. 4 is a graph showing body score following treatment of severely arthritic mice with IL-22 antibody or control.
Figure 5:
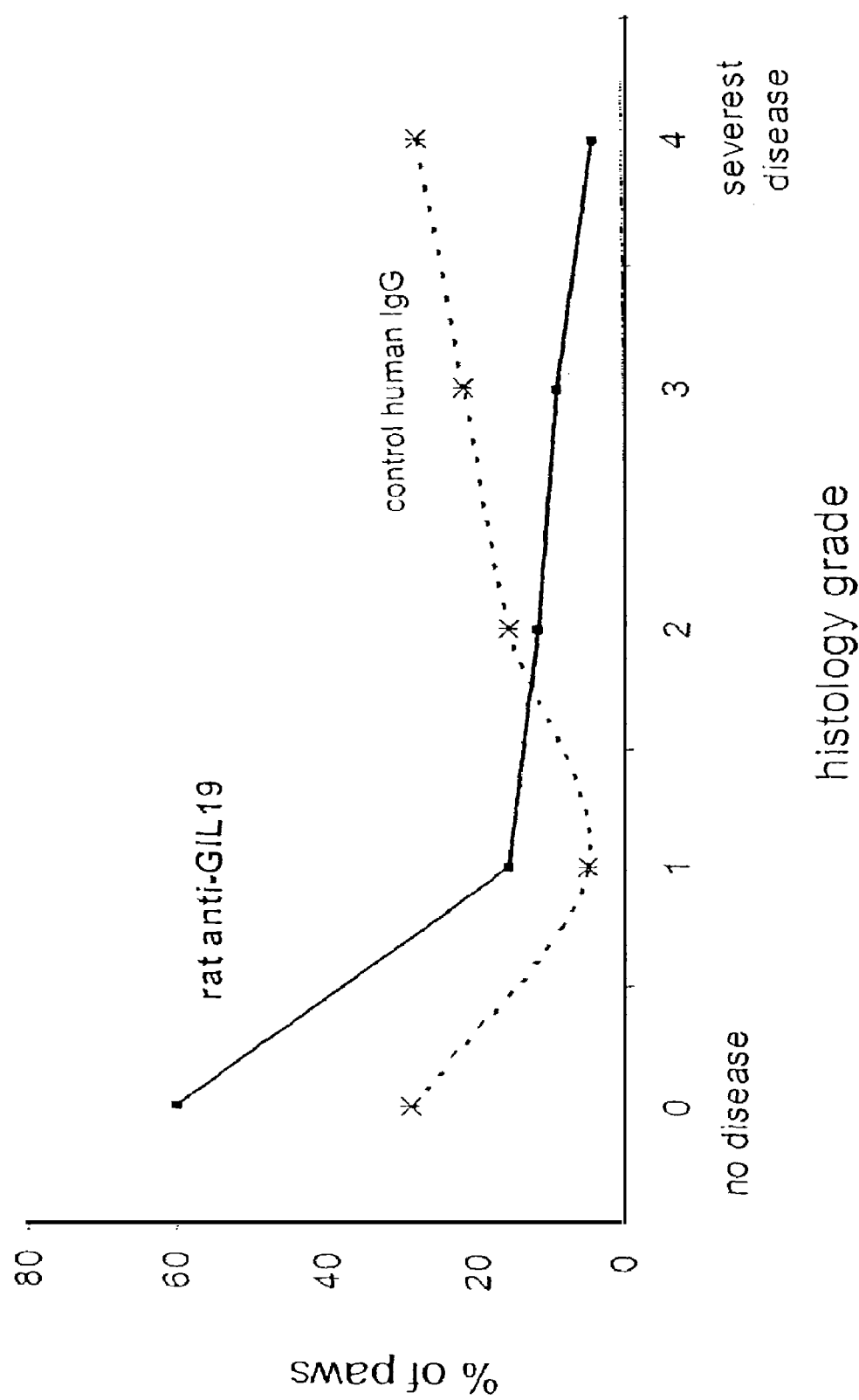
FIG. 5 is graph showing relative percentages of paws showing a given histology grade following with IL-22 antibody or control.

The effect of prophylactic administration of neutralizing IL-22 antibody is shown in FIGS. 3-5. Body score is shown as a function of time following administration of anti-IL-22 or control antibody. Mice administered anti-IL-22 antibody showed significantly decreased symptoms relative to mice administered control rat IgG or PBS (data not shown).

Body score was also examined in mice subjected to a separate prophylactic regimen. The results are shown in FIG. 4 as a function of time. Mice treated with control antibody demonstrated a significantly higher mean total body score than mice treated with anti-IL-22. Mice administered anti-IL-22 antibody showed significantly decreased symptoms relative to mice administered control rat IgG1 or PBS (data not shown).

The progression of disease in paws of mice subjected to the prophylactic regimen is shown in FIG. 5. Mice at day 36 were sacrificed, and the severity of disease in their paws examined. The paws were assigned a histology grade of 0 to 4, with 0 corresponding to no disease and 4 representing most severe disease. For rats injected with IL-22 antibody, over 60% had a histology grade of "0", while about 20% of the mice had a histology grade of "1". About 15% of the mice showed a histology grade of "2", and about 10% of the mice showed a histology grade of "3". A small percentage of mice showed a histology grade of "4". For mice injected with control antibody, about 30% showed a histology grade of "0", and about 5% of the mice showed a histology grade of "1". The remaining mice exhibited more severe pathology grades: about 18% showed a histology grade of "2", while 20% showed a pathology grade of "3", and the remaining mice showed a histology grade of "4". Mice administered anti-IL-22 antibody showed significantly decreased symptoms relative to mice administered control rat IgG1 or PBS (data not shown).

These results demonstrate that administration of IL-22 antibody either prophylactically or therapeutically significantly ameliorates symptoms of arthritis in an animal system.

Example 10

In Situ Hybridization of IL-22 Transcripts

The expression of IL-22 and IL-22 receptor sequences in various cell types of foot pads of arthritic mice was determined. Anti-sense IL-22 and IL-22 murine receptor riboprobes were produced by generating 2 independent PCR products from the corresponding transcripts. The oligonucleotides 5'-GACTGATAATACGACTCACTATAGGGCGAACAAT TTTGACTCCGATATTGTC CAAG-3' (SEQ ID NO:6) and 5'-AGGATGGAGACATCTGACTGCCCTACG-3' (SEQ ID NO:5) were used to generate for a IL-22 receptor sense probe and 5'-ACAATTTTGACTCCGATATTGTCCAAG (SEQ ID NO:7) and 3'-GACTGATAATACGACTCACTATAGGGCGAAGGAT GGAGACATCTGACTGCC CTACG-3' (SEQ ID NO:8) were used to generate for a IL-22 receptor antisense probe. Following PCR amplification probes were generated using T7 RNA polymerase and in vitro transcription.

A probe for IL-22 sequences was constructed by placing the following sequence in a plasmid and placing the sequence under the control of T7 and SP6 promoters to produce sense or anti-sense transcripts:

```
CAGCCATACATCGTCAACCGCACCTTTATGCTGGCCA (SEQ ID NO:9)

AGGAGGCCAGCCTTGCAGATAACAACACAGATGTCCG

GCTCATCGGGGAGAAACTGTTCCGAGGAGTCAGTGCT

AAGGATCAGTGCTACCTGATGAAGCAGGTGCTCAACT

TCACCCTGGAAGACGTTCTGCTCCCCCAGTCAGACAG

GTTCCA
```

T7 RNA polymerase binding sites were incorporated into the oligonucleotides to insert T7 binding sites at either the 5'end of the PCR product for sense riboprobe or the 3'end of the PCR product for antisense riboprobe. Digoxygenin labeled probes were prepared with the use of a DIG RNA labeling mix (Roche Diagnostics, Mannheim, Germany), as described by the manufacturer, and T7 RNA polymerase (Roche Diagnostics). IL-22 receptor mRNA-positive cells in the paw of CIA murine model were macrophages, fibroblasts, a subpopulation of lymphocytes, activated osteoblasts, synoviocytes and epidermis. No positive staining was seen in the control paws or with sense probes. mIL-22 mRNA positive cells were: neutrophils, macrophages, fibroblasts and Osteocytes. No staining was seen in the paw section treated with the sense probe and the control mouse paw stained with mIL-22 mRNA. In situ hybridization showed the presence of both the IL-22 receptor and cytokine in the paws of arthritic mice.

Example 11

Experimental Protocols for Examples 12-22

Recombinant IL-22, IL-22$R_{ECD}$, IL-10R2$_{ECD}$ and IL-22BP Fusion Proteins

A mammalian expression vector that encoded an N terminal His/Flag tag (GSGHHHHHHGSGDYKDDDDK (Terpe, K. (2003) *Applied Microbiology & Biotechnology* 60(5):523-33) fused to the mature end of human IL-22 (APISSHCRLD) was transfected into Chinese Hamster Ovary (CHO) cells that were further selected in methotrexate and the recombinant cytokine subsequently purified from conditioned media, all by standard methods (Terpe, K. (2003) supra; Kaufman, R. J. (1990) *Methods in Enzymology* 185:537-66; Kaufman, R. J. (1990) *Methods in Enzymology* 185:487-511; Hochuli, E. (1988) *Bio/Technology* 6:1321-1325). For use in ELISA, human IL-22 was biotinylated using EZ-Link™ Sulfo-NHS-Biotin kit as recommended by the manufacturer (Pierce, Rockford, Ill.). Purified recombinant murine IL-22 was prepared by comparable methods using an expression vector that encoded a fusion between an N terminal HIS/FLAG tag (GS-GHHHHHHGDYKDDDDK) and the mature N terminus of murine IL-22 (LPVNTRCKL). Cytokines were quantitated by $A_{280}$ absorbance, using the theoretical extinction coefficient derived from the amino acid composition. Human and murine IL-22 separates on SDS-PAGE gels at ~30-40 kD, either in the presence or absence of reductant (data not shown). It is extensively glycosylated; when treated with N-glycanase, IL-22 migrates at ~19 kD, near or at its theoretical molecular weight (data not shown).

The extracellular domains of IL-22R and IL-10R2, as defined by hydrophobicity plots, and IL22-BP were fused in-frame via a flexible joining linker to the Fc domain of human IgG1. Mammalian expression vectors were constructed that encode either human IL-22$R_{ECD}$ (TLPDRTWT is the C terminal sequence (Xie M. H. et al. (2000) *J Biol Chem* 275(40):31335-9; Kotenko S. V. et al. (2001) *J Biol Chem* 276(4):2725-32)), human IL-10R2$_{ECD}$ (THDETVPS is the C terminal sequence (Lutfalla, G. et al. (1993) Genomics 16(2):366-73)) or human IL-22BP (EERCVEIP is the C terminal sequence (Dumoutier, L. et al. (2001) *J Immunol* 166(12):7090-5; Kotenko, S. V. et al. (2001) *J Immunol* 166 (12):7096-103; Xu, W. et al. (2001) *Proc Natl Acad Sci* USA 98(17):9511-6) fused to a linker (AGSGSGSG) and then human IgG1 Fc (N terminal sequence of this domain starts at EPKSCDKT). Conditioned media containing each of these Fc fusion homodimers were prepared from stable CHO lines by standard methodologies (Kaufman, R. J. (1990) *Methods in Enzymology* 185:537-66; Kaufman, R. J. (1990) *Methods in Enzymology* 185:487-511). Conditioned media expressing both IL-22R-Fc and IL-10R2-Fc were produced by either transient transfection of the IL-10R2-Fc fusion expression vector into a stable IL-22R-Fc expressing CHO line or by co-amplification of these fusion receptors. Conditioned media (CM) was used as the source of all Fc fusion receptors.

Total Fc fusion in CM was quantitated with an anti-human IgG sandwich ELISA, using 1 ug/ml goat anti-human IgG (Southern Biotech Associates, Inc., Birmingham, Ala.) as the coating antibody, 1/10,000 diluted goat anti-human IgG HRP (Southern Biotech Associates, Inc., Birmingham, Ala.) as the detecting antibody and an irrelevant purified Fc fusion protein as the standard, quantitated by its absorbance at $A_{280}$. A detailed protocol for a standard ELISA is given below.

The integrity and composition of Fc fusion homodimers and heterodimers was evaluated in the presence or absence of β-mercaptoethanol (FIG. 7A), using standard SDS acrylamide gel electrophoretic methods and either 1:5000 dilution of goat anti-human IgG-HRP (Southern Biotech Associates, Inc., Birmingham, Ala.), 1 ug/ml rabbit anti-IL-22R (ProSci, Poway, Calif.) or 0.2 ug/ml goat anti-hIL-10R2 (R&D Systems, Minneapolis, Minn.) as detecting reagents. Note that both the IL-22R and IL-10R2 antibodies will detect both chains of the respective homodimer and one chain of the heterodimer.

For the specific detection of IL-22R-Fc/IL-10R2-Fc heterodimers, a sandwich ELISA was established, using 0.5 ug/ml rabbit anti-hIL-22R (ProSci, Poway, Calif.) as the coating antibody and 0.5 ug/ml biotinylated goat anti-hIL-10R2 (R&D Systems, Minneapolis, Minn.) as the detector.

IL-22 Antibodies

Monoclonal antibodies directed against IL-22 were generated by first immunizing LOU rats (Harlan, Harlan, Mass.) with murine and then human cytokine. Rat spleens were fused with the mouse myeloma cell line P3X63Ag8.653 (ATCC, Rockville, Md.) and hybridoma cell lines were generated using standard techniques (Goding J. *Production of Monoclonal Antibodies. In: Monoclonal Antibodies: Principles and Practices*. 3rd ed. San Diego: Academic Press; 1996. p. 141-180). Anti-hIL-22 secreting lines were initially identified by ELISA, using 1 ug/ml hIL-22 coated plates and 1/5000 diluted HRP conjugated goat anti-rat IgG (Pierce, Rockford, Ill.) as the detector. Ab-02 and Ab-04 have been previously described as IL-22 antibody P3/3 and P3/2, respectively (See Example 5 above). The antibodies were purified from ascites by standard methods. For conversions to molarity, 150 ng/ml is defined as 1 nM antibody.

IL-22 Cytokine/Receptor Fc Binding ELISA

Two standard formats were used to study the interaction between IL-22 and the receptor Fc fusions. The results shown in FIGS. 6A, 8A-8B, 9A-9B, 10B-10C and 11A-11C were obtained from ELISA assays where receptor Fc from CHO CM were first immobilized via an anti-hIgG coat. Flat bottom, 96-well ELISA plates (Costar, Cambridge, Mass.) were coated overnight at 4° C. with 100 μl goat anti-human IgG antibody (Southern Biotech Associates, Inc., Birmingham, Ala.) at 1 μg/ml in 0.1 M sodium carbonate buffer (pH 9.6). The plates were washed twice with 200 μl phosphate-buffered saline containing 0.05% Tween 20 (PBS-T), blocked with 100 μl 1% BSA (Sigma, St. Louis, Mo.) in PBS-T for 1 hour and washed three times. Following by one hour sequential incubations (100 ul), each separated by three washes, were then employed: a given receptor fusion(s) at a fixed concentration or serially diluted, biotinylated IL-22 (bio-IL-22) at a fixed concentration or serially diluted, and then 1/10,000 dilution of streptavidin-horse radish peroxidase (HRP) (Southern Biotech Associates, Inc., Birmingham, Ala.). After a final set of washes, 100 μl of TMB Microwell peroxidase substrate (BioFX, Owings Mills, Md.) was added for 20 minutes and the reaction stopped with 100 μl 2N $H_2SO_4$. Colorimetric detection of the peroxidase product was done at 450 nm in a Molecular Devices (Sunnyvale, Calif.) microplate reader.

Figure 9A:
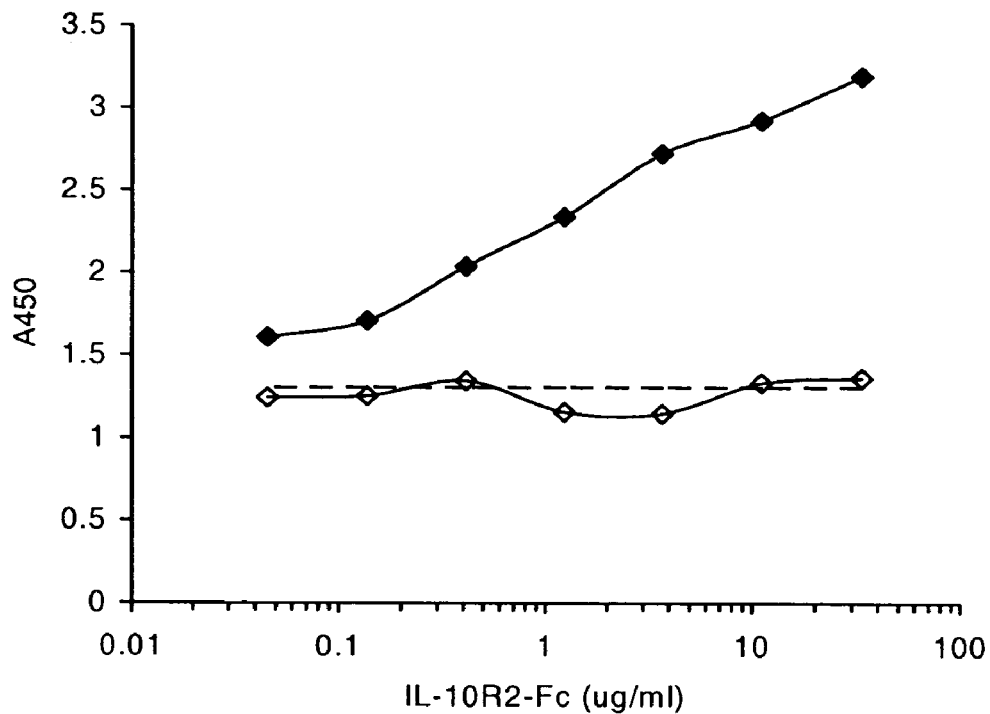
FIGS. 9A-9B are linear representations of an interaction between IL-10R2 and IL-22/IL-22R. The effect of adding IL-10R2-Fc homodimers was evaluated either before, with or following the addition of bio-IL-22.
Figure 9B:
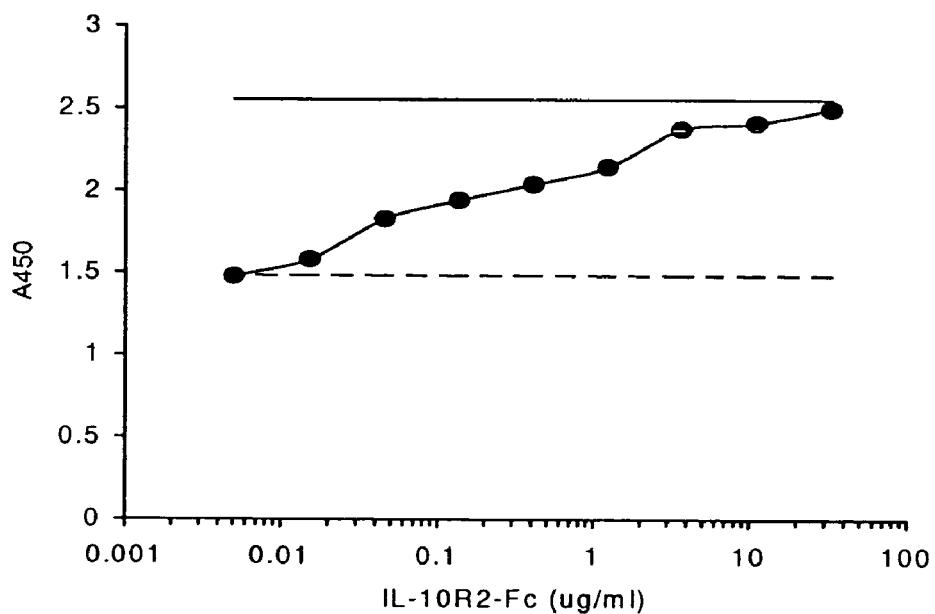

For certain ELISA assays of the above format where both the receptor Fc and bio-IL-22 are at a fixed concentration, IL-10R2-Fc was added at various concentrations either before or with bio-IL-22 (FIG. 9A) or after the bio-IL-22 (FIG. 9B). For other ELISA assays of the above format where the indicated receptor Fc and bio-IL-22 are also at a fixed concentration, antibodies (FIG. 10B-10C., 11C) or IL-22BP (FIG. 11A-11B) were added at various concentrations after a pre-incubation with the bio-IL-22 for 30 minutes. For ELISA assays in which the recruitment of IL-10R2-Fc to the IL-22/IL-22R complex was detected directly (data not shown, experimental design of FIG. 9A), non-biotinylated IL-22 was added to the ELISA and either polyclonal goat anti-hIL-10R2 or a mouse monoclonal anti-hIL-10R2 (R&D Systems, Inc, Minneapolis, Minn.) was used as detector.

Figure 6A:
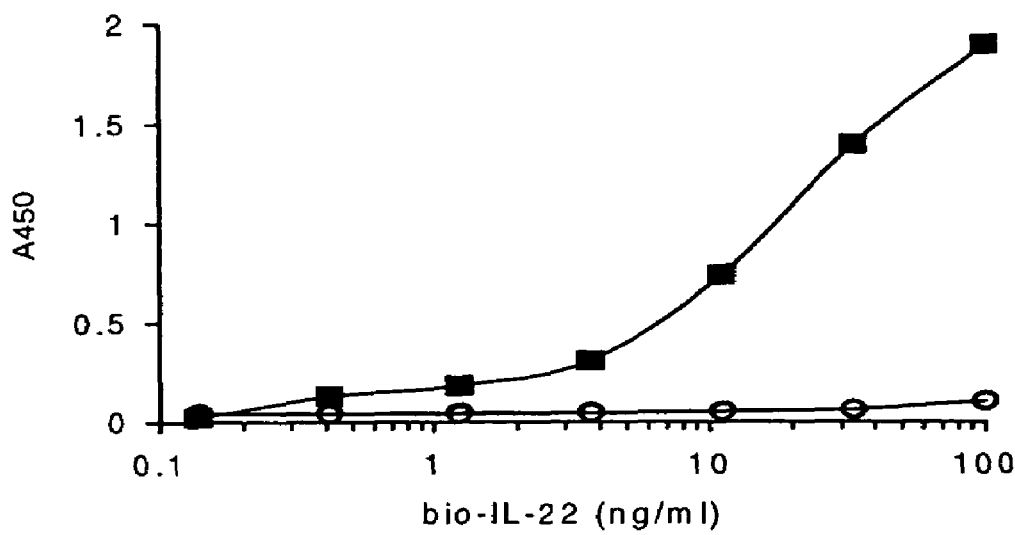
FIGS. 6A-6B are linear representations of an interaction between IL-22 and IL-22R and IL-10R2.
Figure 6B:
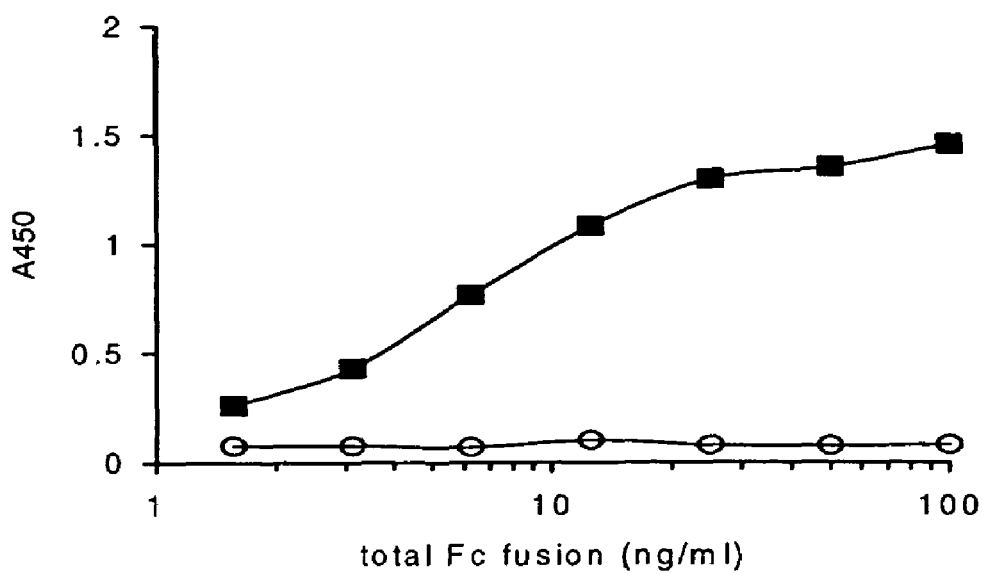

FIG. 6B depicts the results form an ELISA assay performed in the opposite format, whereby 100 □l of 1 □g/ml biotinylated IL-22 was added to Reacti-Bind 96 well streptavidin-coated plates (Pierce, Rockford, Ill.) for one hour. After washing, Fc fusion receptor was added at various concentrations to the plates for one hour, washed and then detected with goat anti-human IgG-HRP. In FIG. 6A, fifty ng/ml of total Fc in conditioned media (CM) from CHO cells expressing either IL-22R-Fc (■) or IL-10R2-Fc (O) was captured onto anti-human IgG coated wells. Biotinylated IL-22 (bio-IL-22) at various concentrations was then added to the wells. Bound bio-IL-22 was subsequently detected using streptavidin-HRP. In FIG. 6B, bio-IL-22 (1 µg/ml) was captured onto streptavidin plates. Various concentrations of either IL-22R-Fc (■) or IL-10R2-Fc (O) in diluted CHO. CM was then added to the wells. Bound receptor Fc was subsequently detected using goat anti-human IgG-HRP.

Inhibition of STAT3 Phosphorylation Using Anti-IL-22 Antibodies

HepG2 cells (ATCC, Rockville, Md.) were cultured in Dulbecco's modified essential medium (DMEM) supplemented with 10% fetal calf serum, using 6 well tissue culture plates (Corning, Corning, N.Y.) seeded at $4 \times 10^5$ cells/well. After 24 hours, fresh media was added, with or without 50 ng/ml human IL-22, for 25 minutes. Where antibody was tested for neutralization potency, the cytokine and antibody was pre-incubated for 30 minutes at room temperature. Cells were lysed by adding 200 µl/well cell lysis buffer (New England Biolabs, Beverly, Mass.). The total protein concentration in cell lysate was measured by BCA assay (Pierce, Rockford, Ill.). Ten microgram of protein was separated on a 4-20% SDS-polyacrylamide gel (Invitrogen, Carlsbad, Calif.) and subsequently blotted at room temperature overnight onto a nitrocellulose membrane (Amersham, Braunschweig, Germany). The phosphorylated STAT3 was detected using the p-stat3 Tyr705 antibody kit (New England Biolabs, Beverly, Mass.). An ECL detection system was used for expression of chemiluminescence as recommended by the manufacturer (Pierce, Rockford, Ill.).

Example 12

IL-22 Binds IL-22R and has no Detectable Affinity for IL-10R2

IL-22 binding to the extracellular domain (ECD) of IL-22R and IL-10R2 was evaluated using two ELISA formats. In the first version, receptor-Fc fusion proteins were immobilized via the Fc domain on anti-human IgG coated plates. Biotinylated IL-22 was then added and detected with streptavidin-HRP. FIG. 6A is a linear graph showing that bio-IL-22 binds to the immobilized IL-22R-Fc, and not detectably to IL-10R2-Fc. In the reverse format, bio-IL-22 was first immobilized onto strepavidin coated-plates. Receptor-Fc were then added and detected with HRP-conjugated, anti-hIgG. As shown in FIG. 6B, soluble IL-22R-Fc, and not IL-10R2-Fc, binds to immobilized bio-IL-22. A slight signal above background (non-specific Fc fusion) was observed when IL-10R2-Fc was added to this assay format at higher concentrations (3-10 ug/ml; data not shown), suggesting that IL-10R2-Fc has a very low avidity for the immobilized bio-IL-22. In summary, this first set of ELISA experiments indicates that there is a relatively strong interaction between IL-22 and IL-22R, while IL-10R2-Fc has only a slight avidity for IL-22.

Example 13

Preparation and Characterization of IL-22R-Fc and IL-10R2-Fc Homodimers and Heterodimers The following experiments were conducted to evaluate whether the extracellular domain of IL-10R2 binds to IL-22 when juxtaposed with IL-22R-Fc. Since it was observed that IL-22R-Fc is secreted poorly from amplified CHO lines (~50-100 ng/ml) while IL-10R2-Fc is secreted quite well (~10 ug/ml), it is believed that IL-10R2-Fc might be able to facilitate the secretion of IL-22R-Fc. A CHO line expressing IL-22R-Fc was transiently transfected with an IL-10R2-Fc expression vector. The introduction of this plasmid increased the expression of IL-22R-Fc two-four fold. Stable lines were subsequently established that co-express both Fc fusion receptor chains.

Monomeric IL-22$R_{ECD}$-Fc and IL-10R2$_{ECD}$-Fc fusions were determined to have molecular weights of ~60 kD and ~85 kD, respectively. Reduced and non-reduced conditioned media (CM) from CHO cells expressing either or both receptor Fc fusions was separated on SDS-PAGE gels and blotted to a membrane which was then probed with polyclonal antibodies directed against either human IgG Fc, IL-22R or IL-10R2. More specifically, in FIG. 7A, conditioned media from CHO cells expressing either IL-22R-Fc, IL-10R2-Fc or both receptor Fc were separated on 8% polyacrylamide gels under both reduced (+βME) and non-reduced (-βME) conditions and transferred to membrane blots. Western blots were carried out using any of anti-human IgG1, anti-hIL-22R or anti-hIL-10R2 antibodies. For anti-hIgG detection of a blot, 4 ng total Fc fusion in CM was loaded in each lane. For anti-IL-22R and anti-IL-10R2 antibody detection, 16 ng total Fc fusion in CM from co-expressing CHO was used. In FIG. 7B, conditioned media from CHO cells expressing either IL-22R-Fc (■), IL-10R2-Fc (■) or both (▲) were added to ELISA plates coated with rabbit anti-human IL-22R antibody. A 1:1 mixture of the two homodimers was also added as a control (Δ). The bound receptors were detected using a biotinylated goat anti-human IL-10R2 antibody, followed by streptavidin-HRP.

Under reducing conditions (+βME, FIG. 7A), IL-22R and IL10R2-Fc CHO lines secrete a human Fc fusion protein with a distinct molecular weight. Detection with receptor chain-specific antibodies confirms that the ~60 kD species is IL-22R-Fc while the ~85 kD species is IL-10R2-Fc. Both of these mature receptor fusion proteins have theoretical molecular weights of ~51 kD. IL-22R-Fc, with four potential N-linked glycosylation sites, is predicted to be less extensively glycosylated during its passage through a CHO cell, than IL-10R2-Fc, with five potential N-linked sites. IL-10R2-Fc appears to have more extensive post-translational modifications. This analysis, under reducing conditions, also shows that co-expressing CHO cells secrete both Fc fusions. The data derived from the anti-hIgG detection panel suggest that IL-10R2-Fc is expressed at a higher level than IL-22R-Fc.

CHO cells expressing both receptor Fc fusions secrete predominantly IL-22R/IL-10R2-Fc heterodimer and IL-10R2-Fc homodimer. Since these receptor Fc fusions have distinct molecular weights, analysis of the CM by non-reducing SDS-PAGE (–βME, FIG. 7A) enables the detection of receptor Fc fusion heterodimer that separates on gels between the two homodimers. Under these conditions, both IL-22R/IL-10R2-Fc heterodimer and IL-10R2-Fc homodimer were detected with anti-hIgG in the CM from co-expressing CHO cells. In contrast, IL-22R-Fc homodimer is poorly detected. The IL-22R antibody detection panel, under non-reducing conditions, demonstrates that co-expressing CHO do secrete IL-22R-Fc homodimer, but substantially less than the heterodimer. Taken together, the results shown in FIG. 7A indicate that IL-22R/IL10R2-Fc transfected CHO secrete covalent IL-22R/IL-10R2-Fc heterodimer and IL-10R2-Fc homodimer and very little IL-22R-Fc homodimer.

The presence of heterodimers in the CM from CHO cells was verified by sandwich ELISA, using antibodies specific for each chain of the heterodimer. Conditioned media was added to wells coated with an IL-22R polyclonal antibody and bound protein was then detected with a biotinylated IL-10R2 polyclonal antibody. This ELISA format will detect only molecules where there is a stable association between the IL-22R and IL-10R2 epitopes. CM from CHO expressing either IL-22R-Fc or IL-10R2-Fc alone or these CM mixed together gave no detectable signal in this ELISA format. A signal was obtained only from CHO cells that co-expressed IL-22R-Fc and IL-10R2-Fc. This observation demonstrated, along with the data of FIG. 7A, that CHO cells expressing both Fc fusion receptors secrete heterodimers that contain a covalent association between the IL-22R$_{ECD}$ and IL-10R2$_{ECD}$ Fc monomeric chains.

Figure 7A:
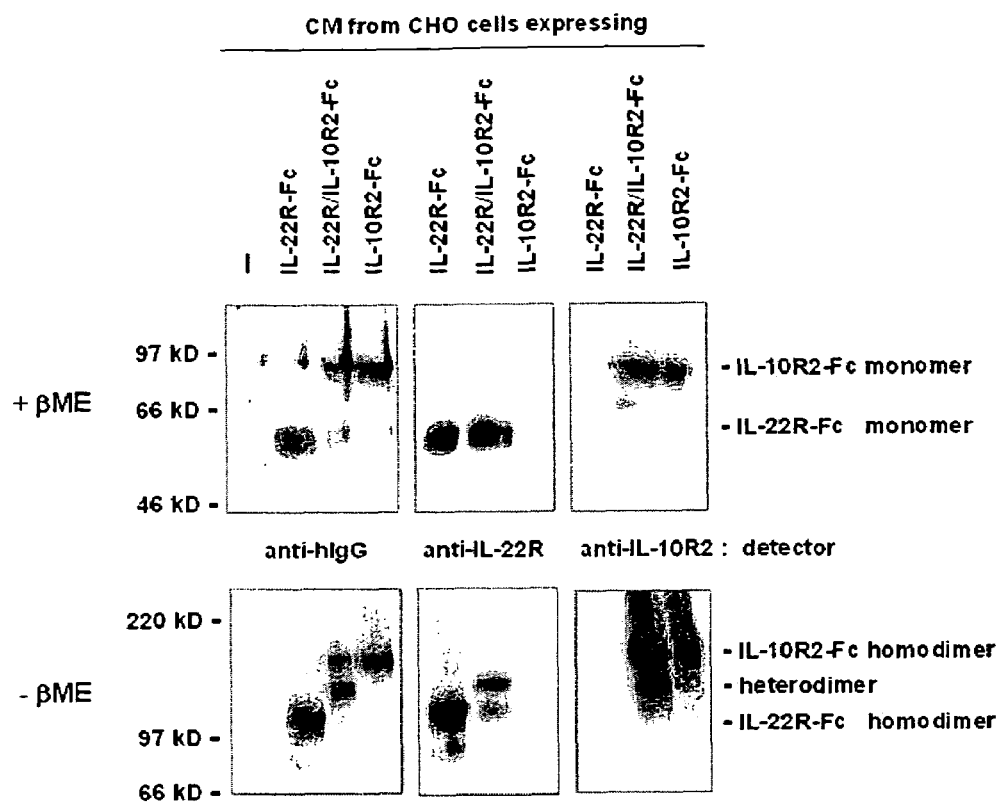
FIGS. 7A-7B show the characterization of receptor Fc fusion in CHO conditioned media.
Figure 7B:
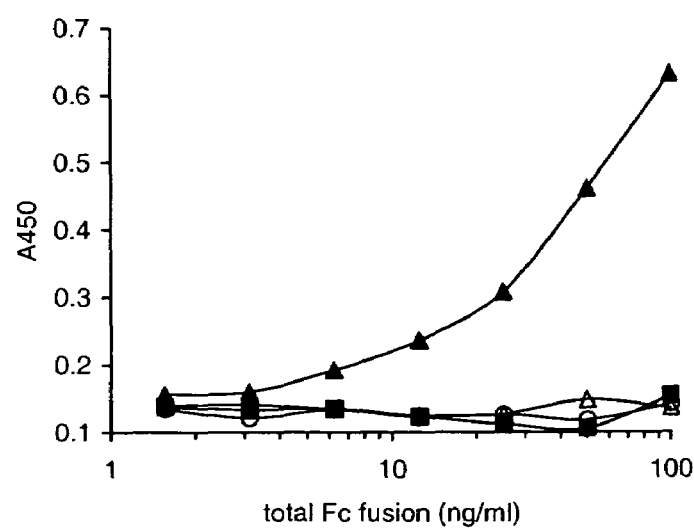

In summary, the results shown in FIGS. 7A-7B indicate that the receptor Fc fusions are secreted from CHO cells as homodimers and heterodimers. The IL-22R/IL-10R2-Fc co-expressing CHO cells secrete mostly heterodimer and IL-10R2-Fc homodimer.

Example 14

IL-22 Exhibits Enhanced Binding to Juxtaposed IL-22R/IL-10R2 Receptor Fc Chains

Figure 8A:
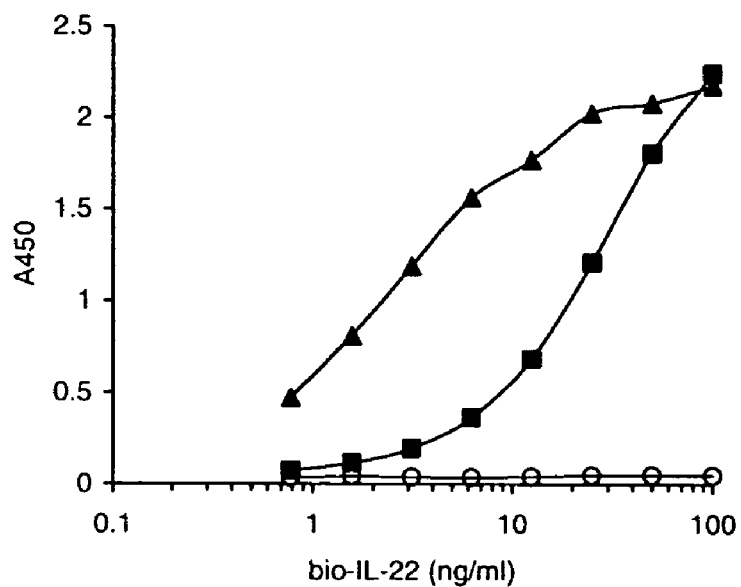
FIGS. 8A-8B are linear representations of an interaction of IL-22 with both IL-22R and IL-10R2, either as Fc fusion heterodimers or as randomly juxtaposed homodimers.

IL-22 binding to the ECD of IL-22R and IL-10R2 secreted as Fc heterodimer was then evaluated. A fixed concentration of total Fc fusion protein from CM was first immobilized via the Fc domain on anti-human IgG coated plates. The ability of cytokine to bind was then evaluated using various concentrations of bio-IL-22 as the detector (FIG. 8A). As in FIG. 6A, IL-22R-Fc and IL-10R2-Fc homodimers give a signal and no detectable signal, respectively. The most efficient bio-IL-22 binding, however, was obtained with immobilized receptor Fc from CM of co-expressing CHO cells: eight fold less bio-IL-22 was needed than for a comparable signal with immobilized IL-22R-Fc homodimer. Since binding of IL-10R2 Fc homodimer component to IL-22 is undetectable under these conditions (FIG. 6A, 8A), the enhanced binding of IL-22 by Fc protein from CM of co-expressing CHO must be due to the IL-22R/IL-10R2-Fc heterodimer component. Again, very little IL-22R-Fc homodimer is secreted by these co-expressing CHO cells (FIGS. 7A-7B). The stronger potency of the heterodimer for binding IL-22 is emphasized by the fact that less immobilized heterodimer relative to IL-22R-Fc homodimer was used in the experimental design of FIG. 8A. Since a fixed amount of total Fc was added to the wells, the CM containing heterodimer, in contrast to the IL-22R-Fc homodimer CM, is diluted by other Fc components. It was concluded that IL-22R/IL-10R2-Fc heterodimer gives the best binding signal, indicating an IL-22 binding role for the ECD of IL-10R2. Since IL-10R2 homodimer alone cannot bind IL-22, these results also indicate that IL-10R2's affect on binding IL-22 requires the presence of IL-22R.

Randomly apposed IL-22R and IL-10R2 ECD can also bind IL-22 more efficiently than IL-22R-Fc homodimers. For the experiment of FIG. 3B, 1:1 mixtures of CM were prepared, containing equal amounts of IL-22R-Fc homodimer and either IL-10R2-Fc homodimer or an irrelevant Fc homodimer. The mixtures of Fc fusion, as well as CM that contains heterodimer, were serially diluted and then immobilized at given total Fc concentrations onto anti-human IgG coated plates. The ability of cytokine to bind was then evaluated using a fixed concentration of bio-IL-22 as the detector. The results of FIG. 8B indicate that a mixture of IL-22R-Fc and IL-10R2-Fc homodimers binds bio-IL-22 with 2-3 fold greater efficiency than a mixture of IL-22R-Fc and irrelevant Fc homodimers. This observation indicates that the IL-22R and IL-10R2 receptor chains do not need to be covalently linked for IL-10R2-Fc to facilitate its function in this ELISA-based format. If the appropriate physical juxtaposition occurs during the random coating of the two homodimers together, then enhanced binding of biotinylated IL-22 is detected relative to a mixture of IL-22R-Fc and irrelevant Fc homodimers. This enhanced signal is more pronounced at higher concentrations of the total Fc, where it's more likely that IL-22R and IL-10R2 ECD will be apposed adjacent to each other. In contrast, the covalent association between the receptor Fc of the heterodimer gives a concentration-independent juxtaposition of the ECD of these receptors and thus the strongest signal at any concentration of total Fc. In summary, the results shown in FIGS. 8A-8B indicate that the ECD of IL-22R is required for the detection of IL-10R2's role in IL-22 binding. Enhanced binding of IL-22 is detected when both ECD are present.

Example 15

Figure 8B:
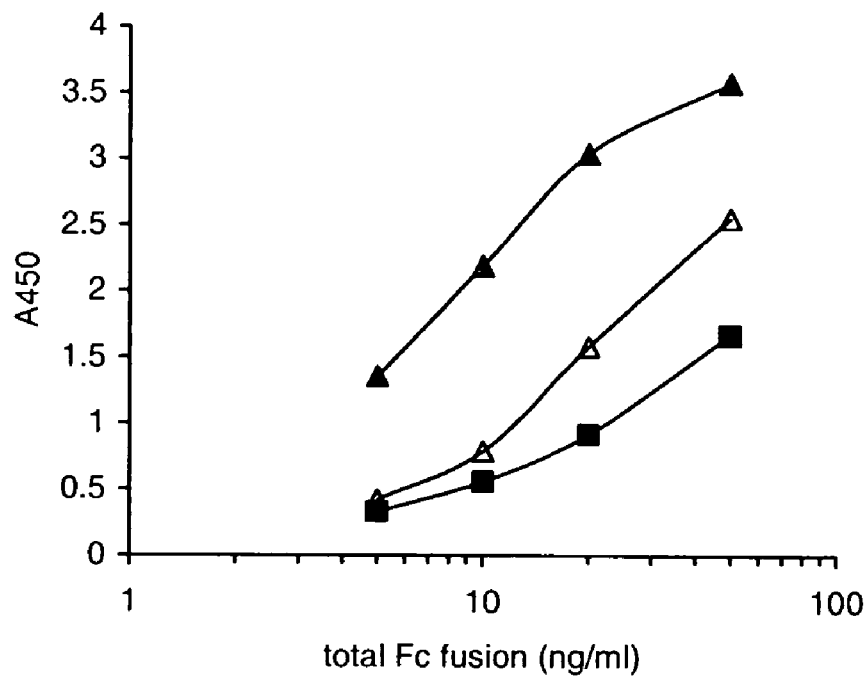

The Extracellular Domain (ECD) of IL-10R2 Effects the Stabilization of an Initial Interaction Between IL-22 and the Extracellular Domain of IL-22R The IL-22 binding function of IL-10R2 requires the presence of IL-22R (FIGS. 8A-8B). To evaluate further IL-10R2's temporal role in the development of an IL-22 cytokine receptor complex, the ELISA format was modified by adding IL-10R2-Fc homodimer after the IL-22R-Fc homodimer. The effect of adding IL-10R2-Fc homodimers could now be evaluated either before, with or following the addition of bio-IL-22. More specifically, in FIG. 9A, fifty ng/ml of IL-22R-Fc from CM was captured onto anti-human IgG coated wells. Wells were then blocked with 100 μg/ml human IgG. Bio-IL-22 (30 ng/ml) was then added to the wells. Bound bio-IL-22 was subsequently detected using streptavidin-HRP (broken line). Various concentrations of IL-10R2-Fc and biotinylated IL-22 (30 ng/ml) were also added together and then bound bio-IL-22 detected (♦). Various concentrations of IL-10R2-Fc from CM were also added first, incubated, plates washed and then 30 ng/ml bio-IL-22 subsequently added to the wells and bound bio-IL-22 detected (◇). The IL-10R2-Fc was serially diluted in 100 ug/ml hIgG. In FIG. 9B, fifty ng/ml of IL-22R-Fc from CM was captured onto anti-human IgG coated wells. Bio-IL-22 (30 ng/ml) was then added to the wells. Bound bio-IL-22 was then detected immediately after, using streptavidin-HRP (solid line). Bound bio-IL-22 was also detected after an additional 1 hour incubation with either PBS-1% BSA (broken line) or various concentrations of IL-10R2-Fc (•).

For the experiment of FIG. 9A, a fixed amount of IL-22R-Fc fusion homodimer was immobilized via its Fc on anti-human IgG coated plates. Human IgG (100 ug/ml) was then added to occupy or block still available anti-human IgG antibody on the plate. A fixed concentration of bio-IL-22 gives a signal (~1.25), bound to the plate through its interaction with IL-22R's ECD. If IL-10R2-Fc homodimer, serially diluted in hIgG, is added prior to the addition of bio-IL-22, there is no impact on the amount of bio-IL-22 subsequently bound to the plate. These observations suggest that the ECD of IL-22R-Fc and IL-10R2-Fc homodimers are unable to effect alone a stable association with each other that is subsequently detected by an enhancement of IL-22 binding. Rather, IL-10R2 requires the presence of IL-22, as well as IL-22R, in order to effect its cytokine binding enhancement. In the experiment of FIG. 9A, if IL-10R2-Fc is added with the bio-IL-22, there is now an IL-10R2 dose-dependent increase in the amount of bio-IL-22 that is bound to the IL-22R. Again, the addition of IL-10R2-Fc cannot effect enhancement if incubated with the immobilized IL-22R-Fc before the addition of bio-IL-22.

In consideration of both the IL-22 (FIG. 9A) and IL-22R (FIG. 8) prerequisite for IL-10R2's effect on cytokine binding, it was directly determined whether these requirements constitute an interaction between IL-22 and IL-22R. For the experiment of FIG. 9B, a fixed amount of IL-22R-Fc fusion homodimer was immobilized via its Fc on anti-human IgG coated plates. The addition of a fixed concentration of bio-IL-22 gives a signal (~2.5), bound to the plate through its interaction with IL-22R's ECD. Instead of detecting bio-IL-22 signal immediately, it was also detected after subsequent washes and a further incubation. When first bio-IL-22 and then 1% BSA is incubated in the wells, 0.6 (i.e. 1.5/2.5) of the original signal is detected, indicating that some of the bio-IL-22 was released from the immobilized IL-22R-Fc homodimer during the additional incubation with 1% BSA. In contrast, when first bio-IL-22 and then increasing concentrations of IL-10R2-Fc homodimer is added to the wells, more bio-IL-22 signal is detected, approaching the signal level obtained immediately after the bio-IL-22 incubation. These results indicate that IL-10R2's function in IL-22 binding requires an interaction between IL-22 and IL-22R. The addition of IL-10R2 to the wells, after the IL-22 incubation, induces the formation of a complex that has a slower off-rate for IL-22 than IL-22R alone.

Taken together, the results shown in FIGS. 6, 8 and 9 suggest a temporal model for the binding of IL-22 by the ECD of IL-22R and IL-10R2 receptor chains. IL-22 first binds to IL-22R. IL-10R2 then binds to IL-22/IL-22R, furthering stabilizing the IL-22 within the cytokine receptor complex (summarized in the schematic of FIG. 12).

Example 16

Two Distinct Surfaces of IL-22 Are Required for the Respective Interaction with the IL-22R and IL-10R2 ECD Two rat monoclonal antibodies, Ab-02 and Ab-04, were generated and shown to bind to human IL-22 (Example 5). These antibodies were tested for their ability to block IL-22-dependent signal transduction. IL-22 effects the phosphorylation of the STAT3 transcription factor in cell lines that express both IL-22R and IL 10R2 receptor chains (e.g. HEPG2)(Dumoutier L. et al. (2000) *Proc Natl Acad Sci USA* 97(18):10144-9). If these antibodies neutralize IL-22, then less P-STAT3 should be detected in lysates of cells. For the experiment of FIG. 10A, serially diluted antibody was pre-incubated with a fixed concentration of IL-22 in cell media. This media, including IL-22 complexed with antibody, was then applied to HEPG2 cells. Cell lysates were subsequently prepared, protein separated by gel electrophoresis, transferred to a membrane, which was incubated with an antibody specific for P-STAT3. More specifically, human IL-22 (50 ng/ml) was pre-incubated for 30 minutes at 37 C with various concentrations of Ab-02 or Ab-04 in cell media, the media then added to HepG2 cells and the cells incubated for 25 minutes. Cell lysates were then analyzed by Western blot using an anti-phospho-STAT3 antibody. Cells incubated with IL-22 alone (+) or without IL-22 (−) were included as positive and negative control, respectively. Both of these antibodies are able to block IL-22's activity on cells: with increasing concentration of antibody, the detection of P-STAT3 decreases. However, these antibodies differ in their potency: Ab-02 and Ab-04's $ND_{50}$ are ~33 nM and ~0.4 nM, respectively. In summary, the results shown in FIG. 10A indicate that both antibodies bind to a surface(s) on IL-22 important for this cytokine's ability to signal into a cell.

If each antibody neutralizes IL-22 by inhibiting its interaction with receptor chains, then Ab-02 and Ab-04 define IL-22 epitope(s) required for cytokine receptor interaction. The antibodies were evaluated in the cytokine-receptor binding ELISA to determine how these antibodies affect IL-22 binding. For the experiment of FIG. 10B, a fixed amount of IL-22R-Fc homodimer was immobilized via its Fc on anti-human IgG coated plates. A fixed concentration of bio-IL-22 gives a signal (~2.25), bound to the plate through its interaction with IL-22R's ECD. The pre-incubation of these two antibodies with IL-22 has qualitatively different impacts on the ability of IL-22 to bind subsequently to IL-22R. Ab-04 blocks IL-22 binding to IL-22R ($ND_{50}$=0.7 nM) while Ab-02 enhances the binding of IL-22 to IL-22R ($EC_{50}$=0.1 nM). The distinct phenotypes for these antibodies in this ELISA indicate that they define different IL-22 epitopes. The epitope defined by Ab-04 is either required for the recognition of IL-22 by the ECD of IL-22R or the antibody sterically interferes with recognition of an adjacent IL-22 epitope by IL-22R.

Figure 10A:
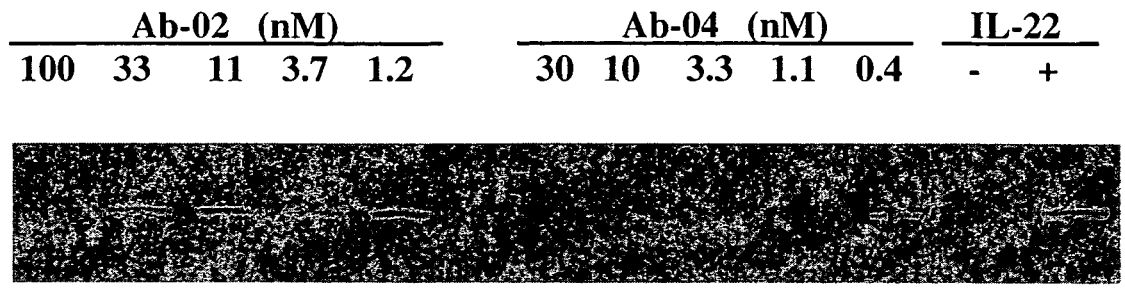
FIGS. 10A-10C represents the inhibition of IL-22 activity with rat monoclonal anti-human IL-22 antibodies (Ab-02 or Ab-04).
Figure 10B:
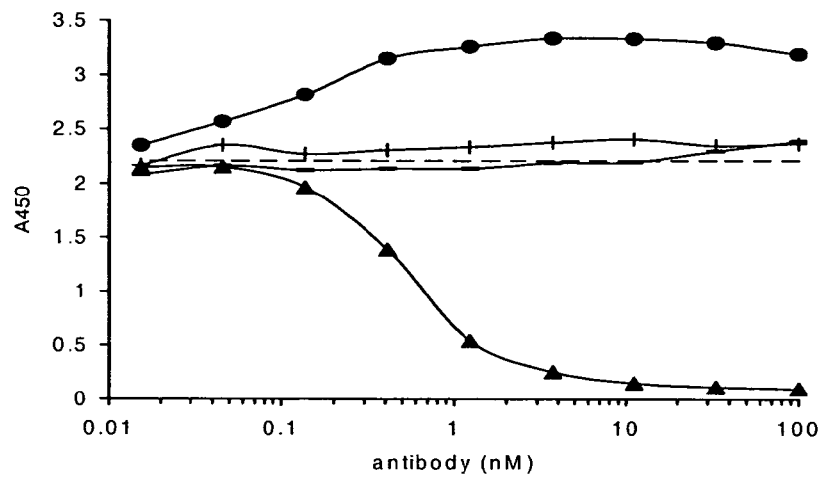
Figure 10C:
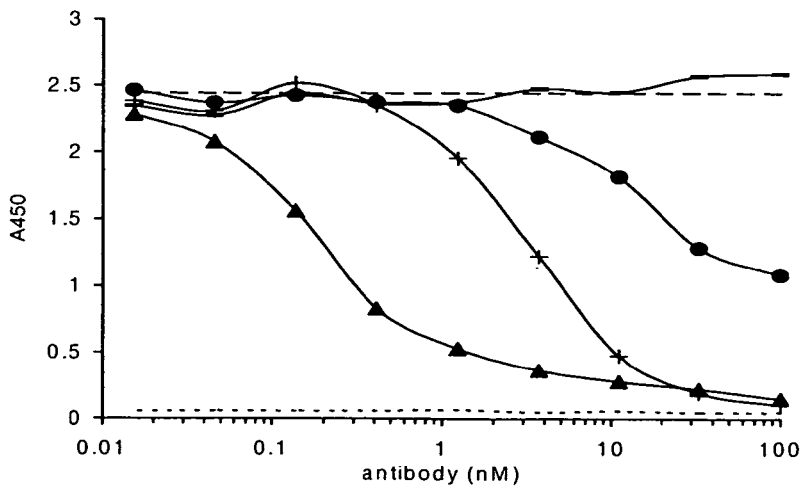

These antibodies were also evaluated for their effect on IL-22 binding when IL-22R/IL-10R2-Fc heterodimer, rather than IL-22R homodimer, was immobilized on anti-human IgG coated wells (FIG. 10C). In the experiment of FIG. 10C, the subsequent addition of a fixed amount of bio-IL-22 gave a signal (~2.5), bound to the plate through its interaction with both IL-22R and IL-10R2. In this case, both antibodies inhibit IL-22 binding to the heterodimeric Fc fusion receptor. Again, these antibodies differ qualitatively. Ab-04 inhibits binding almost completely, with an $ND_{50}$=0.2 nM. In contrast, Ab-02 inhibits binding partially, with an $ND_{50} \geq 10$ nM. We conclude that Ab-04 blocks almost completely the interaction between IL-22 and IL-22R in both IL-22R (FIG. 5B) and heterodimer (FIG. 10C) ELISAs. Ab-02's relatively low potency in the heterodimer ELISA is presumably a reflection of its relative poor affinity for IL-22. Since Ab-02 does not block the interaction between IL-22 and IL-22R (FIG. 10B), the results shown in FIG. 10C suggest that Ab-02 defines a separate epitope that is either required for IL-10R2's stabilization of IL-22 binding or binding of the Ab-02 to this epitope sterically interferes with recognition of an adjacent IL-22 epitope by IL-10R2.

A polyclonal IL-10R2 antibody was also evaluated for its ability to inhibit the binding of IL-22 to both IL-22R and receptor Fc heterodimers. In the former ELISA, where IL-10R2 is not present, increasing amounts of this antibody was added with a fixed amount of bio-IL-22 and had no significant impact on the interaction between IL-22 and the IL-22R homodimer (FIG. 10B). In contrast, when increasing amounts of IL-10R2 antibody was added with IL-22 to an ELISA that included immobilized IL-22R/IL-10R2-Fc, this antibody blocked the binding of IL-22 to the heterodimer ($ND_{50}$=3 nM, FIG. 10C). The completeness of this affect indicates that binding of this polyclonal antibody to various IL-10R2 epitopes also prevented, presumably by steric interference, the interaction between IL-22 and IL-22R.

Figure 12:
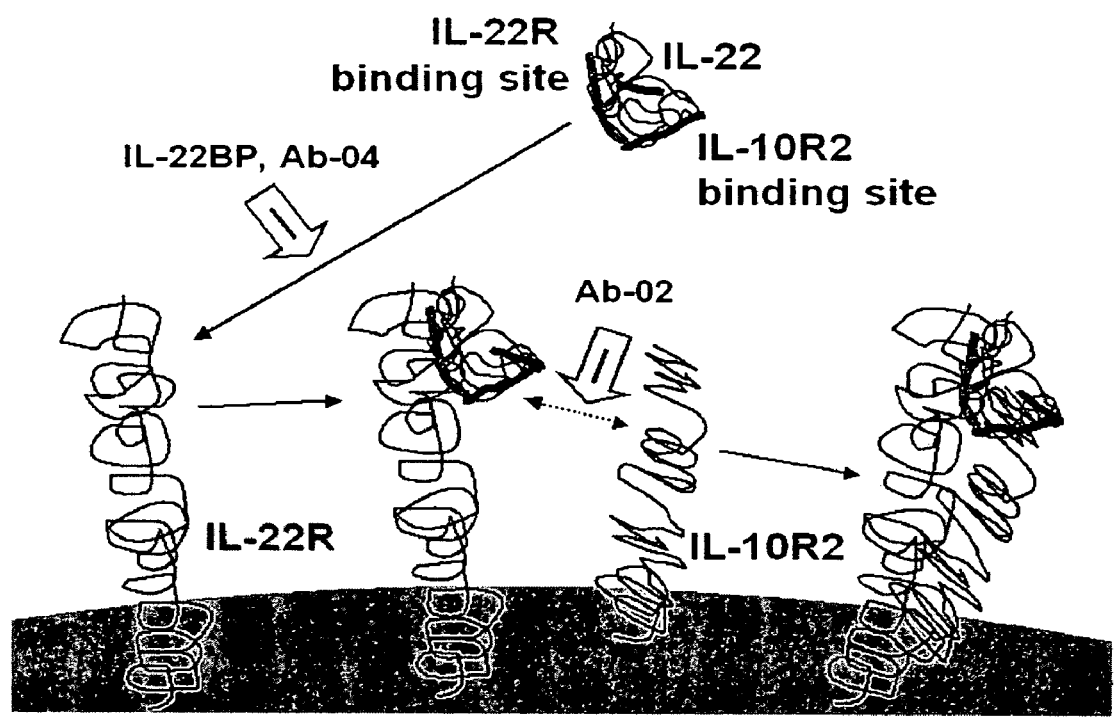
FIG. 12 is a schematic diagram depicting the assembly of an IL-22/IL-22R/IL-10R2 receptor complex. Antibodies represented by Ab-04 that bind to an epitope of IL-22, the binding of which results in blockade of an interaction between IL-22 and IL22R. Ab-04 is believed to block an interaction between IL-22 and IL-22R to a similar level as IL-22 binding protein (IL-22BP). Antibodies represented by Ab-02 bind to an epitope of IL-22, the binding of which results in blockade of an interaction between IL-22 and IL10R2. It is believed that Ab-02 reduces or blocks the formation of a complex between IL-22/IL-22R and IL-10R2.

In summary, the results shown in FIGS. 10A-10C suggest that Ab-02 and Ab-04 each define distinct epitopes on IL-22 that are important for IL-22's interaction with its receptor chains. Ab-04 defines an epitope essential for IL-22R's initial recognition of IL-22 (FIG. 12). Ab-02 defines an epitope necessary for IL-10R2's role in the stabilization of the cytokine receptor complex (FIG. 12). Comparable data with rat anti-murine IL-22 monoclonals defines similar epitopes on mIL-22 (data not shown). The inhibition of IL-22 binding by an IL10R2 polyclonal antibody further substantiates the importance of IL-10R2 for cytokine binding.

Example 17

IL-22BP Blocks the Interaction Between IL-22 and IL-22R

Figure 11A:
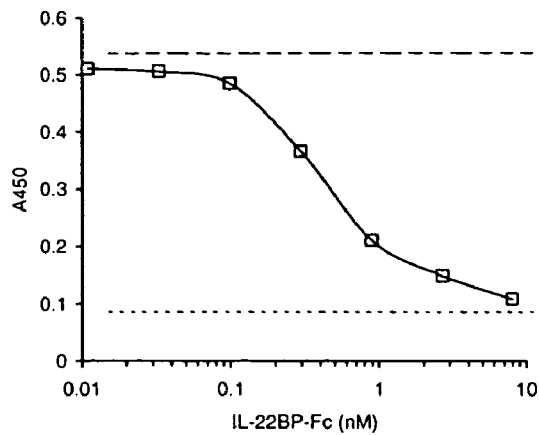
FIGS. 11A-11C represents the inhibition of IL-22 activity using IL-22BP-Fc.
Figure 11B:
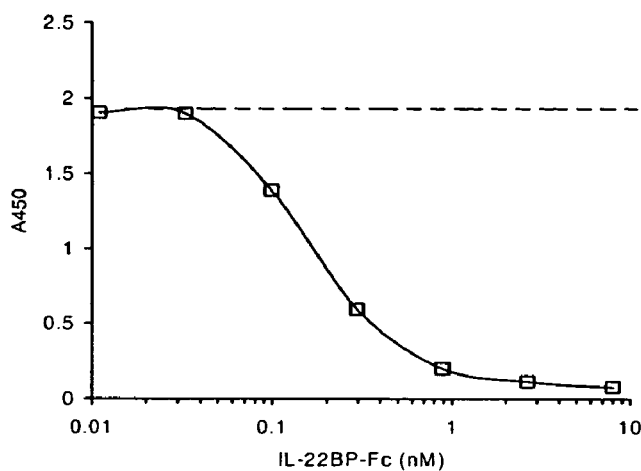

IL-22 binding protein (IL-22BP) is a soluble 'receptor' for IL-22 that has low homology to the extracellular domain of IL-22R. It neutralizes signal transduction mediated by IL-22 (Dumoutier, L. et al. (2001) *J Immunol* 166(12):7090-5; Kotenko, S. V. et al. (2001) *J Immunol* 166(12):7096-103; Xu, W. et al. (2001) *Proc Natl Acad Sci USA* 98(17):9511-6; Wei C-C et al. (2003) *Genes & Immunity* 4:204-21117). Conditioned media from CHO cells that secrete an IL-22BP-Fc fusion was added to cytokine receptor binding ELISA to determine how this natural antagonist blocks IL-22's interaction with it's receptor chains. For the experiments of FIGS. 11A and 11B, a fixed amount of total Fc from cells expressing IL-22R-Fc homodimer or IL-22R/IL-10R2-Fc heterodimer, respectively, was immobilized via its Fc on anti-human IgG coated plates. A fixed concentration of bio-IL-22 gives a signal, bound to the plate through its interaction with immobilized receptor chains. Where increasing concentrations of IL-22BP-Fc were added with a fixed concentration of IL-22, IL-22BP-Fc blocked almost completely the binding of IL-22 to both IL-22R ($ND_{50}$=4 nM; FIG. 11A) and the heterodimer ($ND_{50}$=2 nM; FIG. 6B). This suggests that IL-22BP inhibits binding by blocking an epitope of IL-22 required for its recognition by IL-22R. These observations are similar to those obtained with the Ab-04.

Figure 11C:
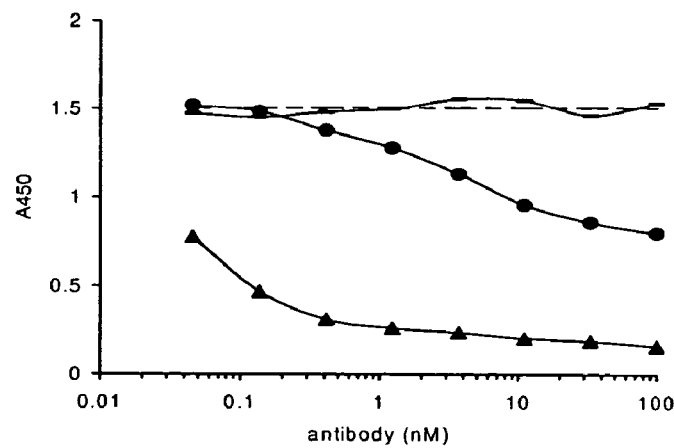

In order to determine if IL-22BP, Ab-04 and Ab-02 bind to distinct or overlapping epitopes on IL-22, a binding ELISA was employed in which IL-22BP-Fc was immobilized via its Fc onto anti-human IgG coated plates (FIG. 11C). A fixed concentration of bio-IL-22 gives a signal, bound to the plate through its interaction with IL-22BP. Increasing concentrations of Ab-04 or Ab-02 were also added with a fixed concentration of IL-22. Ab-04 blocked the interaction between IL-22 and IL-22BP completely ($ND_{50}$=0.05 nM), indicating that these two inhibitors share the same or an overlapping IL-22 epitope. In contrast, Ab-02 blocked IL-22's recognition of IL-22BP partially and weakly ($ND_{50}$=100 nM) indicating that Ab-02 and IL-22BP have distinct yet overlapping epitopes on IL-22.

In summary, the results shown in FIG. 11 indicate that IL-22BP and Ab-04 share a similar epitope on IL-22 that is important for binding to IL-22R. The IL-22 epitope defined by Ab-02 is distinct.

Example 18

IL-22 Interacts Sequentially with the ECD of IL-22R and IL-10R2

Biotinylated, N terminal HIS/FLAG tagged human IL-22 cytokine and IL-22$R_{ECD}$- and IL-10$R2_{ECD}$-Fc fusions were used in an ELISA-based format to explore how IL-22 interacts with its receptor chains. As summarized in the schematic model of FIG. 12, IL-22 may first bind to the ECD of IL-22R. Then IL-22/IL-22$R_{ECD}$ interacts with the ECD of IL-10R2 to form a cytokine receptor complex with a higher affinity for IL-22. While the stable recruitment of IL-10$R2_{ECD}$ to this complex has not been shown directly, the following observations support this model.

The interaction of IL-22 with the individual receptor subunits was examined, and found that the binding between IL-22 and IL-22R could readily be detected ($ED_{50}$=20 ng/ml IL-22 and $ED_{50}$=6 ng/ml IL-22R-Fc in FIGS. 6A and 6B, respectively). In contrast, only a weak avidity between immobilized IL-22 and soluble IL-10R2 could be detected and this required high concentrations of IL-10R2-Fc (3-10 ug/ml; data not shown). These results are consistent with the recent studies by Logsdon, N. J. et al. infra, where interactions between monomeric IL-22 and IL-22R were detected in the nanomolar range (Keq ~15 nM) while interactions between IL-22 and IL-10R2 were in the millimolar range (Keq-1 mM) (Logsdon, N. J. et al. (2002) *J Interferon Cytokine Res* 22(11): 1099-112).

Without being bound by theory, Applicants propose that the ECD of IL-10R2 subsequently associates with the initial IL-22R/IL-22$R_{ECD}$ complex, based on its affinity for an epitope defined by the interaction of IL-22 and the extracellular domain of IL-22R. This temporal engagement of the IL-10$R2_{ECD}$ stabilizes the cytokine within the receptor complex and leads to effective signal transduction (FIG. 12). Experiments involving either the prior, concomitant (FIG. 9A) or sequential addition (FIG. 9B) of soluble IL-10R2 Fc to biotinylated IL-22 in an immobilized IL-22R ELISA demonstrated that the effect of IL-10R2 on IL-22 binding is dependent on a prior IL-22/IL-22R interaction (FIG. 9). In the system used, IL-10R2-Fc cannot first associate with either IL-22 (FIG. 6) or IL-22R-Fc (FIG. 9A) in order to effect enhanced IL-22 binding. These observations are consistent with the affinity measurements of Logsdon et al. (2002) supra where immobilized IL-22's affinity for solution phase IL-10R2 alone is ~1 mM ($K_{eq}$) while its affinity for solution phase IL-22R and IL-10R2 together is twenty fold greater (~45 uM).

Stable engagement of the IL-10R2 subunit with the IL-22/IL-22R complex in this ELISA system was not detected directly using either a polyclonal or a monoclonal hIL-10R2 antibody. Both of these anti-hIL-10R2 reagents detected a pronounced non-specific binding of IL-10R2-Fc to the ELISA plates, even in the presence of 100 ug/ml human IgG and independent of the addition of IL-22R or IL-22. This high background may have masked a smaller signal derived from the IL-22/IL-22R-dependent association of IL-10R2 to the ELISA plates. Note, though, that this non-specific binding of IL-10R2-Fc does not enhance the signal derived from bio-IL-22 when cytokine was added subsequently, presumably because insufficient IL-22R-Fc is juxtaposed adjacent to IL-22R$_{ECD}$ when hIgG is added to the assay (FIG. 9A).

The covalent juxtaposition of IL-22R to IL-10R2 in the context of a heterodimer gives optimal detection of IL-22 binding in the system used herein (FIG. 8A). In effect, this covalent association increases the likelihood that the IL-10R2$_{ECD}$ will be in close proximity to an IL-22/IL-22R$_{ECD}$ complex, once cytokine is added to the assay. These heterodimers may artificially mimic a potential pre-association between the IL-22R and IL-10R2 receptor subunits within a cell membrane. Studies in a single cell FRET system developed by Krause et al. (2002) *Molecular & Cellular Proteomics* 1(10):805-15 indicate that pre-associations between fully-functional IFN-γR1 and IFN-γR2 receptor chains can be detected via C terminal GFP and BFP fusions, With binding of IFN-γ to cells in this system, and the presumed oligomerization of the cytokine-receptor complex, the FRET signal decreases, suggesting the intracellular domains separate as kinases phosphorylate the receptor chains and amplify the downstream signal cascade. In one model, the temporal IL-22 cytokine receptor interactions studied in the ELISA system models described herein the interactions required for the oligomerization of pre-associated IL-22 receptor chains, as well as other type II cytokine receptors, within a cell membrane.

Example 19

IL-22 has Separate IL-22R and IL-10R2 Binding Surfaces

The rat IL-22 antibodies, Ab-02 and Ab-04, have proven to be useful tools for assessing potential binding sites on IL-22 epitopes that are required for the proposed temporal assembly of the cytokine-receptor complex and subsequent signal transduction (FIG. 12). The study of the effects of these antibodies enables the characterization of two types of IL-22 antagonists. The first type, exemplified by Ab-04 and hIL-22BP-Fc, blocks the initial interaction between IL-22 and IL-22R (FIGS. 10B and 12). The second type of inhibitor, exemplified by Ab-02, blocks the subsequent recognition of IL-22/IL-22R$_{ECD}$ by IL-10R2$_{ECD}$ (FIGS. 10C and 12). These antibodies also block signal transduction mediated by IL-22 (FIG. 10A).

Whether the epitopes defined by the IL-22 antibodies overlap the receptor binding sites or binding site of the antibody sterically interferes with the recognition of the cytokine by the receptor chain, these two types of antibodies confirm that IL-22 has distinct receptor binding sites for IL-22 and IL-10R2. Focusing on characteristics of the antibodies reported here, Ab-04 binds to an IL-22 epitope that prevents the recognition of IL-22 by IL-22R; this is not the case for Ab-02. Association of IL-22 with IL-22R is not blocked by Ab-02. In fact, Ab-02 enhances the binding of IL-22 to immobilized IL-22R (FIG. 5B). It is believed that this is due to Ab-02's recognition of a conformational change in IL-22 that is effected by this cytokine's interaction with the ECD of IL-22R. While Ab-02 does not block the first step in cytokine assembly, it is able to block the second step (i.e., recognition of IL-22/IL-22R by ECD of IL-10R2). It is, therefore, concluded that Ab-04 and Ab-02 block the recognition of distinct binding sites by IL-22R and IL-10R2, respectively, on IL-22. The naturally-occurring antagonist and binding protein for IL-22, IL-22BP, has similar characteristics as Ab-04, interfering with the recognition of IL-22 by IL-22R (FIG. 11A). The ability of Ab-04 to strongly interfere with the binding of IL-22 to immobilized IL-22BP-Fc further supports the conclusion that Ab-04 and IL-22BP share a similar epitope on IL-22 that is distinct from that defined by Ab-04.

In summary, the results shown herein suggest that IL-22 interacts with its receptor chains in a temporal mechanism. First, IL-22 associates with the ECD of IL-22R where antagonists exemplified by Ab-04 and IL-22BP-Fc prevent this interaction. Second, the ECD of IL-10R2 binds to a distinct binding site defined by the prior interaction between IL-22 and IL-22R. This latter interaction is blocked by antagonists exemplified by Ab-02 (FIG. 12).

Example 20

Inhibition of IL-22 Activity in a pSTAT Luciferase Assay Using Rat Anti-Human IL-22 Antibodies Experimental Protocols:

The pSTAT-TA-Luciferase vector was constructed as follows: Five copies of STAT responsive elements (RN Pearse et al. (1993) *PNAS* 90: 43144318) were cloned into pTA-Luc vector obtained from a commercial source (Clontech Cat. No.: PT3606-5).

Luciferase activity was detected using the following pSTAT Luciferase assay: On the first day, HepG2 cells were fully trypsinised and split into P-100 dishes (Corning) at a density of $5 \times 10^6$ cells/P100). On the second day, the cells were transfected under the following conditions per P100 plate: Solution 1: 20 ug pSTAT-TA-Luc DNA+0.5 ml Serum-free medium (Opti-MEM from Gibco); and Solution 2: 60 ul Lipofectamin2000 (from Gibco)+0.5 ml Serum-free medium (Opti-MEM from Gibco). Solution 1 was gently added into Solution 2 and mixed well by inverting the tube several times. The mixture was allowed to stand for 20 minutes at room temperature. The medium from HepG2 cells was removed and washed once with phosphate buffered saline solution (PBS). 9 ml/p100 of serum-free medium (DME+PSG+HEPES) were added to P100. A dropwise addition of the DNA/Lipofectamin 2000 mixture (Solution 1+Solution 2) was added to the cells. The mixture was swirled gently and returned to the incubator. On the third day, cells were trypsinised and plated in a 96-well cell culture flat bottomed plate, one 96 well plate/p100, 100 µl/well. On the fourth day, a series of antibody dilutions was preincubated with 30 ng/ml of huIL-22 in DME+PSG+10% FBS at 37° C. for 30 minutes. 100 µl of the antibody:cytokine mixture was then added to cell culture plates after medium was removed. The cells were incubated at 37° C. for 6 hours. The medium was removed, 50 ul/well for 96-well plate of 1×RLB buffer (Promega E3971) were added and mixed until homogenous. 40 ul of lysate were transferred for luciferase assay into chemoluminescence 96-well assay plates (Packard or Wallac opaque 96-well plates). 100 ul of Luciferase assay reagent (Promega E1483)

were added. Luminescence was scored in Luminometer (Wallax Micro Beta TriLux scintillation counter).

Figure 13:
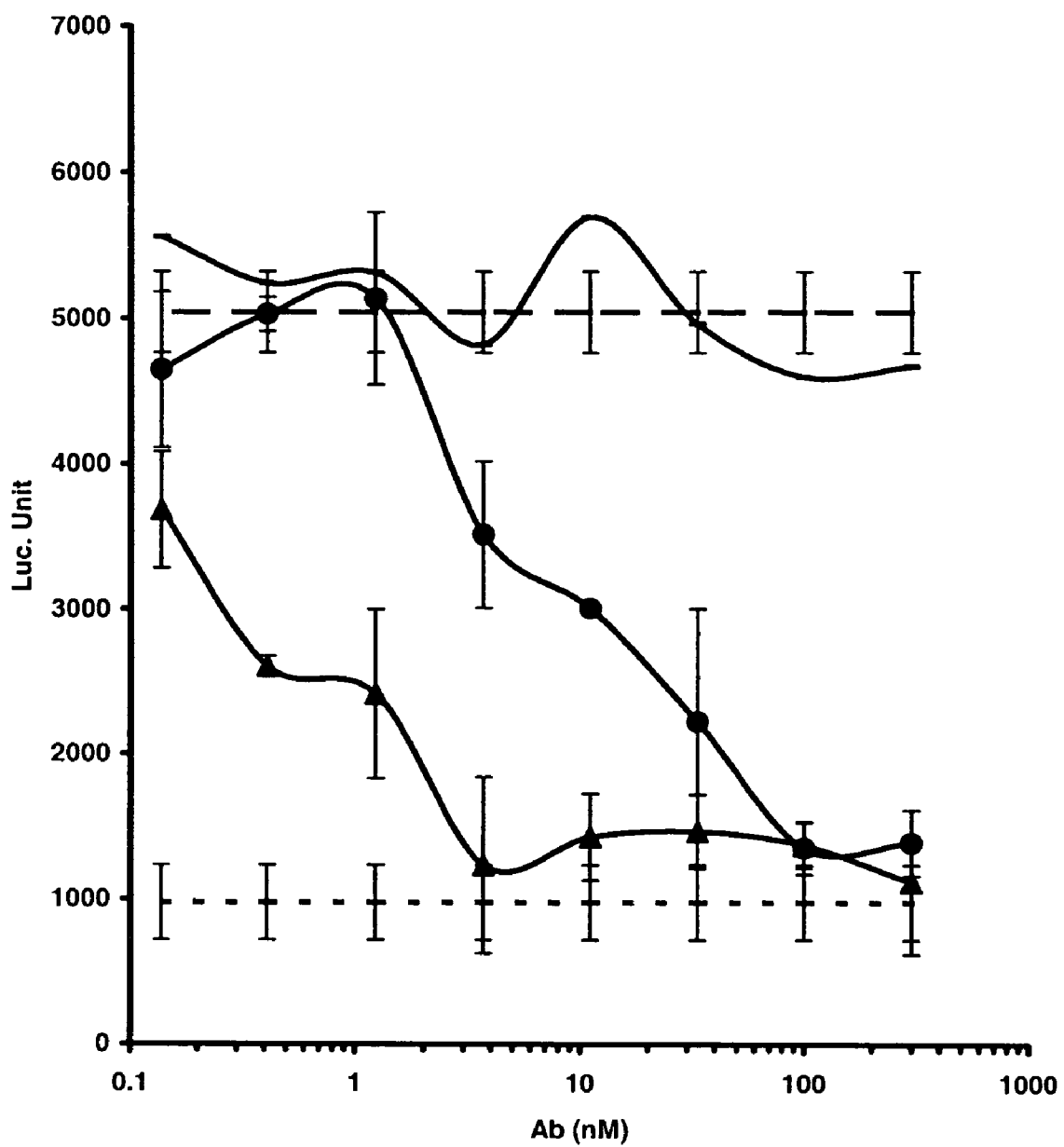
FIG. 13 is a graph depicting the inhibition of IL-22 activity with rat anti-human IL-22 monoclonal antibodies. A fixed concentration of IL-22 was pre-incubated with various concentrations of either Ab-02 (•) or Ab-04 (▲) or a control antibody (−) in cell media and then added to HepG2 cells transiently transfected by pSTAT-TA-Luc vector.

This Example describes the inhibition of IL-22 activity in a pSTAT Luciferase assay using rat anti-human IL-22 antibodies, Ab-02 and Ab-04, compared to a fusion construct of human IL22 binding protein fused to Fc (huIL22BP-huFc). FIG. 13 is a graph depicting inhibition of IL-22 activities using rat anti-human IL-22 monoclonal antibodies, Ab-02 and Ab-04. A fixed concentration of IL-22 was pre-incubated with various concentrations of either Ab-02 (•) or Ab-04 (▲) or a control antibody (−) in cell media and then added to HepG2 cells transiently transfected by pSTAT-TA-Luc vector. After 6 hrs, the cells were lysed and same amount of cell lysates were added with luciferase substrate. The signal was detected using a luminescence reader. Cells incubated with (broken line) or without (dot line) IL-22 were included as positive and negative controls, respectively. ED50 for Ab-02 was about 10 nM. The ED50 for Ab-04 was about 0.3 nM.

Figure 14:
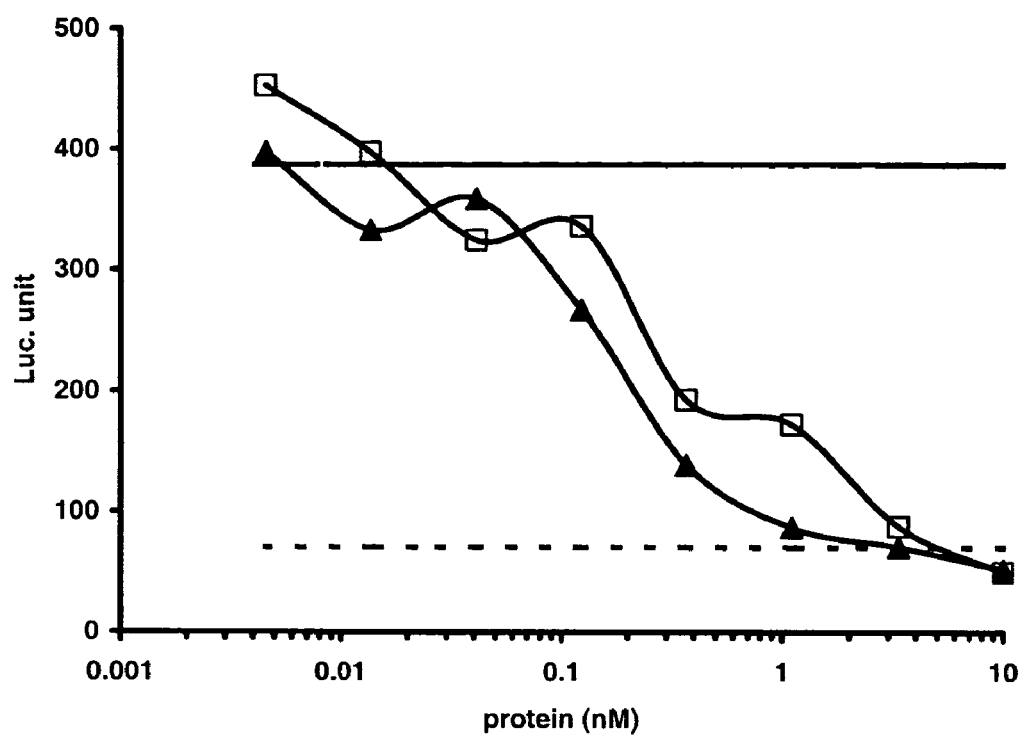
FIG. 14 is graph depicting the inhibition of IL-22 activities with rat anti-human IL-22 monoclonal antibody and IL-22BP-Fc. A fixed concentration of IL-22 was pre-incubated with various concentrations of either Ab-04 (▲) or IL-22BP-Fc (□) in cell media and then added to HepG2 cells transiently transfected by pSTAT-TA-Luc vector.

FIG. 14 is a graph depicting the inhibition of IL-22 activities with rat anti-human IL-22 monoclonal antibody, Ab-04, or IL-22BP-Fc. A fixed concentration of IL-22 was pre-incubated with various concentrations of either Ab-04 (▲) or IL-22BP-Fc (□) in cell media and then added to HepG2 cells transiently transfected by pSTAT-TA-Luc vector. After 6 hrs, the cells were lysed and same amount of cell lysates were added to each sample with luciferase substrate. The signal was detected using a luminescence reader. Cells incubated with (broken line) or without (dot line) IL-22 were included as positive and negative controls, respectively. ED50 for IL-22BP-Fc was about 0.4 nM.

Example 21

Inhibition of IL-22 Activity in BaF3 Proliferation Assay Using Rat Anti-Human IL-22 Antibodies Experimental Protocols:

DNA fragments encoding full length IL-22R and IL-10R2 were cloned into GFP-RV (retroviral vector with Green Fluorescent Protein Reporter) and YFP-RV (retroviral vector with Yellow Fluorescent Protein) respectively. The BaF3 cells were transduced with IL-10R2—YFP-RV and sorted by FACS. The IL-10R2 positive BaF3 cells were further transduced with IL-22R-GFP RV and sorted by FACS. The IL-10R2/IL-22R double positive BaF3 cells were used in the BaF3 proliferation assay as described below.

BAF3 cells were washed. A cell suspension at 105/ml was prepared in RPMI1640+PSG+10% FBS and aliquot 50 ul/well in cell culture plate (VWR # 62402-929). The series diluted antibody was pre-incubated with 1.5 ng/ml human IL-22 in RPMI1640+PSG+10% FBS at 37° C. for 30 minutes. The mixture was then added into cell culture plate at 50 ul/well. Cells were incubated at 37° C. in 5% CO$_2$ in a humidified incubator for 48-72 hours. To assess proliferation, the cultured plates were removed out of incubator and allowed to cool down to room temperature. About 100 ul/well of reconstituted Cell-Titer Glo reagent were added. The plates were shaken on orbital shaker for 2 min to ensure complete lysis of cells. Luminescence was read 1 sec/well using Trilux (Wallax Micro Beta TriLux scintillation counter).

Figure 15:
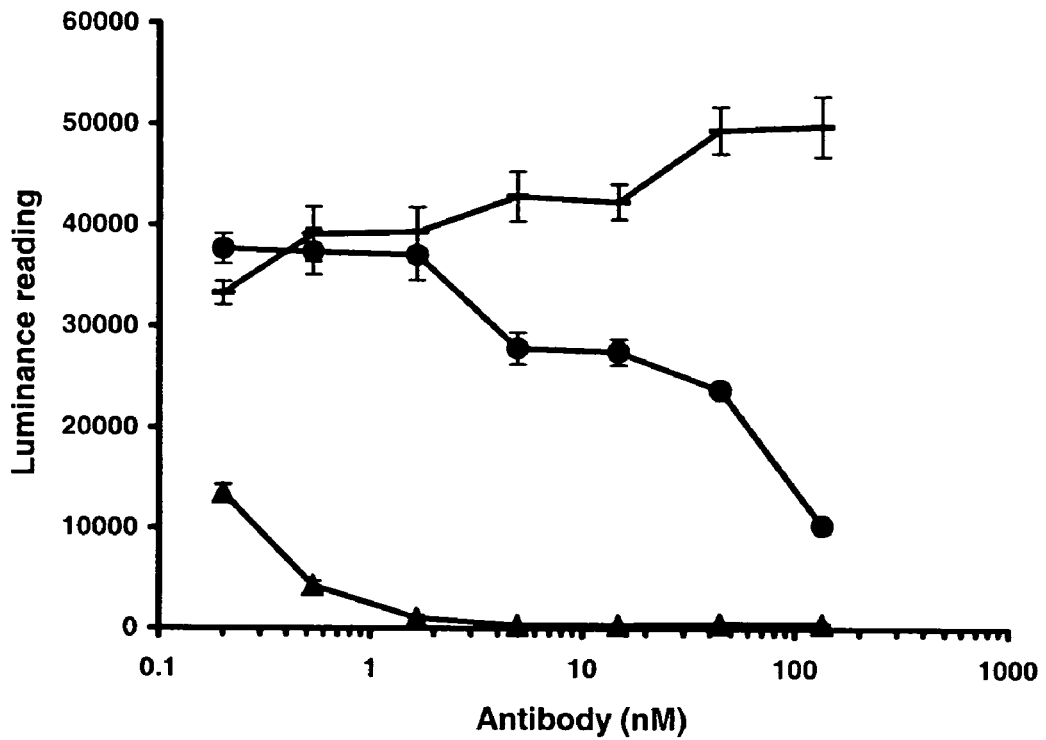
FIG. 15 is a graph depicting the inhibition of IL-22 activities with rat anti-human IL-22 monoclonal antibodies. A fixed concentration of IL-22 was pre-incubated with various concentrations of either Ab-02 (•) or Ab-04 (▲) or a control antibody (−) in cell media and then added to BaF3 cells expressing both IL-22R and IL-10R2 receptors.

This Example describes the inhibition of IL-22 activity in BaF3 proliferation assay using rat anti-human IL-22 antibodies, Ab-02 and Ab-04 (FIG. 15). A fixed concentration of IL-22 was pre-incubated with various concentrations of either Ab-02 (•) or Ab-04 (▲) or a control antibody (−) in cell media and then added to BaF3 cells expressing both IL-22R and IL-10R2 receptors. After 48-72 hours, cell proliferation was detected by Cell-Titer Glo reagent. The signal was detected using a uminescence reader. ED50 for Ab-02 and Ab-04 were about 40 nM and 0.2 nM, respectively.

Example 22

Kinetic Analysis of Rat Ab-02, 04, IL-22BP-Fc. IL-22R and IL-22R/IL-10R2 Binding to IL-22 by BIAcore Experimental Protocols:

To prepare the biosensor surface, goat anti-human IgG affinity purified (KPL 01-10-20); Protein-A (Pierce 21184); goat anti-rat IgG or test protein directly were immobilized onto a research-grade carboxymethyl dextran chip (CM5) using amine coupling. The surface was activated with EDC/NHS. The capturing antibody was injected at a concentration of 50 ug/ml in sodium acetate buffer (pH 4.5), the Protein-A was injected at a concentration of 50 ug/ml in sodium acetate buffer (pH 4.0), or test protein was directly injected at a concentration of 0.01-1 ug/ml in sodium acetate buffer (pH 5.0). The immobilization was done using the wizard tools with aim of 10.000 resonance units (RUs) for the anti-hu or anti-rat IgG, 3000 (RUs) for the Protein-A and 50100 (RUs) for the directly immobilized testing protein. Remaining activated groups were blocked with 1.0 M ethanolamine (pH 8.0). As control the first flow cell was used as reference surface to correct for bulk refractive index, matrix effects and non-specific binding, the second, third and four flow cells were coated with the capturing molecule.

For kinetic analysis, condition media containing IL-22R-Fc, IL-10R2-Fc, IL-22R-Fc/IL-10R2-Fc receptor complex or IL-22BP-Fc protein were captured onto the anti-human IgG antibody or protein A surfaces. The rat antibodies were captured onto the anti-rat IgG antibody surface, by injecting 60 ul of a 400 ng/ml solution. The net difference between the baseline and the point approximately 90 sec after completion of Fc fusion protein injection was taken to represent the amount of ligand bound. Solutions of IL-22 at 300, 150, 100, 75, 50, 25, 12.5, 6.5, and 0 nM concentrations were injected in triplicates at a flow rate of 30 ul per min for 3 minutes and the amount of bound material as a function of time was recorded as sensorgrams. The dissociation phase was monitored in HBS/EP buffer for 10 minutes at the same flow rate followed by 5 ul injection of 0.1% TFA and 5 ul injection of glycine pH 1.5 to regenerate a fully active capturing surface. A 11 kinetic experiments were done at 22.5° C. in HBS/EP buffer. Blank and buffer effects were subtracted for each sensorgram using double referencing.

The kinetic data were analyzed using BIAevaluation software 3.0.2 applied to a 1:1 model. The apparent dissociation ($k_d$) and association ($k_a$) rate constants were calculated from the appropriate regions of the sensorgrams using a global analysis. The affinity constant of the interaction between receptors, antibodies and IL-22 was calculated from the kinetic rate constants by the following formula: $K_D = k_d/k_a$.

The affinity of rat antibodies binding to IL-22 has been tested in BIAcore using different presentation of rat antibodies: directly coating rat antibodies on BIAcore chip or capturing rat antibodies on BIAcore chip by anti-rat IgG antibodies. Then, different concentrations of IL-22 were injected into chip followed with buffer. The affinity constant of the interaction was analyzed using BIAevaluation software. Similar data have been obtained from different experiments.

The affinity of IL-22R-Fc, IL-10R2-Fc, IL-22R-Fc/IL10R2-Fc receptor complex and IL-22BP-Fc binding to IL-22 has been tested in BIAcore using conditioned medium containing above receptor-Fc fusion protein. The receptor-Fc fusion protein was captured on BIAcore chip by anti-human IgG antibodies. Then, different concentrations of IL-22 were injected into chip followed with buffer. The affinity constant of the interaction was analyzed using BIAevaluation software. Similar data have been obtained from different experiments.

|  | Ab-02 | Ab-04 | IL-22R-Fc | IL-22R-Fc/IL-10R2-Fc complex | IL-22BP-Fc |
|---|---|---|---|---|---|
| $K_D$ (nM) | 68.1 | 1.51 | 41 | 1.48 | 3.37 |

*The interaction between IL-10R2-Fc and IL-22 was too weak to be tested in BIAcore analysis.

Deposit of Hybridoma Cell Lines

Hybridoma cell lines producing Ab-02 and Ab-04 were deposited with the American Type Culture Collection, 10801 University Boulevard, Manassas, Va., U.S.A. 20110-2209, on Jun. 5, 2003 as an original deposit under the Budapest Treaty and assigned ATCC accession numbers PTA-5254 and PTA-5255, respectively. All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

EQUIVALENTS

Those skilled in the art will recognize, or be able to ascertain using no more than routine experimentation, many equivalents to the specific embodiments of the invention described herein. Such equivalents are encompassed by the following claims.

What is claimed is:

1. A monoclonal antibody produced by a hybridoma chosen from PTA-5254 and PTA-5255.

* * * * *

UNITED STATES PATENT AND TRADEMARK OFFICE
CERTIFICATE OF CORRECTION

| | | |
|---|---|---|
| PATENT NO. | : 7,638,604 B2 | Page 1 of 1 |
| APPLICATION NO. | : 10/873972 | |
| DATED | : December 29, 2009 | |
| INVENTOR(S) | : Li et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 538 days.

Signed and Sealed this
Third Day of May, 2011

David J. Kappos
*Director of the United States Patent and Trademark Office*